US011560413B2

(12) United States Patent
Kappes et al.

(10) Patent No.: US 11,560,413 B2
(45) Date of Patent: Jan. 24, 2023

(54) MODIFIED CYSTIC FIBROSIS TRANSMEMBRANE CONDUCTANCE REGULATOR (CFTR) POLYPEPTIDES WITH INCREASED STABILITY AND USES THEREOF

(71) Applicants: UAB Research Foundation, Birmingham, AL (US); Texas Tech University System, Lubbock, TX (US)

(72) Inventors: John C. Kappes, Homewood, AL (US); Zhengrong Yang, Hoover, AL (US); Christie G. Brouillette, Birmingham, AL (US); Ina L. Urbatsch, Lubbock, TX (US)

(73) Assignees: UAB Research Foundation, Birmingham, AL (US); Texas Tech University System, Lubbock, TX (US)

( * ) Notice: Subject to any disclaimer, the term of this patent is extended or adjusted under 35 U.S.C. 154(b) by 49 days.

(21) Appl. No.: 16/277,888

(22) Filed: Feb. 15, 2019

(65) Prior Publication Data
US 2019/0248855 A1 Aug. 15, 2019

Related U.S. Application Data

(60) Provisional application No. 62/631,364, filed on Feb. 15, 2018.

(51) Int. Cl.
*C07K 14/47* (2006.01)
*C07K 14/705* (2006.01)
*G01N 33/68* (2006.01)

(52) U.S. Cl.
CPC ........ *C07K 14/4712* (2013.01); *C07K 14/705* (2013.01); *G01N 33/6872* (2013.01); *G01N 2333/705* (2013.01); *G01N 2800/382* (2013.01); *G01N 2800/50* (2013.01)

(58) Field of Classification Search
CPC .............. C07K 14/4712; C07K 14/705; G01N 33/6872
See application file for complete search history.

(56) References Cited

PUBLICATIONS

Verkman and Galietta. "Chloride channels as drug targets"; Nature Reviews Drug Discovery vol. 8, pp. 153-171(2009) (Year: 2009).*

(Continued)

*Primary Examiner* — Xiaozhen Xie
(74) *Attorney, Agent, or Firm* — Myers Bigel, P.A.

(57) ABSTRACT

The present invention is directed to modified CFTR proteins or fragments thereof that contain single or multiple amino acid mutations to improve the structural stability of such CFTR proteins and/or fragments. Specifically, the modified CFTR proteins or fragment thereof differ from the wild-type human CFTR protein or fragment thereof by the presence of four or more mutations selected from V150D, M470V, S492P, F494N, S495P, A534P, I539T, G550E, G551D, R553Q, R555K, Q637R, S1255L, K1334G, S1359A, E1371Q, H1402S, Q1411D, and any combination thereof, such that the stability of the polypeptide is increased relative to that of the wild-type human CFTR polypeptide or fragment thereof.

16 Claims, 17 Drawing Sheets

Specification includes a Sequence Listing.

(56) References Cited

PUBLICATIONS

Urbatsch, I.L. "Thermal Stabilization of purified CFTR by mutations in the nucleotide binding domains and by specific phospholipids" (presentation from 30th Annual North American Cystic Fibrosis Conference, Oct. 28, 2016; screen captures from archive at arc.nacfconference.org/cff/sessions/555/view) (Year: 2016).*
Hildebrandt et al in "A Stable Human-Cell System Overexpressing Cystic Fibrosis Transmembrane Conductance Regulator Recombinant Protein at the Cell Surface"; Mol Biotechnol (2015) 57:391-405 (Year: 2015).*
He et al., J. Mol. Biol., 2015, vol. 427(1):106-120.*
Vernon et al., J. Biol. Chem., 2017, 292(34):14147-14164.*
He et al. "Restoration of NBD1 thermal stability is necessary and sufficient to correct deltaF508 CFTR folding and assembly", J. Mol. Biol. 427(1):106-120 (2015).
He et al. "Restoration of domain folding and interdomain assembly by second-site suppressors of the deltaF508 mutation in CFTR", FASEB J 24(8):3103-3112 (2010).
Aleksandrov et al. "Allosteric modulation balances thermodynamic stability and restores function of deltaF508 CFTR", J. Mol. Biol. 419(0):41-60 (2012).
Aleksandrov et al. "Thermal stability of purified and reconstituted CFTR in a locked open channel conformation", Protein Expr Purif, 116:159-166 (2015).
Lukacs et al. "CFTR: folding, misfolding and correcting the deltaF508 conformational defect", Trends Mol Med. 18 (2):81-91 (2012).
Mendoza et al. "Requirements for Efficient Correction of deltaF508 CFTR Revealed by Analyses of Evolved Sequences", Cell. 148(1-2):164-174 (2012).
DeCarvalho et al. "Mutations in the Nucleotide Binding Domain 1 Signature Motif Region Rescue Processing and Functional Defects of Cystic Fibrosis Transmembrane Conductance Regulator deltaF508", J. Biol. Chem. 277 (39):35896-35905 (2002).
Sosnay et al. "Defining the disease liability of variants in the cystic fibrosis transmembrane conductance regulator gene", Nature Genetics 45(10):1160-1167 (2013).
Amaral et al. "Rescuing Mutant CFTR; A Multi-task Approach to a Better Outcome in Treating Cystic Fibrosis", Current Pharmaceutical Design 19:3497-3508 (2013).
Quon et al. "New and emerging targeted therapies for cystic fibrosis", BMJ 352:I859 (2016) (30 pages).
Veit et al. "From CFTR biology toward combinatorial pharmacotherapy: expanded classification of cystic fibrosis mutations", Mol. Biol. Cell 27:424-433 (2016).
Du et al. "The deltaF508 cystic fibrosis mutation impairs domain-domain interactions and arrests post-translational folding of CFTR", Nat. Struct. Mol. Biol. 12(1):17-25 (2005).
Protasevich et al. "Thermal unfolding studies show the disease causing F508del mutation in CFTR thermodynamically destabilizes nucleotide-binding domain 1", Protein Sci. 19:1917-1931 (2010).
Wang et al. "Integrated biophysical studies implicate partial unfolding of NBD1 of CFTR in the molecular pathogenesis of F508del cystic fibrosis", Protein Sci. 19:1932-1947 (2010).
Thibodeau et al. "The Cystic Fibrosis-causing Mutation deltaF508 Affects Multiple Steps in Cystic Fibrosis Transmembrane Conductance Regulator Biogenesis", J. Biol. Chem. 285(46):35825-36835 (2010).
Hudson et al. "Conformational Changes Relevant to Channel Activity and Folding within the first Nucleotide Binding Domain of the Cystic Fibrosis Transmembrane Conductance Regulator", J. Biol. Chem, 287(34):28480-28494 (2012).
Tombline et al. "Combined Mutation of Catalytic Glutamate Residues in the Two Nucleotide Binding Domains of P-glycoprotein Generates a Conformation that Binds ATP and ADP Tightly", J. Biol. Chem. 279:31212-31220 (2004).
Rabeh et al. "Correction of Both NBD1 Energetics and Domain Interface is Required io Restore deltaF508 CFTR Folding and Function" Cell 148:150-163 (2012).

Liu et al. "Thermal Instability of delta F508 CFTR Channel Funnction: Protection by Single Suppressor Mutations and Inhibiting Channel Activity", Biochemistry 51(25):5113-5124 (2012).
Xu et al. "Revertant mutants modify, but do not rescue, the gating defect of the cystic fibrosis mutant G551D-CFTR", J. Physiol. 529.9:1931-1947 (2014).
Pissarra et al. "Solubilizing Mutations Used to Crystallize One CFTR Domain Attenuate the Trafficking and Channel Defects Caused by the Major Cystic Fibrosis Mutation", Chemistry & Biology 15:62-69 (2008).
Meng et al. "The cystic fibrosis transmembrane conductance regulator (CFTR)and its stability", Cell. Mol. Life Sci. 74:23-38 (2017).
Aleksandrov et al. "Regulatory insertion removal restores maturation, stability and function of deltaF508 CFTR", J. Mol. Biol. 401(2):194-210 (2010).
Cuppens et al. "Polyvariant mutant cystic fibrosis transmembrane conductance regulator genes. The polymomhic (Tg) locus explains the partial penetrance of the T5 polymorphism as a disease mutation. ", J. Clin. Invest. 101(2):487-496 (1998).
Hildebrandt et al, "Specific stabilization of CFTR by phosphatidyiserine", Biochimica et Biophysica Acta 1859:289-293 (2017).
Tulumello et al. "Efficiency of detergents at maintaining membrane protein structures in their biologically relevant forms", Biochimica et Biophysica Acta 1818:1351-1358 (2012).
Vernon et al. "Stabilization of a nucleotide-binding domain of the cystic fibrosis transmembrane conductance regulator yields insight into disease-causing mutations", J. Biol. Chem. 292(34):14147-14164 (2017).
Powl et al. "Transmembrane and extramembrane contributions to membrane protein thermal stability: Siudies with the NaChBac sodium channel", Biochimica et Biophysica Acta 1818:889-895 (2012).
Yang et al. "Interactionsand cooperativity between P-glycoprotein structural domains determined by thermal unfolding provides insights into its solution structure and function", Biochimica et Biophysica Acta 1859:48-60 (2017).
Shibata et al. "Optimising the combination of thermostabilising mutations in the neurotensin receptor for structure determination", Biochimica et Biophysics Acta 1828:1293-1301 (2013).
Zaitseva et al. "H682 is the linchpin of ATP hydrolysis in the nucleotide-binding domain of the ABC transporter HlyB" The EMBO Journal 24(11):1901-1910 (2005).
Heydenreich et al. "Stabilization of G protein-coupled receptors by point mutations", Frontiers in Pharmacology 6 (82):1-15 (2015).
Vaidehi et al. "How do mutations thermostabilize G protein-coupled receptors?", Trends Pharmacol Sci. 37(1):37-46 (2016).
Wei et al. "Suppressive interactions between mutations located in the two nucleotide binding domains of CFTR", FEBS Letters 473:149-153 (2000).
Ciminelli et al. "Highly preferential association of NonF508del CF mutations with the M470 allele", Journal of Cystic Fibrosis 6:15-22 (2007).
Urlinger et al. "Exploring the sequence space for tetracycline-dependent transcriptional activators: Novel mutations yield expanded range and sensitivity", PNAS 97(14):7963-7968 (2000).
Serrano-Vega et al. "Conformational thermostabilization of the beta1-adrenergic receptor in a detergent-resistant form", PNAS 105(3):877-882 (2008).
Martiniano et al. "Cystic fibrosis: a model system for precision medicine", Curr Opin Pediatr 28(3):312-317 (2016).
Atwell et al. "Structures of a minimal human CTFR first nucleotide-binding domain as a monomer, head-to-tail homodimer, and pathogenic mutant", Protein Eng. Design & Selection 23(51:375-384 (2010).
Sheridan "First cystic fibrosis drug advances towards approval", Nature Biotechnology 29(6):465-466 (2011).
Zhenin et al. "REMD Simulations Reveal the Dynamic Profile and Mechanism of Action of Deleterious, Rescuing, and Stabilizing Perturbatians to NBD1 from CFTR", J. Chem. Inf. Model 55:2349-2364 (2015).

(56) References Cited

PUBLICATIONS

Hildebrandt et al. "A Stable Human-Cell System Overexpressing Cystic Fibrosis Transmembrane Conductance Regulator Recombinant Protein at the Cell Surface", Mol Biotechnol 57:391-405 (2015).

Stankova et al. "Conformational transitions of proteins engaged in DNA double-strand break repair, analysed by tryptophan fluorescence emission and FRET", Biochem J. 443:701-709 (2012).

Quen; et al. "New and emerging targeted therapies for cystic fibrosis", BMJ 352:i859 (2016).

Zhang et al. "Lumacaftor/ivacaftor combination for CF patients homozygous for Phe508del-CFTR", Drugs Today (Barc). 52(4):229-237 (2016).

Schneider et al., "Can cystic fibrosis patients finally catch a breath with Orkambi?", Clin Pharmacol Ther. 101 (1):130-141 (2017).

Haltia et al. "Forces and factors that contribute, to the structural stability of membrane proteins's", Biochimica et Biophysica Acta 1241:295-322 (1995).

Linsdell "Structural Changes Fundamental to Gating of the Cystic Fibrosis Transmembrane Conductance Regulator Anion Channel Pore", Adv Exp Med. Biol—Protein Reviews 1:13-32 (2017).

Teem et al. "Identification of Revertants for the Cystic Fibrosis deltaF508 Mutation Using STE6-CFTR Chimeras in Yeast", Cell 73:335-346 (1993).

Estacio et al. "Thermal unfolding simulations of NBD1 domain variants reveal structural motifs associated with the impaired folding of F508del-CFTR", Mol. BioSyst. 12:2834-2848 (2016).

Yang et al. "Identification of "Super" Thermostabilizing NBD1 Mutations Human CFTR Destined for Large-Scale Purification and Biophysical Characterization", Pediatr. Pulmonol. 51:218 (2016).

Bridges et al. "Differential Responses of M Versus V 470-F508DEL-CFTR to CFTR Modulators", Pediatr. Pulmonol. 48:209 (2013).

Teem et al. "Mutation of R555 in CFTR-deltaF508 Enhances Function and Partially Corrects Defective Processing", Receptors and Channels 4:63-72 (1972).

* cited by examiner

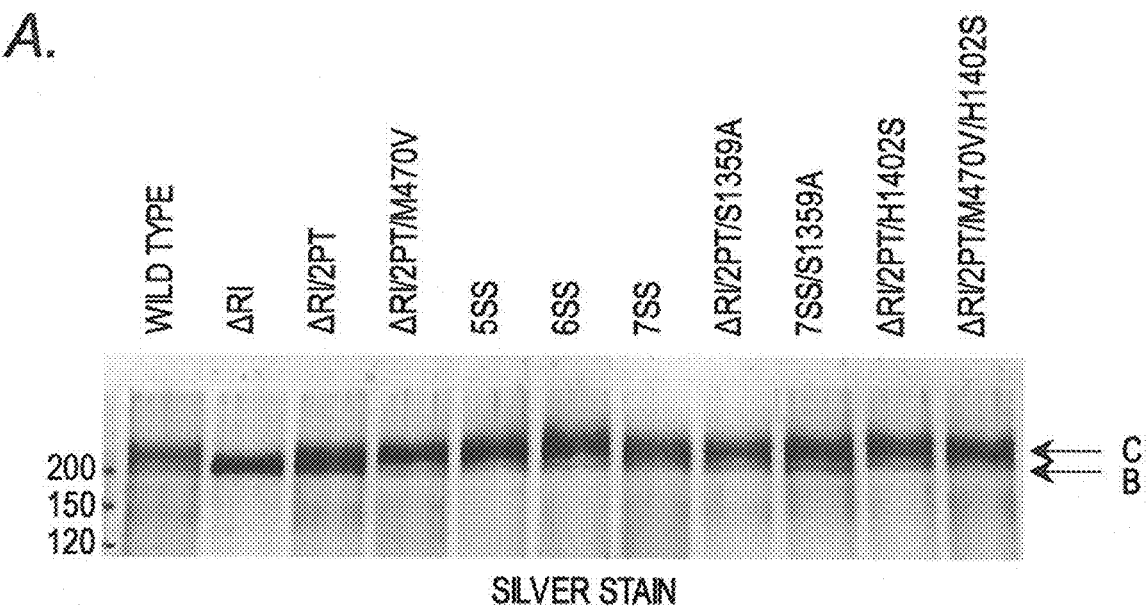
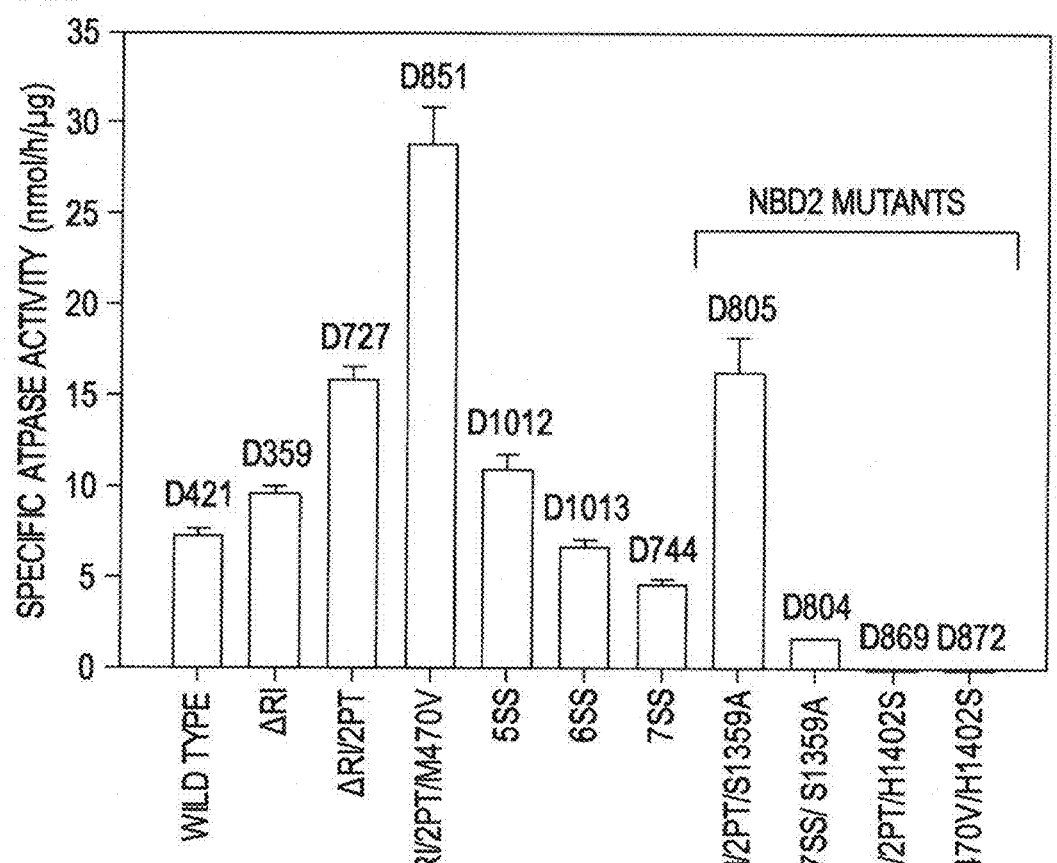
FIG. 3

```
HUMAN CFTR     (458)  GSTGAGKTSLLMMIMGELEPSEGKIKHSGRIS----FCSQFSWIMPGTI
      hABCC4   (445)  GPVGAGKSSLLSAVLGELAPSHGLVSVHGRIA----YVSQQPWVFSGTL
      hABCC1   (678)  GQVGCGKSSLLSALLAEMDKVEGHVAIKGSVA----YVPQQAWIQNDSL
      hABCC3   (661)  GPVGCGKSSLVSALLGEMEKLEGKVHMKGSVA----YVPQQAWIQNCTL
      hABCC2   (671)  GPVGSGKSSLISAMLGEMENVHGHITIKGTTA----YVPQQSWIQNGTI
      hABCC6   (663)  GPVGAGKSSLLSALLGELSKVEGFVSIEGAVA***YVPQEAWVQNTSV
      hABCC8   (713)  GQVGCGKSSLLLAALGEMQKVSGAVFWSSLPD***YASQKPWLLNATV
      hABCC9   (705)  GQVGCGKSSLLLAILGEMQTLEGKVHWSNVNE***YAAQKPWLLNATV
      hABCC10  (633)  GKVGCGKSSLLAAIAGELHRLRGHVAVRGLSKGFGLATQEPWIQFATI
      hABCC11  (544)  GNTGSGKSSLLSAILEEMHLLEGSVGVQGSLA----YVPQQAWIVSGNI
      hABCC12  (513)  GNVGSGKSSLLAALLGQMQLQKGVVAVNGTLA----YVSQQAWIFHGNV
       hABCC5  (595)  GSVGSGKTSLISAILGQMTLLEGSIAISGTFA----YVAQQAWIINATL

CHICKEN CFTR   (459)  GSTGSGKTSLLMLIMGELEPSEGKIKHSGRIS----FSPQVSWIMPGTI
  SHARK CFTR   (459)  GSTGSGKSSLLMMIMGELEPSDGKIKHSGRIS----YSPQVPWIMPGTI
ZEBRAFISH CFTR (457)  GSMGSGKSSLLMTIIGELVPSSGKIRHSGRIS----YSSQTAWIMPGTI
CONSENSUS             GxVGxGKSSLLxALLGEMxxxxGxYxxxGxxx     YxxQxxWLLxxxL
                                                                      └──┬──┘
                                                                       Q-LOOP HUMAN CFTR            KENIIFGVSYDEYRYRSVIKACQLEEDISKFAEKDNIVLGEGGITLSGGQRARIS
      hABCC4          RSNILFGKKYEKERYEKVIKACALKKDLQLLEDGDLTVIGDRGTTLSGGQKARVN
      hABCC1          RENILFGCQLEEPYYRSVIQACALLPDIEILPSGDRTEIGEKGVNLSGGQKQRVS
      hABCC3          QENVLFGKALNPKRYQQTLEACALLADLEMLPGGDQTEIGEKGINLSGGQRQRVS
      hABCC2          KDNILFGTEFNEKRYQQVLEACALLPDIFMLPGGDLAEIGEKGINLSGGQKQRIS
      hABCC6          VENVCFGQELDPPWLERVLEACALQPDVDSFPEGIHTSIGEQGMNLSGGQKQRLS
      hABCC8          EENIIFESPFNKQRYKMVIEACSLQPDIDILPHGDQTQIGERGINLSGGQRQRIS
      hABCC9          EENITFGSPFNKQRYKAVTDACSLQPDIDLLPFGDQTEIGERGINLSGGQRQRIC
      hABCC10         RDNILFGKTFDAQLYKEVLEACALNDDLSILPAGDQTEVGEKGVTLSGGQRARIA
      hABCC11         RENILMGGAYDKARYLQVLHCCSLNRDIELLPFGDMTEIGERGLNLSGGQKQRIS
      hABCC12         RENILFGEKYDHQRYQHTVRVCGLQKDLSNLPYGDLTEIGERGLNLSGGQRQRIS
       hABCC5         RDNILFGKEYDEERYNSVLNSCCLRPDIAILPSSDLTEIGERGANLSGGQRQRIS CHICKEN CFTR          KENIIFGVSYDEYKYKSVIQACQLEEDIIKFPDKDYTVLGEGGIILSGGQRARIS
  SHARK CFTR          KDNIIFGLSYDEYKYTSVVNACQLEEDITVFPNKDTVLGDGGITLSGGQRARIS
ZEBRAFISH CFTR        RDNILFGLTYDEYKYKSVVKACQLEEDIAALPEKDKTPMAEGGLNLSGGQKARVA
CONSENSUS             xxNLxFG.xxxxxYxxVxxACxLxxDxxLPxGDxTxIGExGxNLSGGQxQRIx
                                                     └────┬────┘└───┬────┘
                                                          SDR     SIGNATURE
```

FIG. 8

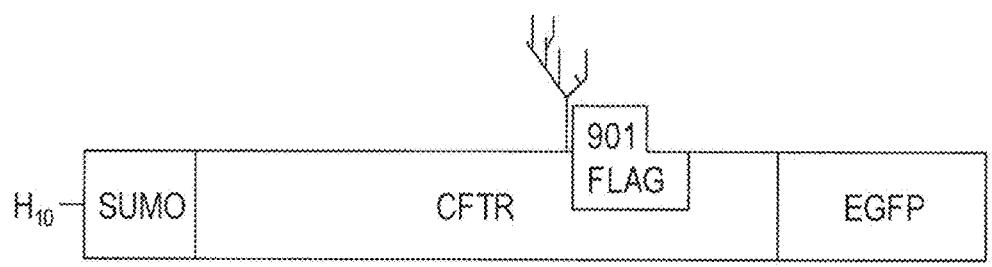
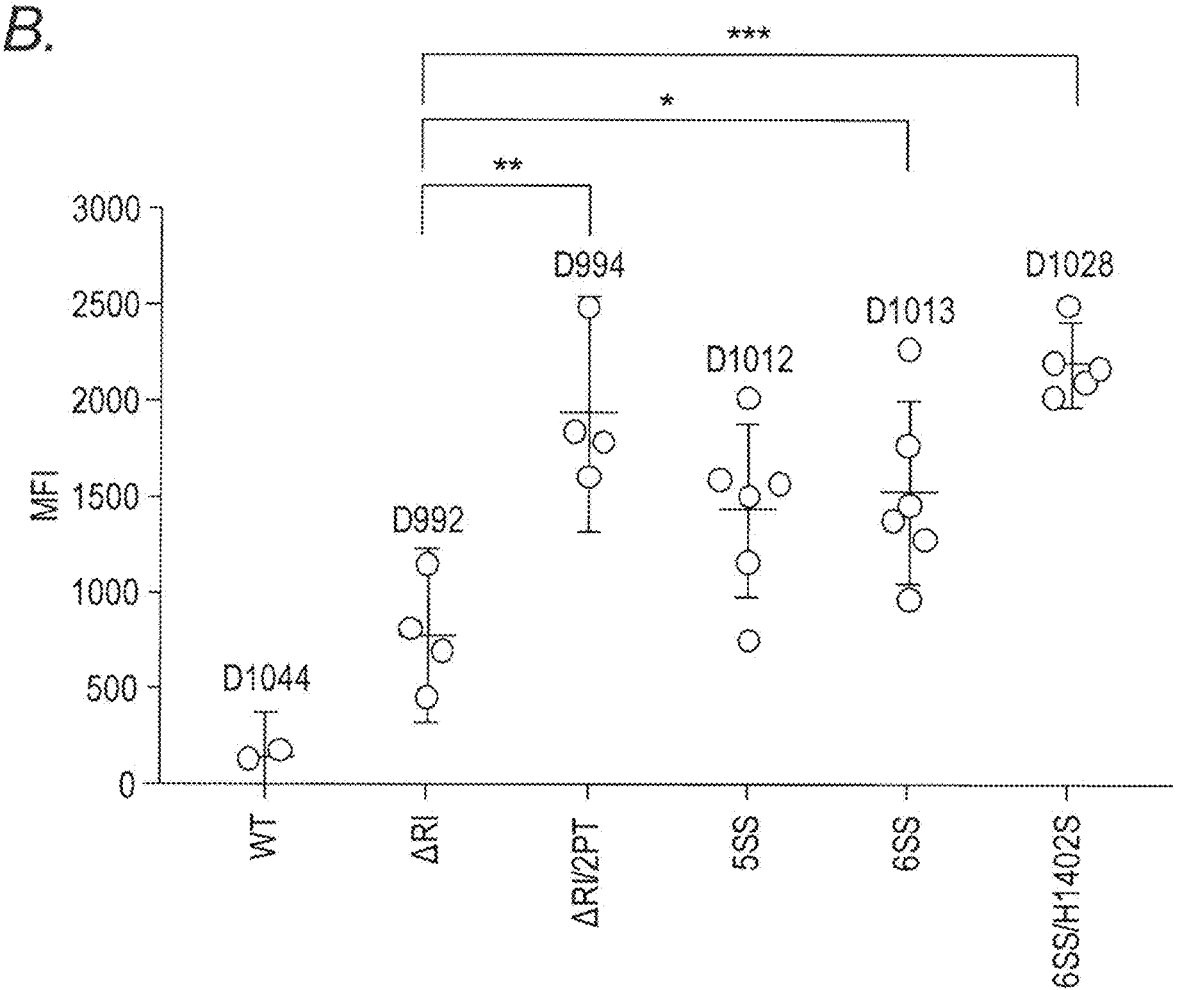
FIG. 10

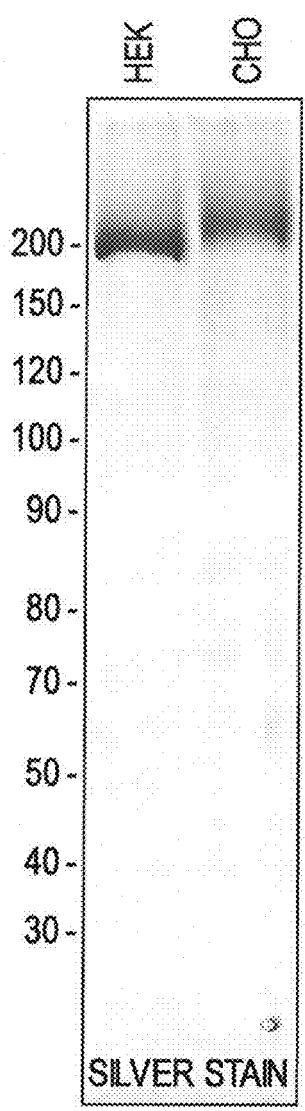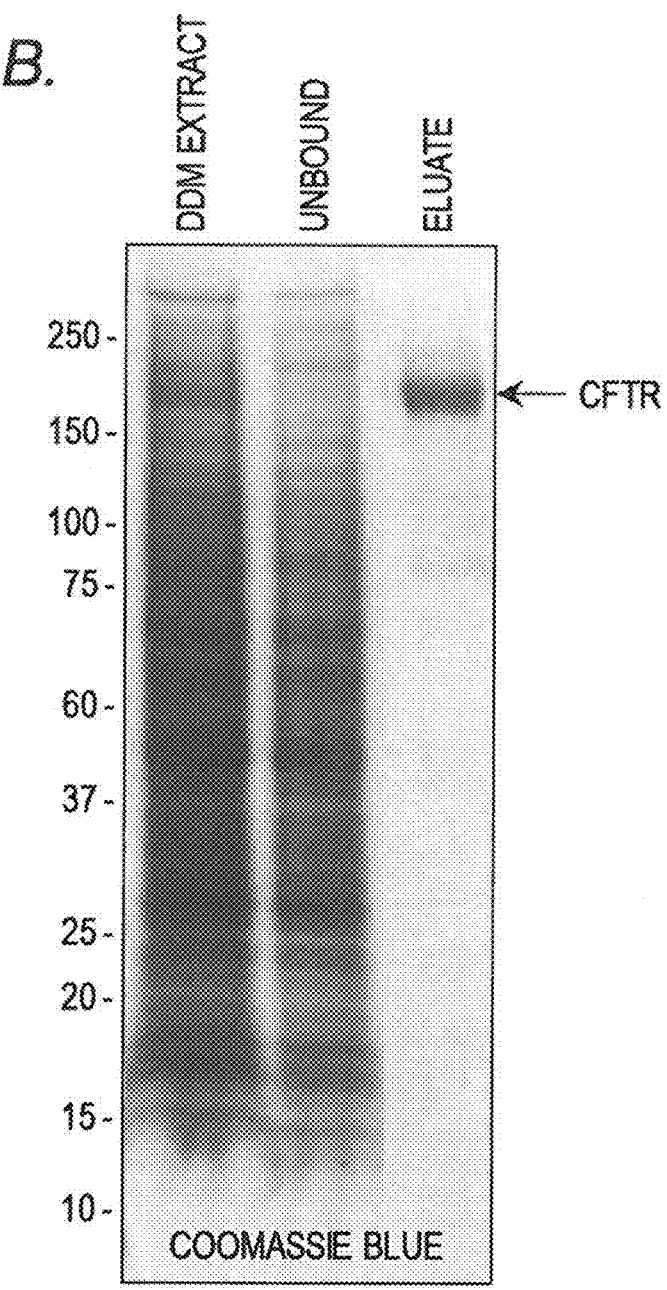
FIG. 12

MODIFIED CYSTIC FIBROSIS TRANSMEMBRANE CONDUCTANCE REGULATOR (CFTR) POLYPEPTIDES WITH INCREASED STABILITY AND USES THEREOF

STATEMENT OF PRIORITY

This application claims the benefit, under 35 U.S.C. § 119(e), of U.S. Provisional Application Ser. No. 62/631,364, filed Feb. 15, 2018, the entire contents of which are incorporated by reference herein.

STATEMENT REGARDING ELECTRONIC FILING OF A SEQUENCE LISTING

A Sequence Listing in ASCII text format, submitted under 37 C.F.R. § 1.821, entitled 5656-69_ST25.txt, 35,552 bytes in size, generated on Dec. 11, 2020 and filed via EFS-Web, is provided in lieu of a paper copy. This Sequence Listing is hereby incorporated herein by reference into the specification for its disclosure.

FIELD OF INVENTION

The invention relates to modified CFTR polypeptide or functional fragment thereof of the Cystic Fibrosis Transmembrane Conductance Regulator (CFTR) protein or fragment thereof comprising one or more amino acid mutations to enhance protein structural stability of the CFTR protein or fragment thereof and methods of making and using the same.

BACKGROUND

Cystic fibrosis (CF) is a recessive genetic disease that affects approximately 30,000 children and adults in the United States and approximately 30,000 children and adults in Europe. Despite progress in the treatment of CF, there is no cure. CF is caused by mutations in the cystic fibrosis transmembrane conductance regulator (CFTR) gene that encodes an epithelial chloride ion channel responsible for aiding in the regulation of salt and water absorption and secretion in various tissues. In epithelia cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking. The gene encoding CFTR has been identified and sequenced. Sequence analysis of the CFTR gene of CF chromosomes has revealed a variety of disease causing mutations. The most prevalent mutation is a deletion of phenylalanine at position 508 of the CFTR amino acid sequence, and is commonly referred to as ΔF508-CFTR. This mutation occurs in approximately 70% of the cases of cystic fibrosis and is associated with severe disease. It is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective ER processing of ABC transporters by the ER machinery has been shown to be the underlying basis not only for CF disease, but for a wide range of other isolated and inherited diseases.

Accordingly, there is a pressing need to better understand CFTR folding, structure and function to address how these are affected in patients with CF and related diseases.

INVENTION SUMMARY

The present invention is based, in part, on the development of modified CFTR polypeptides or functional fragments thereof that contain single or multiple amino acid mutations that are directed towards improving the structural stability of such CFTR polypeptides and/or functional fragments. The invention further relates to evaluating these modified CFTR polypeptides or functional fragments for their biological activity, such as ATPase activity, ion channel conductivity, and/or protein folding properties.

Accordingly, one aspect of the invention relates to a modified human cystic fibrosis transmembrane conductance regulator (CFTR) polypeptide or functional fragment thereof, wherein the polypeptide differs from the wild-type human CFTR protein (SEQ ID NO:1) or fragment thereof by the presence of four or more mutations selected from V150D, M470V, S492P, F494N, S495P, A534P, I539T, G550E, G551D, R553Q, R555K, Q637R, S1255L, K1334G, S1359A, E1371Q, H1402S, Q1411D, and any combination thereof, such that the stability of the polypeptide is increased relative to that of the wild-type human CFTR polypeptide or fragment thereof.

A second aspect of the invention relates to a modified human cystic fibrosis transmembrane conductance regulator (CFTR) polypeptide or functional fragment thereof, wherein the polypeptide differs from the wild-type human CFTR protein (SEQ ID NO.1) or fragment thereof by the presence of one, two, or three mutations selected from V150D, M470V, S492P, F494N, S495P, I539T, G550E, G551D, R553Q, R555K, Q637R, H1402S, E1371Q, and any combination thereof, such that the stability of the polypeptide is increased relative to that of the wild-type human CFTR polypeptide or fragment thereof.

A third aspect of the invention relates to a modified human CFTR polypeptide or functional fragment thereof, wherein the polypeptide composition differs from the wild-type human CFTR protein (SEQ ID NO:1) or fragment thereof by the presence of four or more mutations of amino acid residues located in the Helix 1, Q-loop, F508-loop, SDR loop, Helix 5 or a combination thereof of the polypeptide, such that the structural stability of the polypeptide is increased relative to that of the wild-type CFTR protein or fragment thereof.

A fourth aspect of the invention relates to a nucleic acid encoding the polypeptide or functional fragment of the invention, a vector comprising the nucleic acid of the invention, and a cell comprising the vector or nucleic acid of the invention.

A fifth aspect of the invention relates to a method of studying CFTR structure and/or function, comprising using the CFTR polypeptide of the invention or functional fragment thereof in the method.

BRIEF DESCRIPTION OF THE DRAWINGS

FIG. 3: Cellular maturation and activity of full-length CFTR with NBD1-stabilizing mutations. PANEL (A) Purified, phosphorylated WT CFTR and mutants were resolved by SDS-PAGE and silver stained. Insertion of the FLAG epitope at position 901 disrupts one of two glycosylation sites, and thus mature glycosylated (band C) and core glycosylated (band B, indicated by arrows) forms do separate but only poorly on a 7% polyacrylamide SDS-gel. PANEL (B) Purified proteins were supplemented with destabilized lipid, and ATP hydrolysis was measured at subsaturating 0.3 mM [$\alpha^{32}$P]-ATP. D359 is an HEK cell line expressing ΔRI-CFTR. Averages ± standard deviations of at least 3 experiments are shown.

FIG. 8: NBD1 alignments of human ABC-C transporters and selected CFTR orthologs. The flexible Q-loop plays an important role in ATP binding and interacts with transmembrane domains, the conserved Signature sequence is important for ATP binding, and the structurally diverse region (SDR) is divergent in CFTR compared to other human ABC-C subfamily members (shown from top to bottom: human CFTR [SEQ ID NO:4]; hABCC4 [SEQ ID NO:5]; hABCC1 [SEQ ID NO:6]; hABCC3 [SEQ ID NO:7]; hABCC2 [SEQ ID NO:8]; hABCC6 [SEQ ID NO:9], hABCC8 [SEQ ID NO:10], hABCC9 [SEQ ID NO:11]; hABCC10 [SEQ ID NO:12]; hABCC11 [SEQ ID NO:13]; hABCC12 [SEQ ID NO:14]; hABCC5 [SEQ ID NO:15]; chicken CFTR [SEQ ID NO:16]; shark CFTR [SEQ ID NO:17]; and zebrafish CFTR [SEQ ID NO:18]). S492P, A534P and I539T are 'back-to-consensus' mutations.

FIG. 10: Cell surface expression of engineered CFTR variants. PANEL (A) His$_{10}$-Sumo*CFTR$^{FLAG}$-EGFP expression construct showing the relative location of the $^{901}$Flag epitope in the 4$^{th}$ extracellular loop, and the N-terminal His$_{10}$-Sumo and C-terminal enhanced Green fluorescent protein (EGFP) tags. PANEL (B) Wild type and mutant full-length CFTR proteins, described in Table 3, were expressed in CHO cells. Surface CFTR was immunostained with antiFlag antibody and quantified by flow cytometry.

Mean fluorescent intensity (MFI) values of the cell population (represented by the ● symbol) are plotted for replicate experiments. D-numbers above the columns are lab designations for the cell lines. All mutants were built on the ΔRI-CFTR (Δ405-436) backbone (Table 3). One way Anova followed by Tukey's multiple comparisons test showed significant differences between ΔRI and either ΔRI/2PT, 6SS, and 6SS/H1402S CFTR (P<0.001 (**), p<0.05 (*), and p<0.0001 (***)), respectively.

Figure 11:
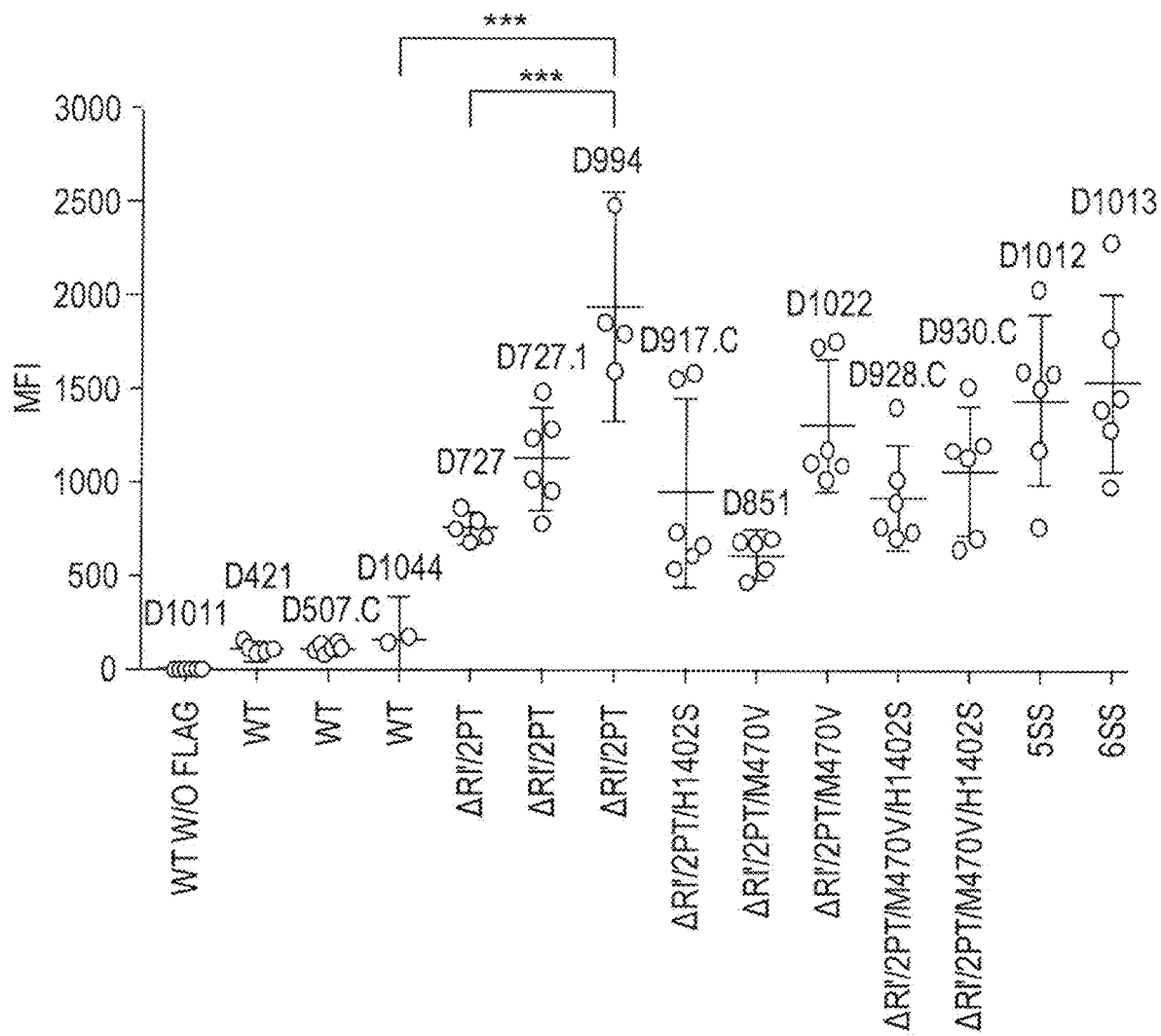

FIG. 11: Comparison of cell surface CFTR expression using different promotors and transcriptional activators. Surface expression of CFTR was measured by flow cytometry using antibody against an extracellular Flag epitope, and the mean fluorescence intensity (MFI) was plotted for cell populations in replicate experiments. Clonal cell lines have the "c" suffix. The WT construct in D1011 lacks the Flag epitope and serves as a negative immunostain control. ΔRI/2PT CFTR was expressed in three cell lines: (i) D727 under control of the doxycycline-inducible TRE-tight promoter carrying the conventional reverse tet repressor rtTA (parental cell line D389); (ii) D727.1 carrying 3G-matched rtTA transcription activators (parental cell line D896); and (iii) D994 under the control of second generation promoter TRE.2 (Table 3). Cell lines D851, D917c, D928c, and D930c all expressed CFTR mutations under the TRE-tight promoter with the conventional tet repressor (parental cell line D389). Statistical analyses were done as in FIG. 10.

FIG. 12: Purification of CFTR. PANEL (A) Human WT CFTR purified by dual affinity chromatography on Ni-NTA and anti-FLAG resin from HEK or CHO cells gives comparable purity and ATPase activity; these preparations are devoid of other contamination ATPase as apparent from the non-detectable activity of the H1402S mutation (less than 2% of WT CFTR), see FIG. 3 and Table 1. PANEL (B) Purification of 6SS/H1402S by a one-step affinity purification on anti-FLAG resin gives higher yields with little sacrifice in purity; approximately 41%+/−17% (n=39) of the CFTR is recovered from the membranes (see Table 3).

Figure 13:
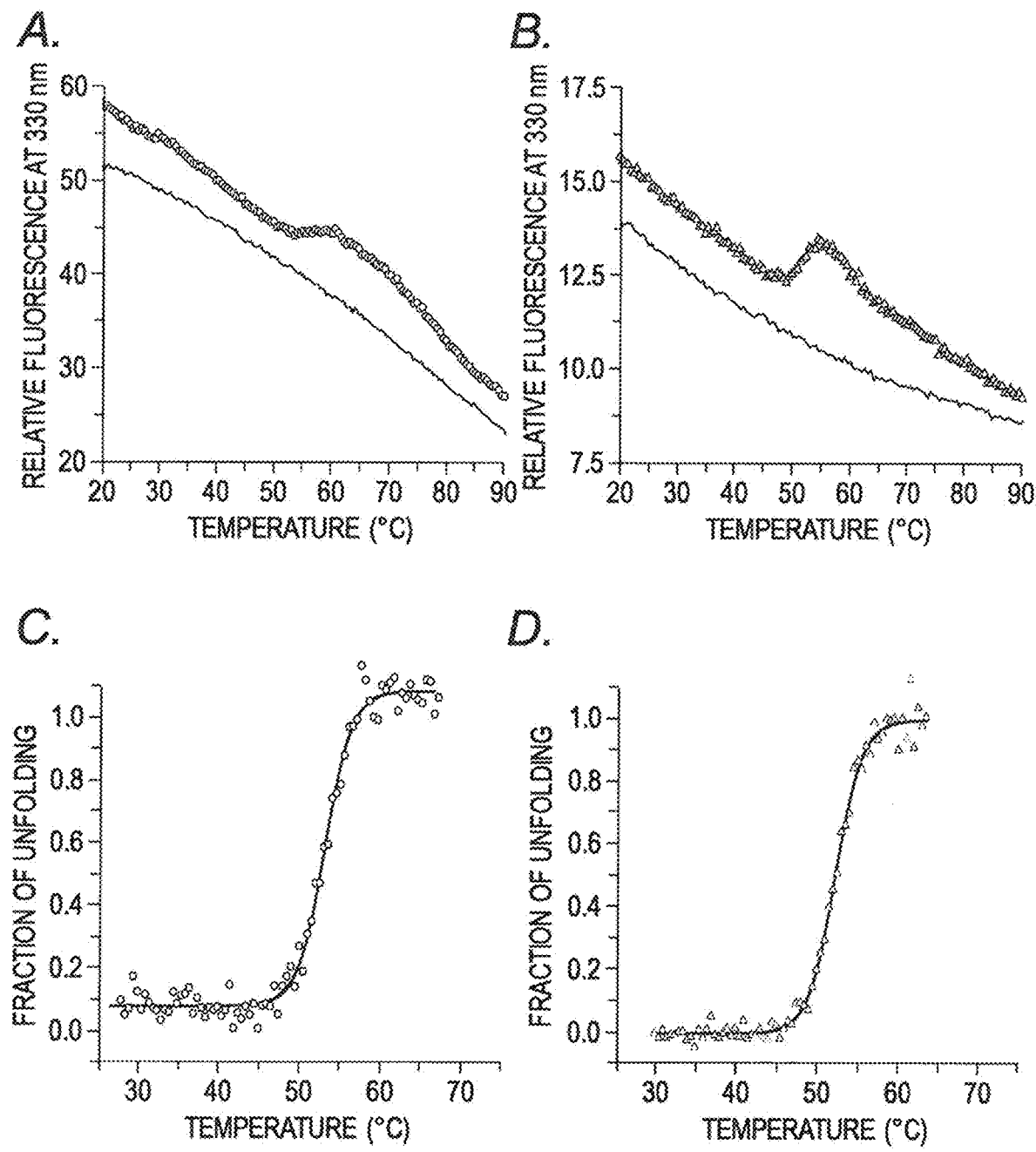

FIG. 13: Thermal unfolding of full-length CFTR. During controlled heating of ΔRI/2PT/M470V mutant, a gradual decrease in fluorescence was observed with increasing temperature, likely caused by thermal quenching, and with a single sigmoidal increase in fluorescence intensity; there was no change in $\lambda_{max}$. Subjecting the same sample to a second heating cycle produced the same steady negative slope but without the sigmoidal folding transition (solid line), indicating the unfolding was irreversible. PANEL (A) Intrinsic fluorescence (open circles) of CFTR mutant, ΔRI/2PT/M470V, as a function of temperature, scanned at 1° C./min. The dashed line is a rescan of the same sample. PANEL (B) Intrinsic fluorescence of ΔRI-NBD1 (open triangles) as a function of temperature, and the rescan (solid line). PANEL (C) The normalized fluorescence data for ΔRI/2PT/M470V (open circles) was fitted by a sigmoidal function (solid line) to determine the transition midpoint, i.e. the unfolding $T_m^{trp}$. PANEL (D) Normalized fluorescence data (open triangles) and sigmoidal fit (solid line) for ΔRI-NBD1.

Figure 14:
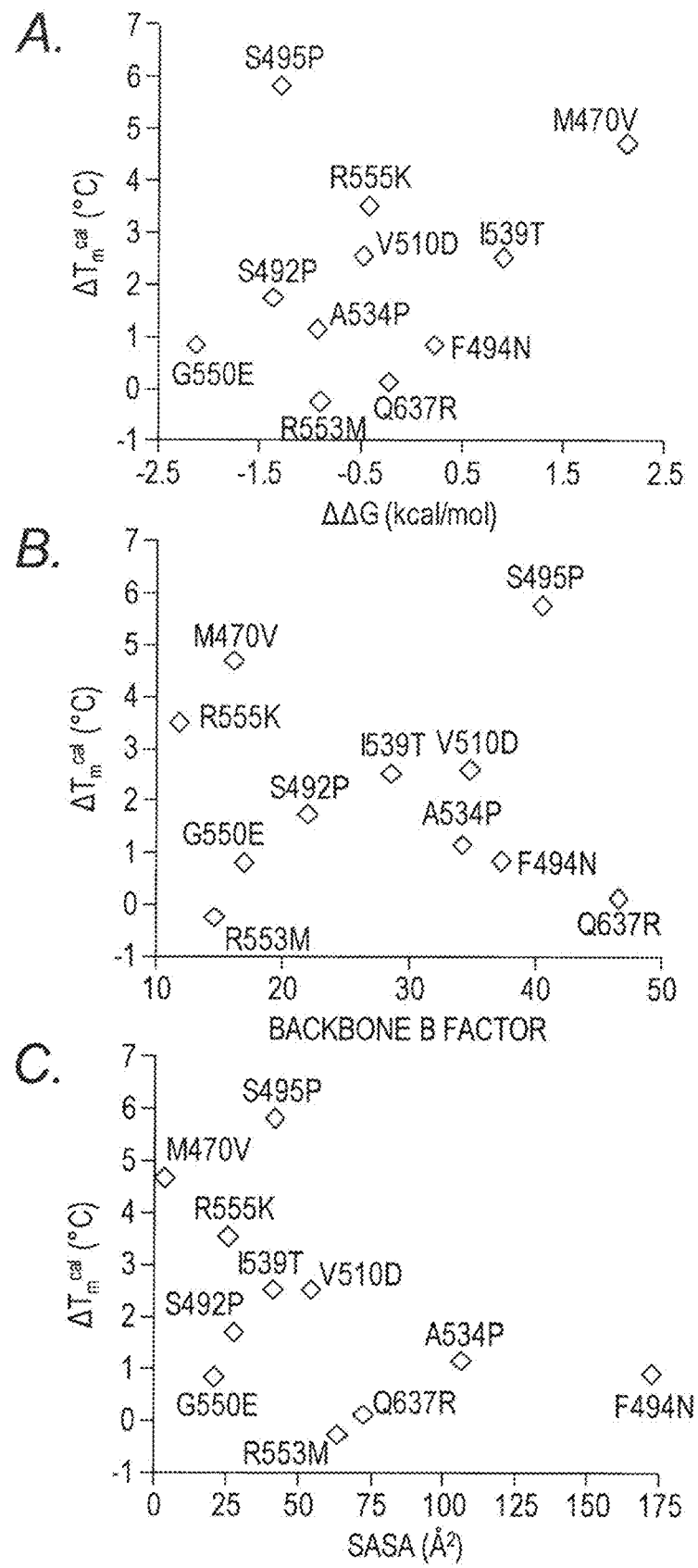

FIG. 14: Correlations of NBD1 $T_m^{cal}$-shifts with structural parameters.

Figure 15:
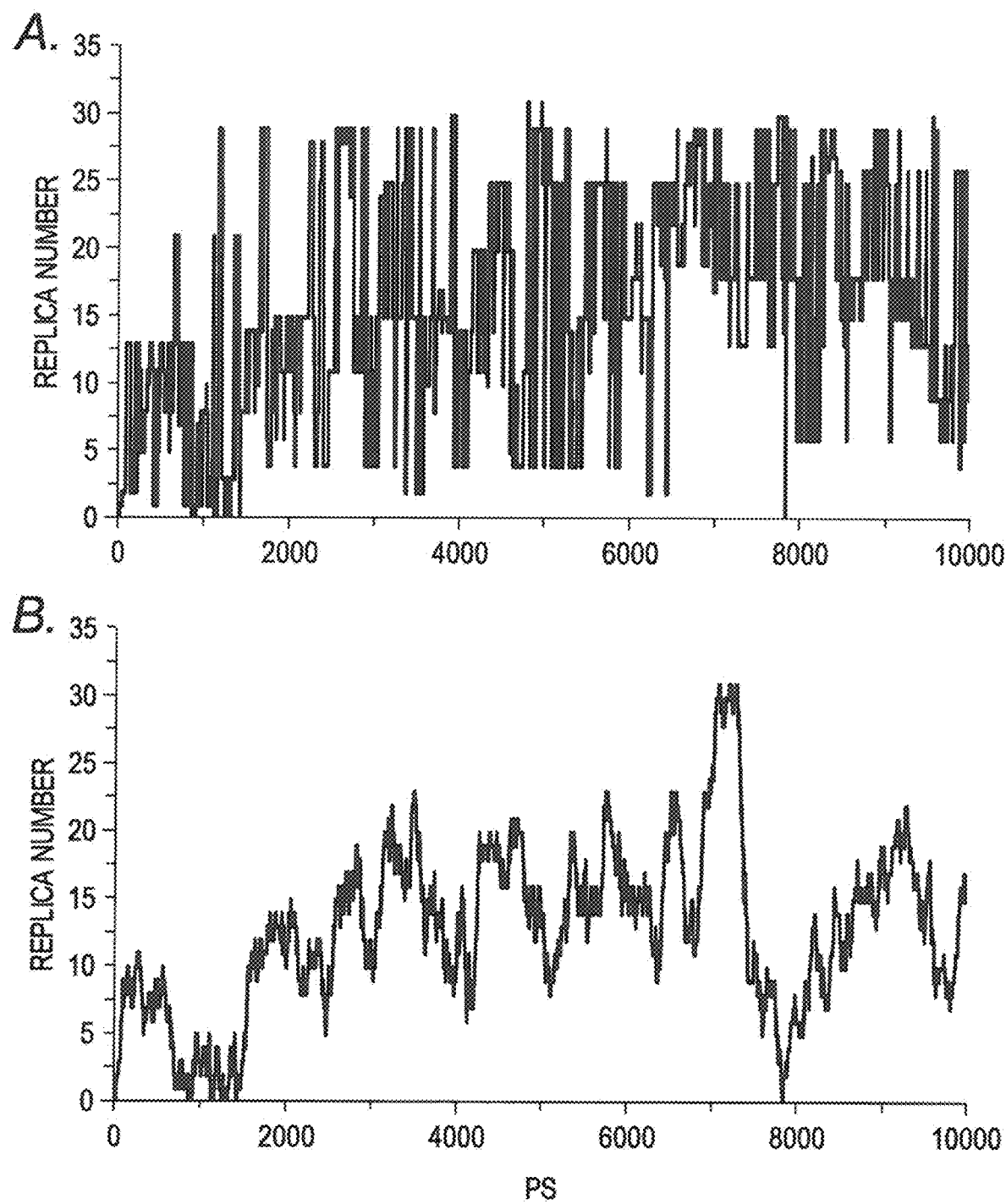

FIG. 15: Ground state replicas contribution and round trip for 6SS-NBD1. PANEL (A) Contribution of replicas to the analyzed, lowest temperature trajectory. PANEL (B) Progress of the lowest temperature replica throughout the simulation.

Figure 16:
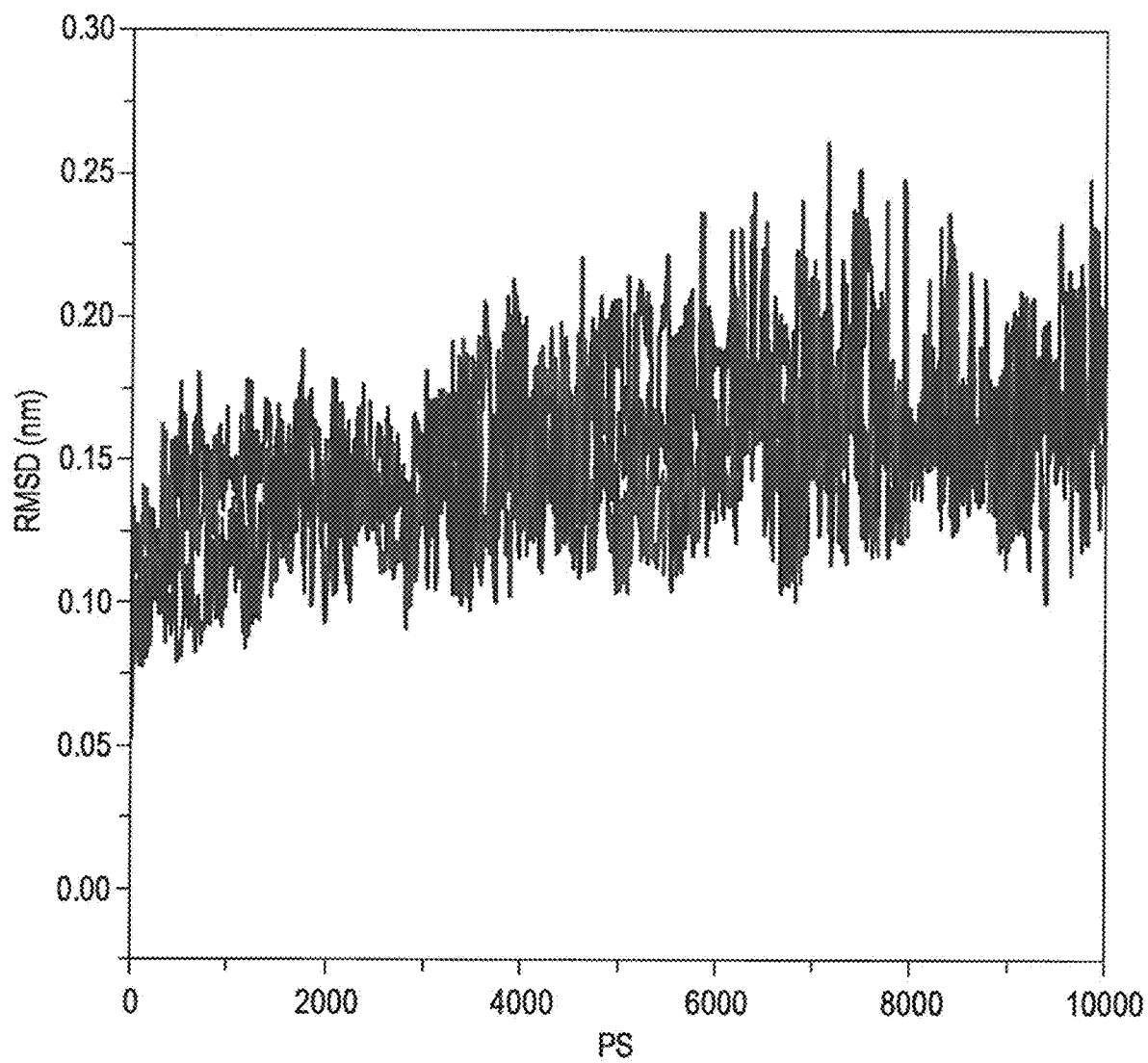

FIG. 16: RMSD profiles of 6SS-NBD1. The average RMSD (three repeats) over all simulations, relative to the crystal structure, was 1.6±0.3 Å.

DETAILED DESCRIPTION

The present invention will now be described in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. In addition, any references cited herein are incorporated by reference in their entireties.

Unless otherwise defined, all technical and scientific terms used herein have the same meaning as commonly understood by one of skill in the art to which this invention belongs. The terminology used in the description of the invention herein is for the purpose of describing particular embodiments only and is not intended to be limiting of the invention. All publications, patent applications, patents, patent publications and other references cited herein are incorporated by reference in their entireties for the teachings relevant to the sentence and/or paragraph in which the reference is presented.

Amino acids are represented herein in the manner recommended by the IUPAC-IUB Biochemical Nomenclature Commission, or (for amino acids) by either the one-letter code, or the three letter code, both in accordance with 37 C.F.R. § 1.822 and established usage.

Except as otherwise indicated, standard methods known to those skilled in the art may be used for cloning genes, amplifying and detecting nucleic acids, and the like. Such techniques are known to those skilled in the art. See, e.g., Sambrook et al., Molecular Cloning: A Laboratory Manual 2nd Ed. (Cold Spring Harbor, N.Y., 1989); Ausubel et al. Current Protocols in Molecular Biology (Green Publishing Associates, Inc. and John Wiley & Sons, Inc., New York).

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate, if the specification states that a complex comprises components A, B and C, it is specifically intended that any of A, B or C, or a combination thereof, can be omitted and disclaimed singularly or in any combination.

As used in the description of the invention and the appended claims, the singular forms "a," "an," and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of polypeptide, dose, time, temperature, enzymatic activity or other biological activity and the like, is meant to encompass variations of ±10%, ±5%, ±1%, ±0.5%, or even ±0.1% of the specified amount.

As used herein, the transitional phrase "consisting essentially of" (and grammatical variants) is to be interpreted as encompassing the recited materials or steps and those that do not materially affect the basic and novel characteristic(s) of the claimed invention. Thus, the term "consisting essentially of" as used herein should not be interpreted as equivalent to "comprising."

The term "consists essentially of" (and grammatical variants), as applied to a polypeptide or polynucleotide sequence of this invention, means a polypeptide or polynucleotide that consists of both the recited sequence (e.g., SEQ ID NO) and a total of ten or less (e.g., 1, 2, 3, 4, 5, 6, 7, 8, 9, or 10) additional amino acids on the N-terminal and/or C-terminal ends of the recited sequence or additional nucleotides on the 5' and/or 3' ends of the recited sequence such that the function of the polypeptide or polynucleotide is not materially altered. The total of ten or less additional amino acids or nucleotides includes the total number of additional amino acids or nucleotides on both ends added together. The term "materially altered," as applied to polypeptides of the invention, refers to an increase or decrease in biological activities/properties (e.g., ATPase activity, ion channel conductivity, and/or protein folding/stability) of at least about 50% or more as compared to the activity of a polypeptide consisting of the recited sequence.

The term "modulate," "modulates," or "modulation" refers to enhancement (e.g., an increase) or inhibition (e.g., a decrease) in the specified level or activity.

The term "enhance" or "increase" refers to an increase in the specified parameter of at least about 1.25-fold, 1.5-fold, 2-fold, 3-fold, 4-fold, 5-fold, 6-fold, 8-fold, 10-fold, twelve-fold, or even fifteen-fold and/or can be expressed in the enhancement and/or increase of a specified level and/or activity of at least about 1%, 5%, 10%, 15%, 25%, 35%, 40%, 50%, 60%, 75%, 80%, 90%, 95% or more The term "inhibit" or "reduce" or grammatical variations thereof as used herein refers to a decrease or diminishment in the specified level or activity of at least about 1, 5, 10, 15%, 25%, 35%, 40%, 50%, 60%, 75%, 80%, 90%, 95% or more. In particular embodiments, the inhibition or reduction results in little or essentially no detectible activity (at most, an insignificant amount, e.g., less than about 10% or even 5%).

The term "contact" or grammatical variations thereof as used with respect to a polypeptide and a receptor, refers to bringing the polypeptide and the receptor in sufficiently close proximity to each other for one to exert a biological effect on the other. In some embodiments, the term contact means binding of the polypeptide to the receptor.

The term "fragment," as applied to a peptide, will be understood to mean an amino acid sequence of reduced length relative to a reference peptide (e.g., WT CFTR protein) or amino acid sequence (e.g., NBD1 domain) and comprising, consisting essentially of, and/or consisting of an amino acid sequence of contiguous amino acids identical to the reference peptide or amino acid sequence. Such a peptide fragment according to the invention may be, where appropriate, included in a larger polypeptide of which it is a constituent. In some embodiments, such fragments can comprise, consist essentially of, and/or consist of peptides having a length of at least about 5, 10, 15, 20, 25, 30, 35, 46. 50, 55, 60, 65, 70, 75, 80, 85, 90, 95 or 100 or more consecutive amino acids of a peptide or amino acid sequence according to the invention.

As used herein, the terms "nucleic acid" or "nucleic acid molecule" encompass both RNA and DNA, including cDNA, genomic DNA, synthetic (e.g., chemically synthesized) DNA and chimeras of RNA and DNA. The nucleic acid molecule may be double-stranded or single-stranded. The nucleic acid molecule may be synthesized using nucleotide analogs or derivatives (e.g., inosine or phosphorothioate nucleotides). Such nucleotides can be used, for example, to prepare nucleic acid molecules that have altered base-pairing abilities or increased resistance to nucleases.

As used herein, the term "polypeptide" encompasses both peptides and proteins (including fusion proteins), unless indicated otherwise.

A "fusion protein" is a polypeptide produced when two heterologous nucleotide sequences or fragments thereof coding for two (or more) different polypeptides not found fused together in nature are fused together in the correct translational reading frame. Illustrative fusion polypeptides include fusions of a peptide of the invention (or a fragment thereof) to all or a portion of glutathione-S-transferase, maltose-binding protein, or a reporter protein (e.g., Green Fluorescent Protein, β-glucuronidase, β-galactosidase, luciferase, etc.), hemagglutinin, c-myc, FLAG epitope, etc.

A "recombinant" nucleic acid, polynucleotide or nucleotide sequence is one produced by genetic engineering techniques.

A "recombinant" polypeptide is produced from a recombinant nucleic acid, polypeptide or nucleotide sequence.

As used herein, a "functional" polypeptide or "functional fragment" is one that substantially retains at least one biological activity normally associated with that polypeptide (e.g., WT CFTR protein or fragment thereof). In particular embodiments, the "functional" polypeptide or "functional fragment" substantially retains all of the activities possessed by the unmodified polypeptide (e.g., WT CFTR protein or fragment thereof). By "substantially retains" biological activity, it is meant that the polypeptide retains at least about 20%, 30%, 40%, 50%, 60%, 75%, 85%, 90%, 95%, 97%, 98%, 99%, or more, of the biological activity of the native polypeptide (and can even have a higher level of activity than the native polypeptide). A "non-functional" polypeptide is one that exhibits little or essentially no detectable biological activity normally associated with the polypeptide (e.g., at most, only an insignificant amount, e.g., less than about 10% or even 5%). Biological activities such as ATPase activity, ion channel conductivity, and/or protein folding can be measured using assays that are well known in the art and as described herein.

As used herein, the term "host cell" refers to a cell that is engineered to express the recombinant modified CFTR polypeptide or functional fragment thereof (e.g., full length CFTR protein or a fragment thereof, such as the NBD1 domain). "Host cell" refers not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, an "isolated" polynucleotide (e.g., an "isolated nucleic acid" or an "isolated nucleotide sequence") means a polynucleotide at least partially separated from at least some of the other components of the naturally occurring organism or virus, for example, the cell or viral structural components or other polypeptides or nucleic acids commonly found associated with the polynucleotide. Optionally, but not necessarily, the "isolated" polynucleotide is present at a greater concentration (i.e., is enriched) as compared with the starting material (e.g., at least about a two-fold, three-fold, four-fold, ten-fold, twenty-fold, fifty-fold, one-hundred-fold, five-hundred-fold, one thousand-fold, ten thousand-fold or greater concentration). In representative embodiments, the isolated polynucleotide is at least about 1%, 5%, 10%, 20%, 30%, 40%, 50%, 60%, 70%, 80%, 90%, 95% or more pure.

An "isolated" polypeptide means a polypeptide that is at least partially separated from at least some of the other components of the naturally occurring organism or virus, for example, the cell or viral structural components or other polypeptides or nucleic acids commonly found associated with the polypeptide. Optionally, but not necessarily, the "isolated" polypeptide is present at a greater concentration (i.e., is enriched) as compared with the starting material (e.g., at least about a two-fold, three-fold, four-fold, ten-fold, twenty-fold, fifty-fold, one-hundred-fold, five-hundred-fold, one thousand-fold, ten thousand-fold or greater concentration). In representative embodiments, the isolated polypeptide is at least about 1%, 5%, 10%, 20%, 30%, 40%, 50%, 60%, 70%, 80%, 90%, 95% or more pure.

The terms "polynucleotide", "nucleic acid" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example, those described in Current Protocols in Molecular Biology (Ausubel et al., eds. 1987) Supplement 30, section 7.7.18, Table 7.7.1. Preferably, default parameters are used for alignment. One alignment program is BLAST, using default parameters. Examples of the programs include BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, and viruses (bacteriophage, animal viruses, and plant viruses)

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infrHost cells may be derived from prokaryotes or eukaryotes, depending upon whether the desired result is replication of the vector or expression of part or all of the vector-encoded nucleic acid sequences. Prokaryotes include gram negative or positive cells. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLO-PACK™ Gold Cells (STRATAGENE®, La Jolla). Alternatively, bacterial cells such as E. coli LE392 could be used as host cells for phage viruses.

CFTR functions as a chloride- and bicarbonate-selective ion channel in the plasma membrane (J. R. Riordan, et al., Science 245 (1989) 1066-1073; D. N. Sheppard, et al., Physiol. Rev. 79 (1999) S23-45; J. R. Riordan, et al., Annu. Rev. Biochem. 77 (2008) 701-726). Genetic defects in CFTR cause cystic fibrosis (CF), a life-threatening disease manifested by dysregulation of epithelial fluid in the lungs, pancreas and other organs. More than 2000 mutations have been reported in the CFTR gene, of which at least 280 mutations are confirmed to cause the disease (P. R. Sosnay, et al., Nat. Genet. 45 (2013) 1160-1167). Depending on location within the CFTR gene, disease-causing mutations vary in severity, and have been categorized into six classes according to their phenotypes in reducing protein expression, function, and/or stability (M. D. Amaral, et al., Curr. Pharm. Des. 19 (2013) 3497-3508; B. S. Quon, et al., BMJ 352 (2016) i859; G. Veit, et al., Mol. Biol. Cell 27 (2016) 424-433).

Personalized medicine treating a CF patient's underlying defect has become a high priority, and is actively endorsed by the Cystic Fibrosis Foundation (B. S. Quon, et al., Can.

Respir. J. 22 (2015) 257-260). A prominent success is the recently FDA-approved channel potentiator ivacaftor (Kalydeco, VX-770), that improves channel activity in G551D and other gating mutations (about 8% of the patient population) (B. S. Quon, et al., BMJ 352 (2016) i859; G. Veit, et al., Mol. Biol. Cell 27 (2016) 424-433; C; Sheridan, et al., Nat. Biotechnol. 29 (2011) 465-466; S. L. Martiniano, et al., Curr. Opin. Pediatr. 28 (3) (2016) 312-317). Yet the majority of patients still have few treatment options. The most prevalent disease-causing mutation is a single amino acid deletion, ΔF508, of which at least one allele is found in 85-90% of CF patients (P. R. Sosnay, et al., Nat. Genet. 45 (2013) 1160-1167). ΔF508 severely compromises CFTR folding, thus resulting in faulty maturation, poor localization to the cell surface, and reduced channel function by the few molecules which do reach the cell surface (G. L. Lukacs, et al., Trends Mol. Med. 18 (2012) 81-91; K. Du, et al., Nat. Struct. Mol. Biol. 12 (2005) 17-25). Recently tested combination therapies for patients with ΔF508-CFTR that target these multiple defects (Orkambi, or three next-generation CFTR modulator therapies with ivacaftor and tezacaftor (VX-661)) improved function by only a modest 3-15% (W. Zhang, et al., Drugs Today (Barc) 52 (2016) 229-237; E. K. Schneider, et al., Clin. Pharmacol. Ther. 101 (2017) 130-141). Thus, there is a pressing need to better understand CFTR folding, structure and function, not only to address how these are affected in patients with CF, but also to comprehend the effects of potential drug candidates.

CFTR is an atypical ATP-binding cassette (ABC) transporter with two transmembrane domains that harbor the ion channel, and two non-identical nucleotide binding domains (NBD1 and NBD2) that bind and hydrolyze ATP to gate the channel; gating is regulated by phosphorylation of a unique R-region (D. N. Sheppard, et al., Physiol. Rev. 79 (1999) S23-45; J. R. Riordan, et al., Annu. Rev. Biochem. 77 (2008) 701-726; D. C. Gadsby, et al., Nature 440 (2006) 477-483). Complex folding and domain assembly are limiting steps in the biogenesis and trafficking of CFTR (S. J. Kim, et al., Front. Pharmacol. 3 (2012) 201), and these are compromised by many CF-causing mutations such as ΔF508 in NBD1, resulting in protein misfolding and degradation by cellular quality control systems (G. L. Lukacs, et al., Trends Mol. Med. 18 (2012) 81-91). Due to intensive efforts to understand the consequences of F508 deletion, high resolution X-ray structures of bacterially expressed isolated NBD1 domain have been solved for wild-type (WT) and ΔF508 mutants from human and mouse (H. A. Lewis, et al., EMBO J. 23 (2004) 282-293; H. A. Lewis, et al., J. Biol. Chem. 280 (2005) 1346-1353; S. Atwell, et al., Protein Eng. Des. Sel. 23 (2010) 375-384; H. A. Lewis, et al., J. Mol. Biol. 396 (2010) 406-430). While ΔF508 alters NBD1 structure very little, it severely affects the folding kinetics, biogenesis, and the stability and dynamics of the domain (C. Wang, et al., Protein Sci. 19 (2010) 1932-1947; I. Protasevich, et al., Protein Sci. 19 (2010) 1917-1931; P. H. Thibodeau, et al., J. Biol. Chem. 285 (2010) 35825-35835; R. P. Hudson, et al., J. Biol. Chem. 287 (2012) 28480-28494; M. Zhenin, et al., J. Chem. Inf. Model. 55 (2015) 2349-2364). F508 is situated on the surface of NBD1 near the interface with the intracellular loops (ICLs) that connect to the transmembrane helices. This interfacial position, akin to a ball and socket joint, further complicates the folding and stability of NBD1 when in the context of the full-length protein, and may explain why a single amino acid deletion causes multiple defects that ultimately lead to defective CFTR biogenesis and compromised function at the cell surface (G. L. Lukacs, et al., Trends Mol. Med. 18 (2012) 81-91; S. J. Kim, et al., Front. Pharmacol. 3 (2012) 201; P. H. Thibodeau, et al., J. Biol. Chem. 285 (2010) 35825-35835; J. L. Mendoza, et al., Cell 148 (2012) 164-174; W. M. Rabeh, et al., Cell 148 (2012) 150-163).

Recently, the first structures of full-length CFTR from human and zebrafish (55% sequence identity to human) in a dephosphorylated, inactive state have been solved by cryo-electron microscopy (cryo-EM) at a nominal resolution of 3.7 to 3.9 Å (PDB 5uar, 5uak) (Z. Zhang, et al., Cell 167 (2016) 1586-1597 (e1589); F. Liu, et al., Cell 169 (2017) 85-95 (e88)). These structures revealed details of the transmembrane α-helical domains and the channel forming pore, with NBD1 and NBD2 widely separated and intercalated by portions of the regulatory R-region; but structures of the NBDs were of low resolution and most of the R-region, the regulatory insertion (RI), the fourth extracellular loop and the C-terminus could not be assigned, perhaps due to their disordered nature. A subsequent 3.4 Å resolution structure of phosphorylated zebrafish CFTR showed two well-ordered NBDs in an asymmetric sandwich dimer conformation with two bound, non-hydrolyzed ATP molecules, with the channel open to the cytoplasm and the extracellular gate closed (PDB 5W81) (Z. Zhang, et al., Cell 170 (2017) 483-491.e488). The structure revealed insights into the gating mechanism and likely presents a "pre-open" closed channel state (J. Zhang, et al., J. Gen. Physiol. 149 (2017) 355-372; W. Y. Lin, et al., Mol. Pharmacol. 90 (2016) 275-285). Despite these recent breakthroughs, higher resolution structures of human WT CFTR and of CFTR with at least some of the CF-causing mutations, and in conformationally distinct functional states, are still needed to better reveal the underlying structural defect for the many types of disease-causing mutations, and to advance therapeutic strategies. For such studies, it will be critical to have accompanying biochemical and biophysical evidence of perturbations caused by the different mutant theratypes. A stable and monodisperse protein is the key to higher resolution structures whether by cryo-EM or crystallography, and also for biochemical and biophysical studies to probe the energetics, dynamics and mechanism of action that cannot be revealed by structure alone. However, the low stability of CFTR in detergent solution, and even more so ΔF508-CFTR and other folding mutations, has impeded progress (X. Meng, et al., Cell. Mol. Life Sci. 74 (2017) 23-38).

A validated approach to improve CFTR stability comes from the body of literature describing 'second site' mutations of ΔF508-CFTR (X. Liu, et al., Biochemistry 51 (2012) 5113-5124; L. He, et al., J. Mol. Biol. 427 (2015) 106-120; Z. Xu, et al., J. Physiol. 592 (2014) 1931-1947). Those studies utilized sequence alignments and yeast screens of chimeric ABC transporters to identify mutations in NBD1 that rescued biogenesis of full-length ΔF508-CFTR (J. L. Teem, et al., Receptors Channels 4 (1996) 63-72; J. L. Teem, et al., Cell 73 (1993) 335-346; A. C. DeCarvalho, et al., J. Biol. Chem. 277 (2002) 35896-35905; L. He, et al., FASEB J. 24 (2010) 3103-3112; A. A. Aleksandrov, et al., J. Mol. Biol. 419 (2012) 41-60). Structural and biophysical studies of NBD1 domain constructs containing strategic mutations improved F508- and ΔF508-NBD1 solution properties and thermal stability (H. A. Lewis, et al., J. Biol. Chem. 280 (2005) 1346-1353; S. Atwell, et al., Protein Eng. Des. Sel. 23 (2010) 375-384; H. A. Lewis, et al., J. Mol. Biol. 396 (2010) 406-430). It was further demonstrated that certain of these ΔF508-stabilizing mutations increased biogenesis of WT CFTR in mammalian cells (W. M. Rabeh, et al., Cell 148 (2012) 150-163; L. S. Pissarra, et al., Chem. Biol. 15 (2008) 62-69), and some improved thermal stability of CFTR channel function (L. He, et al., J. Mol. Biol. 427 (2015) 106-120; L. A. Aleksandrov, et al., Protein Expr. Purif. 116 (2015) 159-166). Several recent reports have shown that select mutations which thermostabilized NBD1 also enhanced thermal stability of purified CFTR (L. A. Aleksandrov, et al., Protein Expr. Purif 116 (2015) 159-166; Z. Yang, et al., Pediatr. Pulmonol. 51 (2016) 218; I. L. Urbatsch, et al., Pediatr. Pulmonol. 51 (2016) 197; L. He, et al., Pediatr. Pulmonol. 51 (2016) 197; E. Hildebrandt, et al., Biochim. Biophys. Acta Biomembr. 1859 (2017) 289-293. From these cited studies, a tacit correlation has emerged suggesting that mutations that enhance NBD1 domain structural stability will also improve the structural stability of the full length CFTR.

In order to broaden the utility of this implicit correlation, the inventors have conducted a systematic analysis of NBD1 stabilization by a panel of mutations, singly or in combinations. The inventors then investigated their consequences on the stability of purified full-length CFTR. Two hypotheses were tested: 1) that specific combinations of single substitutions can be identified which will cumulatively yield an NBD1 domain with highly improved structural stability; and 2) that stabilizing NBD1 in full-length CFTR will enhance structural stability of purified CFTR in detergent solution. The study serves the overarching goal of producing full-length CFTR proteins with highly improved structural stability. Stabilized human CFTR may be valuable for biophysical and structural studies that advance CF drug development, and future mechanistic and structural studies of rare CF-causing mutations.

Accordingly, one aspect of the invention relates to a modified human CFTR polypeptide or functional fragment thereof, wherein the polypeptide composition from the wild-type human CFTR protein (SEQ ID NO:1) or fragment thereof by the presence of four or more mutations of amino acid residues located in the Helix 1, Q-loop, F508-loop, SDR loop, Helix 5 or a combination thereof of the polypeptide, such that the structural stability of the polypeptide is increased relative to that of the wild-type CFTR protein or fragment thereof. In some embodiments, the four or more mutations of amino acid residues are located in the Helix 1 of the modified CFTR polypeptide. In some embodiments, the four or more mutations of amino acid residues are present in the Q-loop of the modified CFTR polypeptide. In some embodiments, the four or more mutations of amino acid residues are present in the SDR loop of the modified CFTR polypeptide. In some embodiments, the four or more mutations of amino acid residues are present in the F508-loop of the modified CFTR polypeptide. In some embodiments, the four or more mutations of amino acid residues are present in the SDR-loop, Q-loop and the Helix 5 of the modified CFTR polypeptide. In some embodiments, the four or more mutations are present in the SDR loop, Helix 1, and Q-loop of the modified CFTR polypeptide.

Accordingly, another aspect of the invention relates to mutations of one or more specific amino acid residues in these named locations of the modified CFTR polypeptide or functional fragment thereof. Thus, some embodiments of the invention relate to a modified CFTR polypeptide or functional fragment thereof of a wild-type CFTR protein (SEQ ID NO:1) or fragment thereof, wherein the polypeptide or functional fragment thereof differs from the wild-type CFTR protein (SEQ ID NO:1) or fragment thereof by the presence of four or more mutations selected from V150D, M470V, S492P, F494N, S495P, A534P, I539T, G550E, G551D, R553Q, R555K, Q637R, S1255L, K1334G, S1359A, E1371Q, H1402S, Q1411D, and any combination thereof, such that the stability of the polypeptide is increased relative to that of the wild-type human CFTR polypeptide or fragment thereof. In some embodiments, the polypeptide or functional fragment of the invention comprises five or more mutations. In some embodiments, the polypeptide or functional fragment of the invention comprises six or more mutations. In some embodiments, the polypeptide or functional fragment of the invention comprises seven or more mutations. In some embodiments, the four or more mutations are selected from S492P, F494N, S495P, A534P, I539T, G550E, R555K, S1255L, K1334G, S1359A, Q1411D and any combination thereof. In some embodiments, the four or more mutations are selected from S492P, F494N, S495P, A534P, I539T, G550E, R555K, S1359A, and any combination thereof. In some embodiments, the four or more mutations are selected from S492P, F494N, S495P, A534P, I539T, G550E, R555K, and any combination thereof. In some embodiments, the four or more mutations are selected from S492P, F494N, S495P, I539T, G550E, R555K, and any combination thereof. In some embodiments, the four mutations are S495P, I539T, G550E, and R555K.

In some embodiments, the four or more mutations are selected from S492P A534P, I539T, S1255L, K1334G, S1359A, Q1411D, and any combination thereof. In some embodiments, the four mutations are S492P A534P, I539T, S1359A. In some embodiments, the four or more mutations are selected from M470V, S492P, S495P, A534P, I539T, R555K, E1371Q, H1402S, and any combination thereof. In some embodiments, the four or more mutations are selected from M470V, S492P, S495P, A534P, I539T, R555K, H1402S, and any combination thereof. In some embodiments, the four or more mutations are selected from M470V, S492P, S495P, A534P, I539T, R555K, E1371Q, and any combination thereof. In some embodiments, the four or more mutations are selected from M470V, S492P, S495P, A534P, I539T, and any combination thereof. In some embodiments, the four mutations are S492P, S495P, A534P, and I539T.

In some embodiments, the four or more mutations are selected from M470V, S492P, S495P, A534P, I539T, R555K, and any combination thereof. In some embodiments, the four mutations are M470V, S492P, I539T, and A534P.

In some embodiments, the four or more mutations are selected from S492P, S495P, A534P, I539T, R555K, R553Q and any combination thereof.

In some embodiments, the four or more mutations are selected from S492, A534P, I539T, G550E, R555K, and any combination thereof.

In some embodiments, four or more mutations are S492P, F494N, S495P, A534P, I539T, G550E, R555K, S1255L, K1334G, S1359A, and Q1411D. In some embodiments, the four or more mutations are S492P, A534P, I539T, S1255L, K1334G, S1359A, and Q1411. In some embodiments, the four or more mutations are S492P, F494N, S495P, A534P, I539T, G550E, R555K, and S1359A. In some embodiments, the four or more mutations are S492P, F494N, S495P, A534P, I539T, G550E, R555K, and S1359A. In some embodiments, the four or more mutations are S492P, F494N, S495P, A534P, I539T, G550E, and R555K. In some embodiments, the four or more mutations are S492P, F494N, S495P, A534P, I539T, G550E, and R555K. In some embodiments, four or more mutations are M470V, S492P, S495P, A534P, I539T, and R555K. In some embodiments, the four or more mutations are M470V, S492P, S495P, A534P, and I539T. In some embodiments, four or more mutations are S492P, A534P, I539T, and S1359A.

Another aspect of the invention relates to a modified human cystic fibrosis transmembrane conductance regulator (CFTR) polypeptide or functional fragment thereof, wherein the polypeptide differs from the wild-type human CFTR protein (SEQ ID NO:1) or fragment thereof by the presence of one, two, or three mutations selected from V150D, M470V, S492P, F494N, S495P, I539T, G550E, G551D, R553Q, R555K, Q637R, H1402S, E1371Q, and any combination thereof, such that the stability of the polypeptide is increased relative to that of the wild-type human CFTR polypeptide or fragment thereof.

In some embodiments, the one, two, or three mutations are selected from S495P, G550E, R555K, and any combination thereof. In some embodiments, the one or two mutations are selected from G550E, R555K, and any combination thereof. In some embodiments, the one or two mutations are selected from S492P, I539T, and any combination thereof. In some embodiments, the one or two mutations are selected from S495P, I539T, and any combination thereof. In some embodiments, the one or two mutations are selected from S495P, S492P, and any combination thereof. In some embodiments, the one or two mutations are selected from F494N, Q637R and any combination thereof.

In some embodiments, the one, two or three mutations selected from V150D, M470V, F494N, S495P, I539T, G550E, G551D, R553Q, R555K, Q637R, H1402S, E1371Q, and any combination thereof are further combined with mutation A534P. In some embodiments, the one mutation is I539T.

In some embodiments, the one, two, or three mutations selected from V150D, M470V, S492P, F494N, S495P, G550E, G551D, R553Q, R555K, Q637R, H1402S, E1371Q, and any combination thereof are further combined with mutation A534P. In some embodiments, the mutation is G550E. In some embodiments, the mutation is S495P. In some embodiments, the mutation is S492P. In some embodiments, the mutation is M470V. In some embodiments, the mutation is V150D. In some embodiments, the mutation is G551D.

In some embodiments, the polypeptide or functional fragment of the invention further comprises a deletion of amino acid residue F508 (ΔF508). In some embodiments, the polypeptide or functional fragment further comprises a deletion of amino acid residues 405-436 (ΔRI) or a deletion of amino acid residues 404-435(ΔRI'). In some embodiments, a functional fragment of the invention is the amino acid sequence of the nuclear binding domain 1 (NBD1). In some embodiments, the polypeptide has increased stability relative to a CFTR polypeptide comprising a deletion of amino acid residue F508 (ΔF508) and/or comprising a deletion of amino acid residues 405-436 (ΔRI) and/or comprising a deletion of amino acid residues 404-435 (ΔRI').

The modified CFTR polypeptide or functional fragment thereof of the invention is a modified human wild-type CFTR protein comprising the following amino acid sequence:

```
                                                                  (SEQ ID NO: 1)
MQRSPLEKAS VVSKLFFSWT RPILRKGYRQ RLELSDIYQI PSVDSADNLS EKLEREWDRE    60

LASKKNPKLI NALRRCFFWR FMFYGIFLYL GEVTKAVQPL LLGRIIASYD PDNKEERSIA   120

IYLGIGLCLL FIVRTLLLHP AIFGLHHIGM QMRIAMFSLI YKKTLKLSSR VLDKISIGQL   180

VSLLSNNLNK FDEGLALAHF VWIAPLQVAL LMGLIWELLQ ASAFCGLGFL IVLALFQAGL   240

GRMMMKYRDQ RAGKISERLV ITSEMIENIQ SVKAYCWEEA MEKMIENLRQ TELKLTRKAA   300

YVRYFNSSAF FFSGFFVVFL SVLPYALIKG IILRKIFTTI SFCIVLRMAV TRQFPWAVQT   360

WYDSLGAINK IQDFLQKQEY KTLEYNLTTT EVVMENVTAF WEEGFGELFE KAKQNNNNRK   420

TSNGDDSLFF SNFSLLGTPV LKDINFKIER GQLLAVAGST GAGKTSLLMV IMGELEPSEG   480

KIKHSGRISF CSQFSWIMPG TIKENIIFGV SYDEYRYRSV IKACQLEEDI SKFAEKDNIV   540

LGEGGITLSG GQRARISLAR AVYKDADLYL LDSPFGYLDV LTEKEIFESC VCKLMANKTR   600

ILVTSKMEHL KKADKILILH EGSSYFYGTF SELQNLQPDF SSKLMGCDSF DQFSAERRNS   660

ILTETLHRFS LEGDAPVSWT ETKKQSFKQT GEFGEKRKNS ILNPINSIRK FSIVQKTPLQ   720

MNGIEEDSDE PLERRLSLVP DSEQGEAILP RISVISTGPT LQARRRQSVL NLMTHSVNQG   780

QNIHRKTTAS TRKVSLAPQA NLTELDIYSR RLSQETGLEI SEEINEEDLK ECFFDDMESI   840

PAVTTWNTYL RYITVHKSLI FVLIWCLVIF LAEVAASLVV LWLLGNTPLQ DKGNSTHSRN   900

NSYAVIITST SSYYVFYIYV GVADTLLAMG FFRGLPLVHT LITVSKILHH KMLHSVLQAP   960

MSTLNTLKAG GILNRFSKDI AILDDLLPLT IFDFIQLLLI VIGAIAVVAV LQPYIFVATV  1020

PVIVAFIMLR AYFLQTSQQL KQLESEGRSP IFTHLVTSLK GLWTLRAFGR QPYFETLFHK  1080

ALNLHTANWF LYLSTLRWFQ MRIEMIFVIF FIAVTFISIL TTGEGEGRVG IILTLAMNIM  1140

STLQWAVNSS IDVDSLMRSV SRVFKFIDMP TEGKPTKSTK PYKNGQLSKV MIIENSHVKK  1200

DDIWPSGGQM TVKDLTAKYT EGGNAILENI SFSISPGQRV GLLGRTGSGK STLLSAFLRL  1260
```

```
                                    -continued
LNTEGEIQID  GVSWDSITLQ  QWRKAFGVIP  QKVFIFSGTF  RKNLDPYEQW  SDQEIWKVAD  1320

EVGLRSVIEQ  FPGKLDFVLV  DGGCVLSHGH  KQLMCLARSV  LSKAKILLLD  EPSAHLDPVT  1380

YQIIRRTLKQ  AFADCTVILC  EHRIEAMLEC  QQFLVIEENK  VRQYDSIQKL  LNERSLFRQA  1440

ISPSDRVKLF  PHRNSSKCKS  KPQIAALKEE  TEEEVQDTRL                          1480
```

In some embodiments, the modified polypeptide or functional fragment of a wild-type CFTR protein from which the modified CFTR polypeptide or functional fragment thereof of the invention is derived from comprises, consists essentially of, or consists of the amino acid sequence of the nuclear binding domain (NBD1) or a portion thereof. In some embodiments, the NBD1 of a human wild-type CFTR from which the modified CFTR polypeptide or functional fragment thereof is derived from comprises amino acid residues ranging from about amino acid residues 433 to about 584 of the wild-type CFTR protein. In some embodiments, the modified CFTR polypeptide or functional fragment thereof of the invention comprises the entire amino acid sequence of the nuclear binding domain (NBD1) of the wild-type CFTR protein. In some embodiments, the modified CFTR polypeptide or functional fragment thereof comprises only a portion of the amino acid sequence of the NBD1 of the wild-type CFTR protein. In some embodiments, the functional CFTR fragment of the invention comprises an amino acid sequence ranging from about amino acid residues 458 to about 557 of the wild-type CFTR protein.

In some embodiments the modified CFTR polypeptide or functional fragment thereof is modified with one or more tags and/or fusion proteins. In some, embodiments, the polypeptide or functional fragment thereof of the invention may further comprise one or more tags selected from a $His_{10}$-purification tag, FLAG epitope, a green fluorescent protein (EGFP), and a SUMO fusion protein epitope In some embodiments, wild-type CFTR protein or fragment thereof from which the modified CFTR polypeptide or functional fragment thereof is derived from comprises, consists essentially of, or consists of one or more deletion(s) of amino acid residues. In some embodiments, the wild-type CFTR protein or fragment thereof from which the modified CFTR polypeptide or functional fragment thereof is derived from comprises a deletion of amino acid residue F508 (ΔF508) and/or a deletion of amino acid residues 405-436 (ΔRI) and/or a deletion of amino acid residues 404-435 (ΔRI').

Another aspect of the inventions relates to the protein structural stability of the modified CFTR polypeptide or functional fragment thereof of the invention. Structural protein stability describes the stability of the protein's native three-dimensional structure of folded conformation relative to its denatured or unfolded state and is expressed as a function of temperature (i.e., $T_m$; unfolding temperature). In some embodiments, the protein stability of the modified. CFTR polypeptide or functional fragment thereof is higher (i.e., more stable) than the protein stability of the wild-type CFTR protein or fragment thereof. The increase may be in structural stability ($T_m$, $T_m^{cal}$) and/or thermal stability ($T_m^{trp}$) and/or functional stability ($T_m^{func}$).

In some embodiments, the structural stability of the modified CFTR polypeptide or functional fragment thereof is increased by an amount of $\Delta T_m^{cal}$ ranging from about 1% to about 40%, from about 3% to about 38%, from about 5% to about 35%, from about 10% to about 30%, from about 15% to about 25% compared to that of the wild-type CFTR protein or fragment thereof.

In some embodiments, the structural protein stability of the modified CFTR polypeptide or functional fragment thereof is increased by at least an amount of about 3%, about 4%, about 5%, about 6%, about 7%, about 8%, about 9%, about 10% about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, or at least about 39% compared to the wild-type CFTR protein or fragment thereof.

In some embodiments, the $T_m$ of the modified CFTR polypeptide or functional fragment thereof ranges from about 57° C. to about 80° C., from about 60° C. to about 75° C., from about 65° C. to about 75° C., or from about 70° C. to about 75° C. In some embodiments, the $T_m$ of the modified CFTR polypeptide or functional fragment thereof is at least about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77, about 78° C., or at least about 79° C.

Another aspect of the invention relates to the ion channel conductivity activity of the modified CFTR polypeptide or functional fragment thereof of the invention, wherein the ion channel conductivity measures the ability and/or efficiency of transporting ions across a membrane. In some embodiments, the ion channel conductivity of the modified CFTR polypeptide or functional fragment thereof is higher than the ion channel conductivity of the wild-type CFTR protein or fragment thereof. In some embodiments, the modified CFTR polypeptide or functional fragment thereof exhibits an ion channel conductivity of at least about 0.1%, about 0.2%, about 0.3%, about 0.4%, about 0.5%, about 0.6%, about 0.7%, about 0.8%, about 0.9%, about 1.0%, about 1.1%, or about 1.2% higher compared to the conductivity of the wild-type CFTR protein or fragment thereof.

In some embodiments, the modified CFTR polypeptide or functional fragment thereof exhibits an ion channel conductivity of at least about 0.1 pS, about 0.2 pS, about 0.3 pS, about 0.4 pS about 0.5 pS, about 1.0 pS, about 1.5 pS, about 2.0 pS, about 2.5 pS, about 3.0 pS, about 3.5 pS, about 4.0 pS, or at least about 4.5 pS higher compared to the ion channel conductivity of the wild-type CFTR protein or fragment thereof. In some embodiments, ion channel conductivity of the modified CFTR polypeptide or functional fragment thereof ranges from about 12 pS to about 16 pS, or from about 12.5 pS to about 14 pS. In some embodiments, the conductance is at least about 12 pS, about 12.5 pS, about 13 pS, about 13.5 pS, about 14 pS, about 14.5 pS, about 15 pS, or about 15.5 pS.

In some embodiments, the increased ion channel conductivity of the modified CFTR polypeptide or functional fragment thereof compared to the ion channel conductivity of the wild-type CFTR protein or fragment thereof is temperature dependent. In some embodiments, the modified CFTR polypeptide or functional fragment thereof exhibits a higher ion channel conductivity compared to the wild type CFTR protein or fragment therefor at temperatures ranging from 33° C. to about 60° C., from about 34° C. to about 50° C., or from about 38° C. to about 48° C. In some embodiments, the temperature is at least about 33° C., about 34° C., about 35° C., about 36° C., about 37° C., about 38° C., about 39° C., about 40° C., about 41° C., about 42° C., about 43° C., about 44° C., or at least about 45° C.

Another aspect of the invention relates of the ATPase activity of the modified CFTR polypeptide or functional fragment thereof of the invention, wherein the ATPase activity is measured as a function of ATP hydrolysis to produce energy for the cell. In some embodiments, the ATPase activity of a modified CFTR polypeptide or functional fragment thereof having no more than five mutations and comprising a deletion of amino acid residues 405-436 (ΔRI) is higher compared to the ATPase activity of the wild-type CFTR peptide or fragment thereof. In some embodiments, the ATPase activity of such modified CFTR polypeptide or functional fragment thereof is increased by and amount ranging from about 1.5-fold, about 1.8-fold, 2-fold, 2.5-fold, 3.0-fold, 3.5-fold, 4.0-fold, 4.5-fold, 5.0-fold, 5.5-fold, or about 6.0 fold compared to the ATPase activity of the wild-type CFTR protein.

In some embodiments, the ATPase activity of the modified CFTR polypeptide or functional fragment thereof ranges from about 5 nmol/h/µg to about 35 nmol/h/µg, from about 10 nmol/h/µg to about 25 nmol/h/µg, or from about 15 to about 20 nmol/h/µg. In some embodiments, the ATPase activity of the modified CFTR polypeptide or functional fragment thereof is at least about 7 nmol/h/µg, about 8 nmol/h/µg, about 9 nmol/h/µg, about 10 nmol/h/µg, about 11 nmol/h/µg, about 12 nmol/h/µg, about 13 nmol/h/µg, about 14 nmol/h/µg, about 15 nmol/h/µg, about 16 nmol/h/µg, about 17 nmol/h/µg, about 18 nmol/h/µg, about 19 nmol/h/µg, about 20 nmol/h/µg, about 21 nmol/h/µg, about 22 nmol/h/µg, about 23 nmol/h/µg, about 24 nmol/h/µg, about 25 nmol/h/µg, about 26 nmol/h/µg, about 27 nmol/h/µg, about 28 nmol/h/µg, about 29 nmol/h/µg, about 30 nmol/h/µg, about 31 nmol/h/µg, about 32 nmol/h/µg, about 33 nmol/h/µg, about 34 nmol/h/µg, or at least about 35 nmol/h/µg.

Another aspect of the invention relates to a composition comprising the modified CFTR polypeptide of functional fragment thereof of the invention. In some embodiments, the composition may comprise one or more suitable carriers for the polypeptide. In some embodiments, the composition comprising the modified CFTR polypeptide of functional fragment thereof of the invention is a liquid.

The present invention additionally provides a nucleic acid molecule encoding the modified CFTR polypeptide or functional fragment thereof of the invention. In some embodiments, the nucleic acid molecule of the invention is a modified from the human wild-type CFTR nucleotide sequence (SEQ ID NO:2):

```
   1    aattggaagc aaatgacatc acagcaggtc agagaaaaag ggttgagcgg caggcaccca
  61    gagtagtagg tctttggcat taggagcttg agcccagacg gccctagcag ggaccccagc
 121    gcccgagaga ccatgcagag gtcgcctctg gaaaaggcca gcgttgtctc caaacttttt
 181    ttcagctgga ccagaccaat tttgaggaaa ggatacagac agcgcctgga attgtcagac
 241    atataccaaa tccccttctgt tgattctgct gacaatctat ctgaaaaatt ggaaagagaa
 301    tgggatagag agctggcttc aaagaaaaat cctaaactca ttaatgccct tcggcgatgt
 361    tttttctgga gatttatgtt ctatggaatc ttttttatatt taggggaagt caccaaagca
 421    gtacagcctc tcttactggg aagaatcata gcttcctatg acccggataa caaggaggaa
 481    cgctctatcg cgatttatct aggcataggc ttatgccttc tctttattgt gaggacactg
 541    ctcctacacc cagccatttt tggccttcat cacattggaa tgcagatgag aatagctatg
 601    tttagtttga tttataagaa gactttaaag ctgtcaagcc gtgttctaga taaaataagt
 661    attggacaac ttgttagtct cctttccaac aacctgaaca aatttgatga aggacttgca
 721    ttggcacatt tcgtgtggat cgctcctttg caagtggcac tcctcatggg gctaatctgg
 781    gagttgttac aggcgtctgc cttctgtgga cttggtttcc tgatagtcct tgccctttt
 841    caggctgggc tagggagaat gatgatgaag tacagagatc agagagctgg gaagatcagt
 901    gaaagacttg tgattacctc agaaatgatt gaaaatatcc aatctgttaa ggcatactgc
 961    tgggaagaag caatggaaaa aatgattgaa aacttaagac aaacagaact gaaactgact
1021    cggaaggcag cctatgtgag atacttcaat agctcagcct tcttcttctc agggttcttt
1081    gtggtgtttt tatctgtgct tcccctatgca ctaatcaaag gaatcatcct ccggaaaata
1141    ttcaccacca tctcattctg cattgttctg cgcatggcgg tcactcggca atttcctgg
1201    gctgtacaaa catggtatga ctctcttgga gcaataaaca aaatacagga tttcttacaa
1261    aagcaagaat ataagacatt ggaatataac ttaacgacta cagaagtagt gatggagaat
```

```
1321  gtaacagcct tctgggagga gggatttggg gaattatttg agaaagcaaa acaaaacaat
1381  aacaatagaa aaacttctaa tggtgatgac agcctcttct tcagtaattt ctcacttctt
1441  ggtactcctg tcctgaaaga tattaatttc aagatagaaa gaggacagtg gttggcggtt
1501  gctggatcca ctggagcagg caagacttca cttctaatgg tgattatggg agaactggag
1561  ccttcagagg gtaaaattaa gcacagtgga agaatttcat tctgttctca gttttcctgg
1621  attatgcctg gcaccattaa agaaaatatc atctttggtg tttcctatga tgaatataga
1681  tacagaagcg tcatcaaagc atgccaacta gaagaggaca ctccaagtt tgcagagaaa
1741  gacaatatag ttcttggaga aggtggaatc acactgagtg gaggtcaacg agcaagaatt
1801  tctttagcaa gagcagtata caaagatgct gatttgtatt tattagactc tccttttgga
1861  tacctagatg ttttaacaga aaagaaaata tttgaaagct gtgtctgtaa actgatggct
1921  aacaaaacta ggattttggt cacttctaaa atggaacatt taaagaaagc tgacaaaata
1981  ttaattttgc atgaaggtag cagctatttt tatgggacat ttcagaact ccaaaatcta
2041  cagccagact ttagctcaaa actcatggga tgtgattctt tcgaccaatt tagtgcagaa
2101  agaagaaatt caatcctaac tgagaccta caccgtttct cattagaagg agatgctcct
2161  gtctcctgga cagaaacaaa aaacaatct tttaaacaga ctggagagtt tggggaaaaa
2221  aggaagaatt ctattctcaa tccaatcaac tctatacgaa aattttccat tgtgcaaaag
2281  actcccttac aaatgaatgg catcgaagag gattctgatg agcctttaga gagaaggctg
2341  tccttagtac cagattctga gcagggagag gcgatactgc ctcgcatcag cgtgatcagc
2401  actggcccca cgcttcaggc acgaaggagg cagtctgtcc tgaacctgat gacacactca
2461  gttaaccaag gtcagaacat tcaccgaaag acaacagcat ccacacgaaa agtgtcactg
2521  gcccctcagg caaacttgac tgaactggat atatattcaa gaaggttatc tcaagaaact
2581  ggcttggaaa taagtgaaga aattaacgaa gaagacttaa aggagtgctt ttttgatgat
2641  atggagagca taccagcagt gactacatgg aacacatacc ttcgatatat tactgtccac
2701  aagagcttaa ttttttgtgct aatttggtgc ttagtaattt ttctggcaga ggtggctgct
2761  tcttttggttg tgctgtggct ccttggaaac actcctcttc aagacaaagg gaatagtact
2821  catagtagaa ataacagcta tgcagtgatt atcaccagca ccagttcgta ttatgtgttt
2881  tacatttacg tgggagtagc cgacactttg cttgctatgg gattcttcag aggtctacca
2941  ctggtgcata ctctaatcac agtgtcgaaa atttacacc acaaaatgtt acattctgtt
3001  cttcaagcac ctatgtcaac cctcaacacg ttgaaagcag gtgggattct taatagattc
3061  tccaaagata tagcaatttt ggatgacctt ctgcctctta ccatatttga cttcatccag
3121  ttgttattaa ttgtgattgg agctatagca gttgtcgcag ttttacaacc tacatctttt
3181  gttgcaacag tgccagtgat agtggctttt attatgttga gagcatattt cctccaaacc
3241  tcacagcaac tcaaacaact ggaatctgaa ggcaggagtc aattttcac tcatcttgtt
3301  acaagcttaa aaggactatg gacacttcgt gccttcggac ggcagcctta ctttgaaact
3361  ctgttccaca agctctgaa tttacatact gccaactggt tcttgtacct gtcaacactg
3421  cgctggttcc aaatgagaat agaaatgatt tttgtcatct tcttcattgc tgttaccttc
3481  atttccatt taacaacagg agaaggagaa ggaagagttg gtattatcct gactttagcc
3541  atgaatatca tgagtacatt gcagtgggct gtaaactcca gcatagatgt ggatagcttg
3601  atgcgatctg tgagccgagt ctttaagttc attgacatgc caacagaagg taaacctacc
3661  aagtcaacca aaccatacaa gaatggccaa ctctcgaaag ttatgattat tgagaattca
```

-continued

```
3721  cacgtgaaga aagatgacat ctggccctca gggggccaaa tgactgtcaa agatctcaca
3781  gcaaaataca cagaaggtgg aaatgccata ttagagaaca tttccttctc aataagtcct
3841  ggccagaggg tgggcctctt gggaagaact ggatcaggga agagtacttt gttatcagct
3901  tttttgagac tactgaacac tgaaggagaa atccagatcg atggtgtgtc ttgggattca
3961  ataactttgc aacagtggag gaaagccttt ggagtgatac cacagaaagt atttattttt
4021  tctggaacat ttagaaaaaa cttggatccc tatgaacagt ggagtgatca agaaatatgg
4081  aaagttgcag atgaggttgg gctcagatct gtgatagaac agtttcctgg gaagcttgac
4141  tttgtccttg tggatggggg ctgtgtccta agccatggcc acaagcagtt gatgtgcttg
4201  gctagatctg ttctcagtaa ggcgaagatc ttgctgcttg atgaacccag tgctcatttg
4261  gatccagtaa cataccaaat aattagaaga actctaaaac aagcatttgc tgattgcaca
4321  gtaattctct gtgaacacag gatagaagca atgctggaat gccaacaatt tttggtcata
4381  gaagagaaca aagtgcggca gtacgattcc atccagaaac tgctgaacga gaggagcctc
4441  ttccggcaag ccatcagccc ctccgacagg gtgaagctct tccccaccg gaactcaagc
4501  aagtgcaagt ctaagcccca gattgctgct ctgaaagagg agacagaaga agaggtgcaa
4561  gatacaaggc tttagagagc agcataaatg ttgacatggg acatttgctc atggaattgg
4621  agctcgtggg acagtcacct catggaattg gagctcgtgg aacagttacc tctgcctcag
4681  aaaacaagga tgaattaagt ttttttttaa aaaagaaaca tttggtaagg gaattgagg
4741  acactgatat gggtcttgat aaatggcttc ctggcaatag tcaaattgtg tgaaaggtac
4801  ttcaaatcct tgaagattta ccacttgtgt tttgcaagcc agattttcct gaaaaccctt
4861  gccatgtgct agtaattgga aaggcagctc taaatgtcaa tcagcctagt tgatcagctt
4921  attgtctagt gaaactcgtt aatttgtagt gttggagaag aactgaaatc atacttctta
4981  gggttatgat taagtaatga taactggaaa cttcagcggt ttatataagc ttgtattcct
5041  ttttctctcc tctccccatg atgtttagaa acacaactat attgtttgct aagcattcca
5101  actatctcat ttccaagcaa gtattagaat accacaggaa ccacaagact gcacatcaaa
5161  atatgcccca ttcaacatct agtgagcagt caggaaagag aacttccaga tcctggaaat
5221  cagggttagt attgtccagg tctaccaaaa atctcaatat ttcagataat cacaatacat
5281  cccttacctg ggaaagggct gttataatct ttcacagggg acaggatggt tcccttgatg
5341  aagaagttga tatgcctttt cccaactcca gaaagtgaca agctcacaga cctttgaact
5401  agagtttagc tggaaaagta tgttagtgca aattgtcaca ggacagcccc tcttccaca
5461  gaagctccag gtagagggtg tgtaagtaga taggccatgg gcactgtggg tagacacaca
5521  tgaagtccaa gcatttagat gtataggttg atggtggtat gttttcaggc tagatgtatg
5581  tacttcatgc tgtctacact aagagagaat gagagacaca ctgaagaagc accaatcatg
5641  aattagtttt atatgcttct gttttataat tttgtgaagc aaaattttt ctctaggaaa
5701  tatttatttt aataatgttt caaacatata taacaatgct gtattttaaa agaatgatta
5761  tgaattacat ttgtataaaa taatttttat atttgaaata ttgacttttt atggcactag
5821  tatttctatg aaatattatg ttaaaactgg gacaggggag aacctagggt gatattaacc
5881  aggggccatg aatcaccttt tggtctggag ggaagccttg gggctgatgc agttgttgcc
5941  cacagctgta tgattcccag ccagcacagc ctcttagatg cagttctgaa gaagatggta
6001  ccaccagtct gactgtttcc atcaagggta cactgccttc tcaactccaa actgactctt
6061  aagaagactg cattatattt attactgtaa gaaaatatca cttgtcaata aaatccatac
6121  atttgtgtga aa
``` or a sequence having at least 90%, 91%, 92%, 93%, 94%, 95%, 96%, 97%, 98%, or 99% identify thereto.

Another aspect of the invention relates to an expression vector comprising the nucleic acid molecule (i.e., polynucleotide) of the invention. Suitable expression vectors include, without limitation, plasmids and viral vectors. For purposes of the invention, the regulatory regions (i.e., promoters, transcriptional regulatory regions, and translational termination regions) in the expression vector can be native/analogous to the organism or cell and/or the regulatory regions can be native/analogous to the other regulatory regions. Alternatively, the regulatory regions may be heterologous to the organism or cell and/or to each other (i.e., the regulatory regions). Thus, for example, a promoter can be heterologous when it is operably linked to a polynucleotide from a species different from the species from which the polynucleotide was derived. Alternatively, a promoter can also be heterologous to a selected nucleotide sequence if the promoter is from the same/analogous species from which the polynucleotide is derived, but one or both (i.e., promoter and polynucleotide) are substantially modified from their original form and/or genomic locus, or the promoter is not the native promoter for the operably linked polynucleotide.

In addition to the promoters described above, the expression vector also can include other regulatory sequences. As used herein, "regulatory sequences" means nucleotide sequences located upstream (5' non-coding sequences), within or downstream (3' non-coding sequences) of a coding sequence, and which influence the transcription, RNA processing or stability, or translation of the associated coding sequence. Regulatory sequences include, but are not limited to, enhancers, introns, translation leader sequences and polyadenylation signal sequences.

The expression vector also can optionally include a transcriptional and/or translational termination region (i.e., termination region) that is functional in the organism. A variety of transcriptional terminators is available for use in expression vectors and is responsible for the termination of transcription beyond the transgene and correct mRNA polyadenylation. The termination region may be native to the transcriptional initiation region, may be native to the operably linked nucleotide sequence of interest, may be native to the host, or may be derived from another source (i.e., foreign or heterologous to the promoter, the nucleotide sequence of interest, the host, or any combination thereof).

Regardless of the type of regulatory sequence(s) used, they can be operably linked to the nucleotide sequence of the polynucleotide of the invention. As used herein, "operably linked" means that elements of a nucleic acid construct such as an expression cassette are configured so as to perform their usual function. Thus, regulatory or control sequences (e.g., promoters) operably linked to a nucleotide sequence of interest are capable of effecting expression of the nucleotide sequence of interest. The control sequences need not be contiguous with the nucleotide sequence of interest, so long as they function to direct the expression thereof. Thus, for example, intervening untranslated, yet transcribed, sequences can be present between a promoter and a coding sequence, and the promoter sequence can still be considered "operably linked" to the coding sequence. A nucleotide sequence of the present invention can be operably linked to a regulatory sequence, thereby allowing its expression in a cell and/or subject.

The expression vector also can include a nucleotide sequence for a selectable marker, which can be used to select a transformed organism or cell. As used herein, "selectable marker" means a nucleic acid that when expressed imparts a distinct phenotype to the organism or cell expressing the marker and thus allows such transformed organisms or cells to be distinguished from those that do not have the marker. Such a nucleic acid may encode either a selectable or screenable marker, depending on whether the marker confers a trait that can be selected for by chemical means, such as by using a selective agent (e.g., an antibiotic or the like), or on whether the marker is simply a trait that one can identify through observation or testing, such as by screening. Of course, many examples of suitable selectable markers are known in the art and can be used in the expression vectors described herein.

In some embodiments, the expression vector of the invention includes, but is not limited to, a lentiviral vector, e.g., a lentiviral vector comprising, consisting essentially of, or consisting of a promoter (e.g., TRE promoter), a modified wild-type CFTR sequence optionally tagged (e.g., a FLAG epitope, a $His_{10}$-tag) attached to the modified CFTR sequence (e.g., in the fourth intracellular loop), and a SUMO region and/or an enhanced green fluorescent protein region (EGFP) (Hildebrandt E. et al., Mol Biotechnol (2015), 57(5), 391-405; FIG. 10, Panel A).

Another aspect of the invention relates to a host cell comprising the nucleic acid molecule (i.e., polynucleotide) or the expression vector of the invention. When a nucleic acid is inserted into a suitable host cell, e.g., a prokaryotic or a eukaryotic cell and the host cell replicates, the protein can be recombinantly produced. Suitable host cells will depend on the vector and can include mammalian cells, animal cells, human cells, simian cells, insect cells, yeast cells, plant cells, and bacterial cells as described above and constructed using well known methods. Examples of eukaryotic host cells for replication and/or expression of a vector include, but should not be limited to, *C. elegans*, HeLa, NIH3T3, Jurkat, 293, Cos, CHO, Saos, yeast, nematodes, insect cells, and PC12. Many host cells from various cell types and organisms are available and would be known to one of skill in the art. Examples of useful mammalian host cell lines include, but should not be limited to, VERO and HeLa cells, Chinese hamster ovary (CHO) cell lines, W138, BHK, COS-7, 293, HepG2, 3T3, RIN, Human embryonic kidney cell lines (HEK), and MDCK cell lines. Other Examples include cell lines such as D165, D421, D359, D727, D851, D1012, D1013, D744, D869, D872, D1028, D805, D804, D742, D743, D507 D1044, D992, D727, D994, D851, and/or D1022. In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Examples of prokaryotic hosts include, but should not be limited to *E. coli* strains; bacilli such as *Bacillus subtilis*; and other enterobacteriaceae such as *Salmonella typhimurium, Serratia marcescens*, and various *Pseudomonas* species. In addition to the use of viral vector for insertion of exogenous nucleic acid into cells, the nucleic acid can be inserted into the host cell by methods well known in the art such as transformation for bacterial cells; transfection using calcium phosphate precipitation for mammalian cells; DEAE-dextran; electroporation; or microinjection.

In one aspect, this invention is directed to a method for producing the recombinant modified CFTR polypeptide or functional fragment thereof as described herein, the method comprising: introducing an expression vector comprising a nucleotide sequence coding for the recombinant modified CFTR polypeptide or functional fragment thereof into a host cell to provide a recombinant cell; and culturing the cell in cell culture medium under conditions such that the recombinant modified CFTR polypeptide or functional fragment thereof is expressed by the recombinant cell. In some embodiments, the method further comprises collecting the cells, lysing the cells, centrifugation of the lysed cells to collect/isolate the membranes containing the recombinant modified CFTR polypeptide or functional fragment thereof. In some embodiments, the method further comprises isolating or purifying the recombinant modified CFTR polypeptide or functional fragment thereof from the collected/isolated membranes (e.g., by solubilizing the membranes and/or chromatography (e.g., affinity and/or size exclusion)).

The recombinant nucleic acid molecule (i.e., polypeptides) of the invention are expected to have some or all of the biological activities of wild-type modified CFTR polypeptide or functional fragment thereof (i.e., CFTR protein or fragment thereof) and may have one or more enhanced biological activities relative to wild-type modified CFTR polypeptide or functional fragment thereof. Thus, the modified CFTR polypeptide or functional fragment thereof of the invention may be used in the same manner as the wild-type CFTR protein as is known in the art.

Another aspect of this invention relates to the use of modified CFTR polypeptide or functional fragment thereof of the invention as a research tool to investigate the factors that modulate structural stability and/or folding properties of the wild-type CFTR protein and fragments thereof. Employing modified polypeptides of the invention in methods directed to studying CFTR structure and/or function and/or optimizing the same, e.g., protein stability and folding properties, allows for the identification of important amino acid residues and regions within the CFTR protein and fragments thereof that govern such structure and/or function. Employing modified polypeptides of the invention also allows for studying their effects on biological activities such as ion channel conductivity and/or ATPase activity. Stabilized wild-type CFTR proteins and fragments thereof may be a valuable tool for biophysical and structural studies that advance CF drug development and allows for the mechanistic and structural studies of CF-causing mutations. All this information can then be used in the development of therapies involving the CFTR protein to treat CF and related diseases.

For instance, stabilizing mutations (such as mutations in this invention) of the CFTR polypeptide provides the ability to obtain an atomic resolution structure of the CFTR polypeptide. This structural information provides the basis for designing drugs, e.g., using rational structure-based drug design. These drugs are designed, for example, to target specific regions in the CFTR polypeptide to correct functional defects that cause the disease. Current drugs modulating CFTR polypeptides can be effective for treating some mutant/variant forms of functionally defective CFTR but not all mutant/variant forms. Thus, information obtained from studies using the CFTR polypeptides of the present invention can be used in the discovery of new and effective treatments that currently have no treatment options.

For example, in some embodiments, these disease variants are due to a premature translational stop codon (PTC) that in certain individuals exist within the CFTR nucleotide sequence. For example, some of the PTC mutations are near the end of the CFTR sequence (i.e., W1282X) and while these mutant forms of the CFTR polypeptide are partially defective, they are expressed and do function, albeit not normally. Therefore, any results of studies obtained using the modified CFTR polypeptides of the invention, in particular structural/folding protein studies, will allow for the determination and/or identification of important structural features in the W1282X mutant (and other PTC mutants) that can be used in designing drugs to correct the defect. In addition, there are also currently drugs in development that can suppress the PTC, but this type of treatment is only partially effective because the wild-type amino acid is not inserted in place of the PTC, and consequently the aberrant amino acid is itself a mutation (called a missense mutation) that can cause CFTR dysfunction and disease. Here too, information obtained from studies using the modified CFTR polypeptide of the invention has utility since one can determine the defect in the structure of the missense CFTR and then design drugs to correct the defect.

Thus, one aspect of the invention relates to a method of screening a compound using a modified CFTR polypeptide of the invention to identify a compound that modulates one or more biological and/or physical properties (e.g., ATPase activity, ion channel conductivity properties, structural stability and/or folding properties) of the modified CFTR polypeptide, wherein the modified CFTR polypeptide further comprises one or more destabilizing mutations relative to the wild-type human CFTR protein (SEQ ID NO:1) or fragment thereof. In some embodiments, the modified CFTR polypeptide comprises 1, 2, 3, 4, 5, 6, 7, 8, 9, or 10 destabilizing mutations. The term "destabilizing" is intended to refer to amino acid mutations of the wild-type human CFTR polypeptide that decrease and/or diminish any biological and/or physical property of the wild-type human CFTR polypeptide. In some embodiments, the modified CFTR polypeptide comprises more than 10 destabilizing mutations. In some embodiments, the destabilizing mutations are related to a disease state. The term "modulate" is intended to refer to compounds that enhance (e.g., increase, restore, improve) or inhibit (e.g., reduce) the biological and/or physical activities of the modified CFTR polypeptide (or functional fragment). For example, the interaction of the modified CFTR polypeptide or functional fragment with a binding partner can be evaluated. As another alternative, physical methods, such as NMR, can be used to assess biological function. Activity of the modified CFTR polypeptides or functional fragment can be evaluated by any method known in the art, including the methods disclosed herein. In some embodiments, the structural stability and/or biological activity of the modified CFTR polypeptide is restored and/or improved in the presence of the compound. In some embodiments, the ATPase activity of the modified CFTR polypeptide is restored and/or improved in the presence of the compound. In some embodiments, the ion channel conductivity of the modified CFTR polypeptide is restored and/or improved in the presence of the compound. In some embodiments, one or more of each of these biological and/or physical properties of the modified CFTR polypeptide is restored individually by at least about 1%, 2%, 3%, 4%, 5%, 6%, 7%, 8%, 9%, 10%, 15%, 20%, 25%, 30%, 35%, 40%, 45%, or 50%.

Any compound of interest can be screened according to the present invention. Suitable test compounds include organic and inorganic molecules. Suitable organic molecules can include but are not limited to small molecules (compounds less than about 1000 Daltons), polypeptides (including enzymes, antibodies, and Fab' fragments), carbohydrates, and/or lipids. In some embodiments, each test compound is screened in the method of the invention individually. In some embodiments, the methods of the invention can be practiced to screen a compound library, e.g., a small molecule library, a combinatorial chemical compound library, a polypeptide library, a cDNA library, a library of antisense nucleic acids, and the like, or an arrayed collection of compounds such as polypeptide and nucleic acid arrays.

In some embodiment, the invention provides methods of screening test compounds to identify a test compound that binds to specific target region of the modified CFTR polypeptide or functional fragment. Compounds that are identified as binding to the modified CFTR polypeptide or functional fragment can be subject to further screening using methods and/or other suitable techniques known in the art.

In some embodiments, the method of the invention comprises contacting a the modified CFTR polypeptide or functional fragment thereof with a test compound; and detecting whether the test compound binds to the modified CFTR polypeptide or functional fragment and/or modulates the activity of the modified CFTR polypeptide (or fragment). In another exemplary embodiment, the method comprises introducing a test compound into a cell that comprises the modified CFTR polypeptide or functional fragment; and detecting whether the compound binds to the modified CFTR polypeptide or functional fragment and/or modulates the activity of the modified CFTR polypeptide or functional fragment in the cell. The modified CFTR polypeptide can be endogenously produced in the cell. Alternatively or additionally, the cell can be modified to comprise an isolated modified CFTR polynucleotide encoding, and optionally overexpressing, the modified CFTR polypeptide or functional fragment thereof. Compounds that are identified as modulators of activity can optionally be further screened using the methods described herein (e.g., structural stability, ATPase activity, ion channel conductivity, and the like).

In some embodiments, the screening assay can be a cell-based or cell-free assay. In some embodiments, the modified CFTR polypeptide (or functional fragment thereof) or modified CFTR polynucleotide can be free in solution, affixed to a solid support, expressed on a cell surface, or located within a cell. With respect to cell-based assays, any suitable cell can be used, including bacteria, yeast, insect cells (e.g., with a baculovirus expression system), avian cells, or mammalian cells.

In some embodiments, the screening assays can also be carried out in vivo in animals. Thus, as still a further aspect, the invention provides a transgenic non-human animal comprising an isolated modified CFTR polynucleotide encoding a modified CFTR polypeptide or functional fragment thereof, which can be produced according to methods well-known in the art. The transgenic non-human animal can be from any species, including avians and non-human mammals. According to this aspect of the invention, suitable non-human mammals include mice, rats, rabbits, guinea pigs, goats, sheep, pigs, and cattle. Suitable avians include chickens, ducks, geese, quail, turkeys, and pheasants.

The modified CFTR polynucleotide encoding the modified CFTR polypeptide or functional fragment can be stably incorporated into cells within the transgenic animal (typically, by stable integration into the genome or by stably maintained episomal constructs). It is not necessary that every cell contain the transgene, and the animal can be a chimera of modified and unmodified cells, as long as a sufficient number of cells comprise and express the polynucleotide encoding the polypeptide or functional fragment so that the animal is a useful screening tool. Exemplary methods of using the transgenic non-human animals of the invention for in vivo screening of compounds comprise administering a test compound to a transgenic non-human animal (e.g., a mammal such as a mouse) comprising an isolated modified CFTR polynucleotide encoding a modified CFTR polypeptide or functional fragment thereof stably incorporated into the genome and detecting whether the test compound modulates the modified CFTR polypeptide biological activity and/or physical properties. It is known in the art how to measure these responses in vivo.

Having described the present invention, the same will be explained in greater detail in the following examples, which are included herein for illustration purposes only, and which are not intended to be limiting to the invention.

Example 1: Various Studies of NBD1 and Full Length CFTR

NBD1 purification. CFTR NBD1 (residues 387-646, Δ1405-436D containing the wild type sequence with the M470 polymorphism, referred herein as ΔRI-NBD1, was expressed in E. coli, and the protein purified in 150 mM NaCl, 20 mM HEPES pH 7.5, 10% glycerol, 10% ethylene glycol, 1 mM tris-(2-carboxymethyl) phosphine, 2 mM ATP, 3 mM $MgCl_2$ as previously described (S. Atwell, et al., Protein Eng. Des Sel, 23 (2010) 375-384; C. Wang, et al., Protein Sci, 19 (2010) 1932-1947; I. Protasevich, et al., Protein Sci, 19 (2010) 1917-1931; Z. Yang, et al., Protein Sci, 23 (2014) 769-789). Proteins were >98% pure as judged by Coomassie Blue staining of SDS-PAGE gels (FIG. 9), showed no evidence of aggregation and ran as monomers during gel filtration. Protein concentration was determined with the Pierce BCA 660 nm assay in microtiter plate format, using Bacillus subtilis NAD synthetase as a standard. Proteins were stored at −80° C.

Differential scanning calorimetry (DSC) was carried out on the VP-Capillary DSC System (MicroCal, Malvern Instruments), in 0.13 mL cells with 0.5 mg/ml proteins, at a heating rate of 2° C./min, and an external pressure of 2.0 atm to prevent possible solution degassing upon heating. DSC data were analyzed with the MicroCal Origin 7.0 software (Originlab Corp.), from which the unfolding temperature ($T_m^{cal}$) was obtained. The average $T_m^{cal}$ of ΔRI-NBD1 was 56.7±0.3° C. from 22 DSC runs, a stabilized $T_m$ approximately 14 degrees higher than that of native NBD1 containing the RI sequence. We previously showed that introducing stabilizing mutations (or the destabilizing ΔF508) into different isolated NBD1 backgrounds (ΔRI, or with RI) affected the $T_m^{cal}$ to a similar degree (C. Wang, et al., Protein Sci, 19 (2010) 1932-1947; I. Protasevich, et al., Protein Sci, 19 (2010) 1917-1931). DSC for each mutant was repeated 2-3 times, with $T_m^{cal}$ ranges among replicates ≤0.6° C. A heating rate of 1° C./min gave slightly lower $T_m$ values by about 2° C., i.e. the ΔRI-NBD1 unfolded at 54.4±0.1° C., while the 6SS-NBD1 unfolded at 71.9±0.1° C.; nevertheless the nominal difference "ΔTm" was the same.

Expression of full-length CFTR. We previously described the D165 HEK293 cell line for protein expression, wherein human CFTR was modified with $His_{10}$-SUMOstar and $^{901}$Flag affinity purification tags and C-terminally fused with the enhanced green fluorescent protein (EGFP) in a lentiviral vector (E. Hildebrandt, et al., Mol Biotechnol, 57 (2015) 391-405). The recombinant CFTR protein with a molecular mass of 212 kDa is referred to herein as WT. We had also generated a similar CFTR construct with the stabilizing mutations ΔRI'/2PT (L. A. Aleksandrov, et al., Protein expression and purification, 116 (2015) 159-166; A. A. Aleksandrov, et al., J Mol. Biol, 401 (2010) 194-210) containing a deletion in RI' encoding residues 404-435, and the NBD1 mutations S492P, A534P, and I539T (2PT) (E.

Hildebrandt, et al., Biochimica Et Biophysica Acta-Biomembranes, 1859 (2017) 289-293). Building on this ΔRI'/2PT construct, single substitutions M470V, S495P, or combinations such as the 7SS variant (ΔRI'/2PT/F494N/S495P/G550E/R555K) were added by PCR mutagenesis using 05 polymerase (New England Biolabs). We also generated ΔRI-CFTR matching the ΔRI-NBD1 deletion Δ405-436 (one amino acid difference), and added the 2PT mutations to build ΔRI/2PT. The latter served to build the 5SS (ΔRI/2PT/S495P/M470V) and 6SS (ΔRI/2PT/S495P/M470V/R555K) constructs. The open reading frames were placed under transcriptional control of either the tetracycline response element TRE-tight (TRE.t) or TRE second generation (TRE.2), as specified in Table 3. As previously described (E. P. Go, et al., J Virol, 89 (2015) 8245-8257) the vectors were packaged, pseudo typed with vesicular stomatitis virus G protein, and used to transduce CHO-S cells (Invitrogen) that had been modified to constitutively express the conventional reverse tet transactivator (rtTA) or 3G-matched rtTA, as specified in Table 3 (S. Urlinger, et al., Proc Natl Acad Sci USA, 97 (2000) 7963-7968). Transduced cells were adapted to suspension culture, and CFTR expression was induced with 1 μg/ml doxycycline at 37° C.

To assess CFTR expression at the cell surface, the cells were live-stained 24 h after induction using mouse anti Flag monoclonal antibody (Sigma F3165). Surface CFTR staining was quantified by flow cytometric analysis of at least 5,000 cells. All CFTR-expressing cell lines were analyzed in parallel, and the experiment was repeated at least four times. LinearFiow® fluorescently labeled polystyrene beads (Molecular Probes) was included in each experiment to ensure identical conditions for flow cytometry data collection. For each experiment, median fluorescent intensity (MFI) of the anti-Flag-stained cell population was determined using FlowJo software (FlowJo, LLC).

Purification of CFTR. Microsomal membrane fractions were prepared from doxycyclin-induced cells expressing recombinant CFTR constructs described above. For ATPase assays, proteins were PKA-phosphorylated and purified to homogeneity using affinity chromatography on Ni-NTA and anti-Flag resins in the presence of 0.05% decyl maltose neopentyl glycol (MNG10) as described (E. Hildebrandt, et al., Biochim Biophys Acta, 1838 (2014) 2825-2837). Purified mutant proteins were resolved on 8% polyacrylamide SDS-gels and quantitated by densitometry of in-gel EGFP fluorescence with bracketing amounts of P-glycoprotein-EGFP as external standard (D. Drew, et al., Nat Methods, 3 (2006) 303-313). Examples of human WT CFTR purified from HEK or CHO are shown in FIG. 12, Panel (A). For tryptophan-unfolding experiments, purified proteins of similar quality were obtained in a one-step purification using anti-Flag resin in the presence of 0.05% 3α,7α,12α-tri-((O-β-D-maltopyranosyl)-ethyloxy)-cholane (FA-4, Avanti Polar Lipids). The progress of the purification is shown in FIG. 12, Panel (B).

ATPase activity. Purified CFTR was supplemented with 0.4 mg/ml phospholipid (POPE/brain S/egg PC/cholesterol 5:3:1:1 w/w, and destabilized with $\frac{1}{4}^{th}$ wt. $C_{12}E_8$), and ATP hydrolysis was measured with 0.3 mM α-[$^{32}$P]-ATP, 1.5 mM $MgCl_2$, pH 7.5, at 33° C. for 2 h using thin-layer chromatography for detection of hydrolyzed ADP as described (E. Hildebrandt, Q. et al., Biochim Biophys Acta, 1838 (2014) 2825-2837). Background measured with reagent blanks containing all components except CFTR was subtracted. Mutant combinations with H1402S lacked detectable ATPase activity and served as negative controls, confirming that the assay detects CFTR-dependent ATP hydrolysis activity.

Functional Tm, the threshold temperature for inactivation of ATP hydrolysis
The approach has been previously described (E. Hildebrandt, et al., Biochimica Et Biophysica Acta-Biomembranes, 1859 (2017) 289-293). Briefly, aliquots of CFTR (about 0.1 μg in 20 μL) were pretreated 30 min at varying temperatures, then supplemented with phospholipid and assayed for ATPase activity remaining at 33° C. under the conditions stated above. Results for enzymatic activity remaining vs. pretreatment temperature were fit to a three-parameter sigmoidal equation in Sigma Plot. The derived inflection point gives $T_m^{func}$. Values were compared using Student's two-tailed t-test.

Protein unfolding monitored by intrinsic fluorescence. Effects of mutations on thermal stability of full-length CFTR were compared using Trp fluorescence, which required much less protein than DSC. $T_m^{Trp}$ was determined with 30 μl of 1-2 mg/ml protein in 50 mM Tris HCl pH 7.5, 150 mM NaCl, 1 mM dithiothreitol, 10% glycerol, 3 mM $MgCl_2$, 2 mM ATP, and 0.05% w/v FA-4, in a PolarStar Optima fluorescence plate reader (BMG Labtech, USA), in 30 μl volumes overlaid with pure mineral oil (Fisher Scientific) in a 384 well plate. Samples were heated at 1° C./min using an in-house fabricated heating block while monitoring fluorescence at λex=290±5 nm, λem=330±5 nm. CFTR unfolding was irreversible as indicated by the lack of an unfolding transition in rescans of the samples. $T_m^{Trp}$ is defined as the temperature corresponding to 50% maximal change in fluorescence. Each mutant was determined 2-3 times, and replicates varied within ≤1° C. The minimum protein concentration required to detect the transition was 1 mg/ml. The purification tags, SUMO* and GFP, by themselves did not exhibited an unfolding transition when heated in the same temperature range. Therefore, the observed changes in fluorescence were attributed to CFTR Trps.

Single-Channel analysis. Microsomal membrane fraction, prepared from CHO cells expressing the stabilized CFTR variants, were fused to planar lipid bilayers, and single-channel currents were recorded following published procedures (L. A. Aleksandrov, et al., Protein expression and purification, 116 (2015) 159-166; E. Hildebrandt, et al., Mol Biotechnol, 57 (2015) 391-405; A. A. Aleksandrov, et al., J Physiol, 587 (2009) 2875-2886; A. A. Aleksandrov, et al., FEBS Lett, 431 (1998) 97-101). Briefly, planar lipid bilayers were formed with a 3:1 mixture of 1-palmitoyl-2-oleoyl-sn-glycero-3-phosphoethanolamine and 1-palmitoyl-2-oleoyl-sn-glycero-3-phosphoserine (Avanti Polar Lipids). The lipid bilayer separated 1.0 ml of solution (cis side) from 5 ml solution (trans side). Both chambers were magnetically stirred and thermally insulated. CFTR ion channels were transferred into the preformed lipid bilayer by spontaneous fusion of membrane vesicles containing naturally folded CFTR constructs. To maintain uniform orientation and functional activity of CFTR channels transferred into the bilayer, MgATP and Protein Kinase A were added in the cis compartment only. Single channel currents were measured at −75 mV in symmetrical salt solution (300 mM Tris-HCl, pH 7.2, 3 mM $MgCl_2$ and 1 mM EGTA) under voltage-clamp conditions using an Axopatch 200B amplifier (Molecular Devices). The membrane voltage potential of −75 mV is the difference between cis and trans (ground) compartments. The output signal was filtered with an 8-pole Bessel low-pass filter LPBF-48DG (NPI Electronic) with cut-off frequency of 50 Hz to eliminate all closures lasting less than 20 ms including intraburst closings with characteristic life-time less than 5 ms. For kinetic analysis, the signal was digitized by Digidata 1322 (Molecular Device) with a sampling rate of 500 Hz and analyzed using pCLAMP 9.2 (Molecular Device) software. Dwell-time histograms for the open and closed states were plotted in the logarithmic binning mode and fitted by a single exponential function. The validity of the reduced two states kinetic model is evident from the single exponential fit seen for both closed and open dwell time histograms. Origin Pro 7.5 (Originlab) software was used to fit all-points histograms by multi-peak Gaussians. Single-channel current was defined as the distance between peaks on the fitting curve and used for the calculation of the single-channel conductance (D). The probability of the single channel being open (Po) was calculated as a ratio of the area under the peak for the open state to the total area under both peaks on the fitting curve.

Thermal stability of the channels was measured at 45° C.; temperatures above 50° C. affect the fluidity of the lipids used and compromise the integrity of the planar bilayer (L. A. Aleksandrov, et al., Protein expression and purification, 116 (2015) 159-166). Heating and temperature control were established by a temperature control system TC2BIP (Cell Micro Controls, Norfolk, Va., USA) with heating element covering the "trans" compartment outer side surfaces and bottom surface. Because of the bulky "trans" compartment it takes about 2-3 minutes to achieve a uniform temperature distribution across all compartments after the first indication of the expected temperature by the local temperature sensor in the chamber. We consider the thermal stability of the CFTR constructs in terms of its ability to support single channel function with stable open state conductance for the next 5 minutes after initial 5 minute incubation at the temperature of interest (L. A. Aleksandrov, et al., Protein expression and purification, 116 (2015) 159-166).

Replica-exchange molecular dynamics. REMD simulations were performed for human 6SS-NBD1 starting from the X-ray structure of RI (RI-NBD1 comprising residues 387-646 excluding a deletion of residues 405-436; PDB code 2PZE). Importantly, this is the same contract as used for the experimental work. Results for the WT construct were taken from (M. Zhenin, et al., J Chem Inf Model, 55 (2015) 2349-2364), and the same simulation protocol was followed. Prior to simulation, the 6SS mutations were introduced into WT-NBD1 using the mutation and the side-chain refinement protocols as implemented in Discovery Studio (Dassault Systemes BIOVIA, Discovery studio modeling environment, Release 4.5, San Diego, 2015) and the resulting construct was processed by the Prepare Protein protocol as implemented in Discovery Studio to set the correct protonation states for all residues at pH=7.0. All simulations were performed using the Gromacs Molecular Dynamics package version 4.5.5 (H. J. C. Berendsen, et al., Computer Physics Communications, 91 (1995) 43-56; B. Hess, et al., J Chem Theory Comput, 4 (2008), 435-447) with the OPLS/AA force field (G. A. Kaminski, et al., The Journal of Physical Chemistry B, 105 (2001) 6474-6487). Each REMD simulation consisted of 32 replicas with each replica running for 10 ns, so that the construct was simulated for a total of 960 ns (32 replicas×10 ns×3 times). Simulations covered a temperature range of 300 to 349.38 K (26.85 to 76.23° C.), a range selected to give the same acceptance probability between all adjacent pairs over the entire temperature range based on known energy distributions of solvated proteins (A. Patriksson, D. van der Spoel, Phys Chem Chem Phys, 10 (2008) 2073-2077). FIGS. 15 and 16, and Table 4 and the accompanying text provide additional details on simulation setup and convergence.

Example 2: NBD1 Stabilization by Mutagenesis

Figure 1:
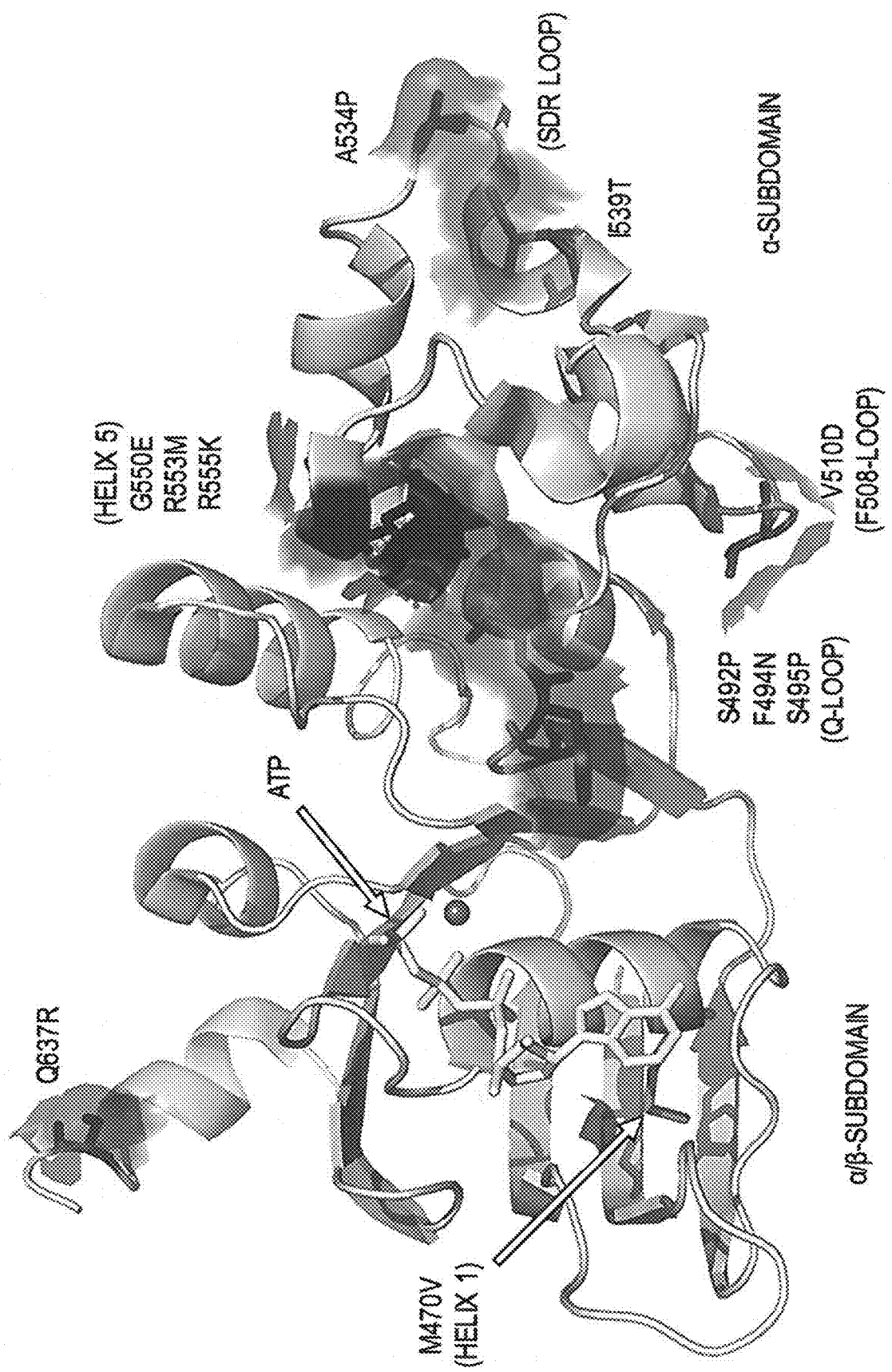
FIG. 1: Stabilizing mutations in NBD1. Crystal structure of human NBD1 (2PZE), rendered in Pymol, showing the location of mutations studied.

FIG. 1 shows the locations of the known NBD1 stabilizing mutations (L. He, et al., J Mol Biol, 427 (2015) 106-120; L. He, et al., FASEB J, 24 (2010) 3103-3112; A. A. Aleksandrov, et al., J Mol Biol, 419 (2012) 41-60; L. He, et al., J Mol Biol, 427 (2015) 106-120; H. A. Lewis, et al., J Biol Chem, 280 (2005) 1346-1353; J. L. Teem, et al., Receptors Channels, 4 (1996) 63-72; J. L. Teem, et al., Cell, 73 (1993) 335-346; A. C. DeCarvalho, et al., J Biol Chem, 277 (2002) 35896-35905). Most of these known mutations are located in the α-subdomain. As we will show, M470V located in the first helix in the α/β-subdomain (FIG. 1) is also a stabilizing mutation. The M470 polymorphism is nearly always present with the F508 mutation, compared to 50% concurrence of either M or V alleles with WT CFTR (B. M. Ciminelli, et al., J Cyst Fibros, 6 (2007) 15-22). M470-CFTR protein reportedly matures more slowly, and exhibits a 1.7-fold increased intrinsic chloride channel activity compared to V470-CFTR (H. Cuppens, et al., J Clin Invest, 101 (1998), 487-496; L. Wei, et al., FEBS Lett, 473 (2000) 149-153; R. J. Bridges, et al., Pediatr. Pulmonol., 48 (2013) 209-209.

Example 3: Single NBD1 Mutations Increase Calorimetric Tm

Figure 2:
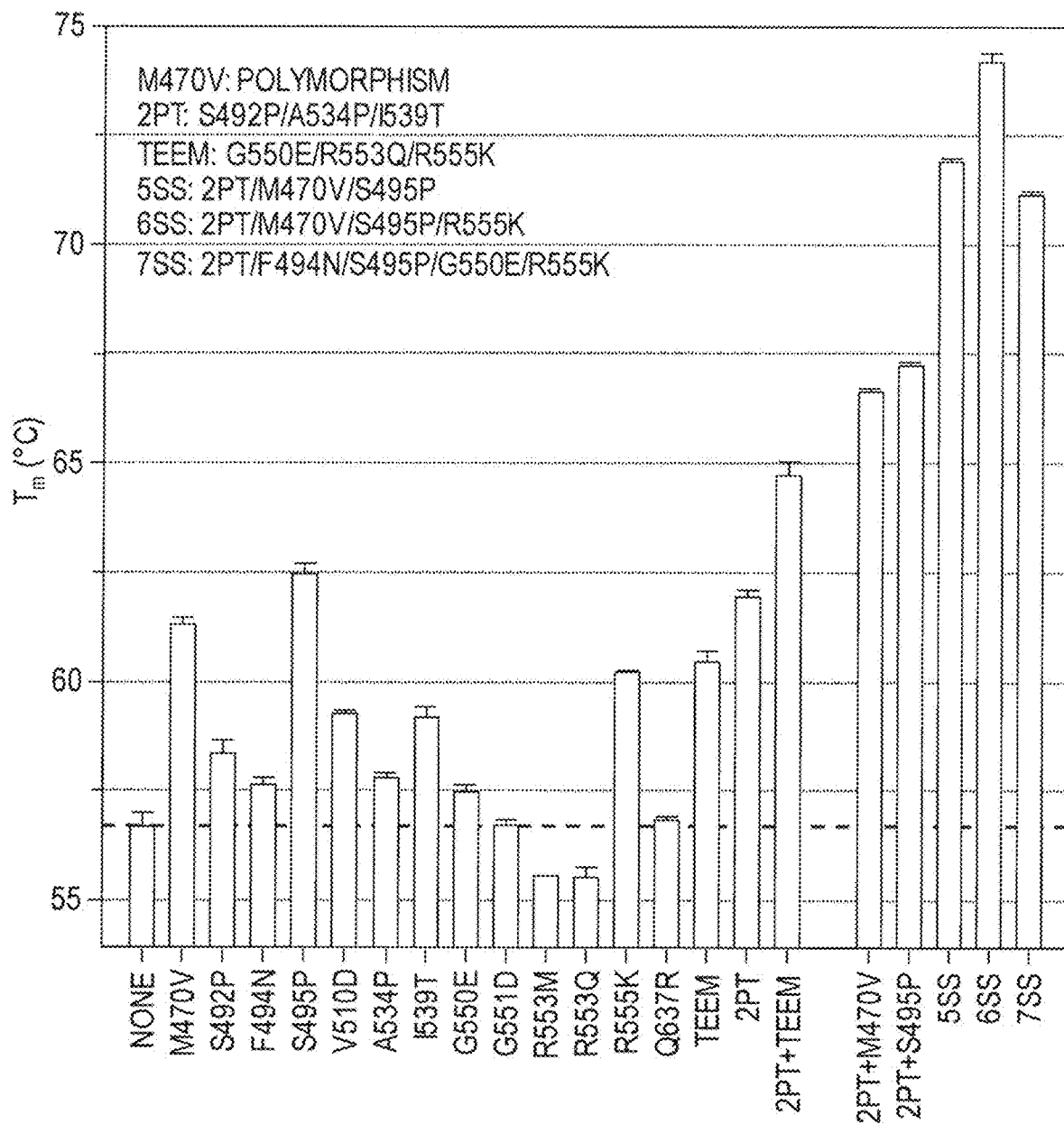
FIG. 2: Stabilization of ΔRI-NBD1 by individual and multiple mutations. Point mutations were introduced into ΔRI-NBD1 containing the WT CFTR sequence with the M470 polymorphism (named "none"), and the $T_m^{cal}$ determined as described herein. The naming was based on conventions in the CFTR field. S492P/A534P/I539T was previously named 2PT (L. He, et al., J. Mol. Biol., 427 (2015) 106-120; L. He, et al., FASEB J, 24 (2010) 3103-3112; A. A. Aleksandrov, et al., J. Mol. Biol., 419 (2012) 41-60; L. A. Aleksandrov, et al., Protein expression and purification, 116 (2015) 159-166) and G550E/R553M/R555K were discovered by Teem et al. (J. L. Teem, et al., Receptors Channels, 4 (1996) 63-72; J. L. Teem, et al., Cell, 73 (1993) 335-346; A. C. DeCarvalho, et al., J. Biol. Chem., 277 (2002) 35896-35905). New mutation combinations 5SS, 6SS, and 7SS discovered in this study were named according to the number of stabilizing substitutions (SS) introduced on top of the ΔRI (deletion of 405-436) NBD1 background. Shown are average ± range of 2 to 3 independent experiments, with $T_m^{cal}$ ranges among replicates ≤0.6° C. For some data points the error bars were so small that the bar is not seen. Data for these and additional combinations appear in FIG. 9.

We have previously applied DSC to investigate the thermodynamics and kinetics of unfolding of isolated NBD1 proteins (I. Protasevich, et al., Protein Sci, 19 (2010) 1917-1931; Z. Yang, et al., Protein Sci, 23 (2014) 769-789; Z. Yang, et al., Methods Enzymol, 567 (2016) 319-358). Here we have determined the calorimetric unfolding temperature ($T_m^{cal}$) of individual mutations in the isolated NBD1 domain, then assessed the effects of multiple NBD1 mutations (FIG. 2). We used the WT human NBD1 carrying a deletion of the 32 amino acid regulatory insertion (ΔRI-NBD1, Δ405-436) which is not present in other ABC transporters (S. Atwell, et al., Protein Eng Des Sel, 23 (2010) 375-384). ΔRI-NBD1 shows favorable solution properties and enabled the structure determinations of WT and ΔF508-NBD1 (S. Atwell, et al., Protein Eng Des Sel, 23 (2010) 375-384). We found that the M470V mutation (V470 polymorphism) strongly stabilized ΔRI-NBD1 ($T_m$ of 56.7±0.3° C., n<22), with a $\Delta T_m^{cal}$ of +4.6° C. ($T_m$ of 61.3±0.1° C., FIG. 2), an effect equal to or larger than the majority of stabilizing α-subdomain mutations, S495P gave the highest $\Delta T_m^{cal}$ of +5.8° C. ($T_m$ of 62.5±0.2° C., FIG. 2), S492P, A534P, and I539T all showed modest stabilization of NBD1 by +1.2 to 2.5° C. S495P is located in the Q-loop of the α-subdomain, a flexible loop that plays an important role in ATP binding and interacts with transmembrane domains (L. He, et al., J Mol Biol., 427 (2015) 106-120). S495P, S492P (in the same Q-loop), A534P, and I539T (FIG. 1) were originally identified from sequence alignments of CFTR orthologs (A. A. Aleksandrov, et al., J Mol Biol, 419 (2012) 41-60). A534P and I539T are in the structurally diverse region, a flexible loop that diverges in CFTR compared to other human ABC-C subfamily members (FIG. 8) (H. A. Lewis, C. et al., J Mol Biol, 396 (2010) 406-430), The well-studied Teem mutations G550E, R553M and R555K (J. L. Teem, et al., Receptors Channels, 4 (1996) 63-72; J. L. Teem, et al., Cell, 73 (1993) 335-346; A. C. DeCarvalho, et al., J Biol Chem, 277 (2002) 35896-35905) are located in Helix 5 that overlaps the Signature motif LSGGQ (SEQ ID NO:3) (FIGS. 1 and 8). These mutations stabilized NBD1 to varying degrees, with R555K imparting the greatest $\Delta T_m^{cal}$ of +3.5° C. ($T_m$ of 60.22±0.01° C., FIG. 2). Introducing the interface mutation V510D into the flexible loop that contains F508 (I. Protasevich, Z. Yang. C. Wang, S. Atwell, X. Zhao, S. Emtage, D. Wetmore, J. F. Hunt, C. G. Brouillette, Protein Sri, 19 (2010) 1917-1931) improved NBD1 thermal stability by +2.6° C. The so-called solubilizing imitations identified from X-ray crystallography (H. A. Lewis, et al., J Biol Chem, 280 (2005) 1346-1353; H. A. Lewis, et al., J Mol Biol, 396 (2010) 406-430), F494N in the Q-loop and Q637R near the unstructured C-terminus (FIG. 1), produced only small $\Delta T_m^{cal}$ in $\Delta$RI-NBD1 (FIG. 2).

Example 4: $T_m^{cal}$ of Combinations of Known NBD1 Mutations

Figure 9:
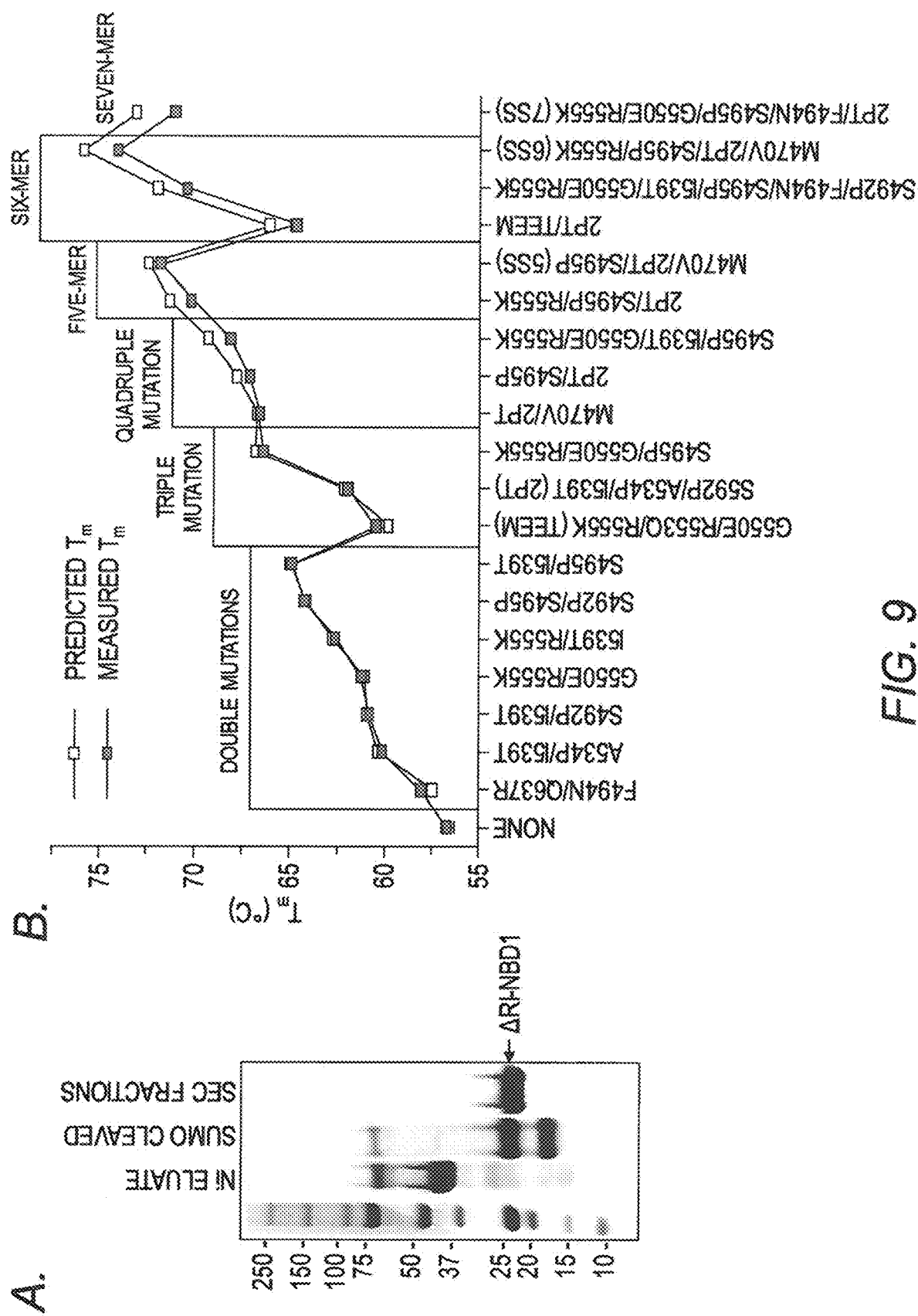
FIG. 9: Additivity of stabilizing effects of mutations in NBD1. PANEL (A) ΔRI-NBD1 containing the M470 polymorphism was purified from *E. coli* by Ni-NTA affinity chromatography, the Sumo-fusion protein cleaved with TEV, and the domain isolated by size exclusion chromatography (SEC). Mutations were introduced into ΔRI-NBD1, and the measured $T_m^{cal}$ of the purified domain determined by DSC. Double mutations that stabilized >4° C. were combined with another mutation to yield triple mutations; triple mutations that stabilized >6° C. were in turn combined with another mutation to generate quadruple mutations. Means of 2 to 3 replicates are given as error bars (most are smaller than the symbol sizes). $T_m^{cal}$ predictions were obtained by adding the $\Delta T_m^{cal}$s single mutations. Measured $T_m^{cal}$s of up to three mutations generally matched those predicted based on $T_m^{cal}$s of the single mutations, and somewhat overestimated $\Delta T_m^{cal}$ for larger combinations.

A limited number of mutation combinations were previously shown to increase thermal stability of NBD1 in an additive manner, and to improve biogenesis of full-length $\Delta$F508-CFTR (L. He, et al., J Mol Biol, 427 (2015) 106-120). For example, combining the three mutations S492P/A534P/I539T (2PT) with G550E/R553M/R555K (Teem), restored maturation of $\Delta$F508-CFTR to ~90% of the WT. The $T_m^{cal}$ of $\Delta$RI-NBD1 containing these 6 mutations was +8.0° C. higher than $\Delta$RI-NBD1 ($T_m^{cal}$ of 64.7±0.3° C., 2PT/Teem, FIG. 2). Summing individual $\Delta T_m^{cal}$ for single mutations predicted reasonably well the stabilization effects for combinations of up to three mutations in $\Delta$RI-NBD1, and somewhat overestimated the $\Delta T_m^{cal}$ for larger combinations (FIG. 9). Summation would predict a $\Delta T_m^{cal}$ of +8.9° C. for the six-mutation 2PT/Teem combination, a fairly good estimation of the measured $\Delta T_m^{cal}$ of 8.0° C. Interestingly, when 2PT/Teem was introduced into $\Delta$F508-NBD1, the observed $\Delta T_m^{cal}$ of +10.7° C. was even larger than predicted by summation (data not shown). Therefore, we examined whether strategic mutations with strong stabilizing effects may be combined to maximally stabilize NBD1.

Example 5: Maximizing Thermal Stability of NBD1 by Strategic Combinations of Mutations Building on the success of $\Delta$RI/2PT/Teem, we attempted to generate a "super-stabilized" NBD by adding two other Q-loop mutations, F494N and S495P, and omitting the ineffective R553M (7SS with a total of seven mutations, FIG. 2). 7SS-NBD1 (2PT/F494N/S495P/G550E/R555K) exhibited a much improved $T_m^{cal}$ of 71.1±0.05° C. (+14.4° C. over $\Delta$RI-NBD1 and +6.4° C. over 2PT/Teem). Additionally, in order to maximally improve thermal stability with the fewest mutations, $\Delta$RI-NBD1 was progressively and systematically modified with two or more of S492P, A534P, or I539T along with the strongest single mutations M470V, S495P or R555K (FIG. 9). This process led to 5SS- and 6SS-NBD1 containing five and six of the most stabilizing single mutations, respectively. The 5SS-NBD1 (2PT/M470V/S495P) registered a $T_m^{cal}$ of 71.8±0.05° C. ($\Delta T_m^{cal}$ of +15.1° C., FIG. 2). 6SS-NBD1 (2PT/M470V/S495P/R555K) was the most stable combination of all, with a $T_m^{cal}$ of 74.2±0.2° C. ($\Delta T_m^{cal}$ of +17.5° C., FIG. 2). Thus our strategic and iterative testing of combinations of mutations succeeded in identifying several NBD1 variants with greatly improved thermal stability.

Example 6: Mammalian Cells Produce Mature Full-Length CFTR Variants with Stabilizing Mutations Based on previous studies (L. He, et al., J Mol Biol, 427 (2015) 106-120; L. A. Aleksandrov, et al., Protein expression and purification, 116 (2015) 159-166), the stabilized NBD1 variants identified above may be expected to favor folding and trafficking of full-length CFTR to the plasma membrane in a mammalian expression system. We introduced a series of mutation combinations shown to increase NBD1 stability into a previously described human CFTR construct, $His_{10}$-Sumo*-CFTR$^{FLAG}$-EGFP (E. Hildebrandt, et al., Mol Biotechnol, 57 (2015) 391-405), and also deleted RI ($\Delta$405-436). Positioning the FLAG epitope into the fourth extracellular loop of CFTR enabled reliable cell-surface compartmentalization by flow cytometry. The RI deletion is known to rescue maturation, stability and function of full-length $\Delta$F508-CFTR, and to enhance channel activity of CFTR at the cell membrane (A. A. Aleksandrov, et al., J Mol Biol, 419 (2012) 41-60). All combination mutations that were expressed in full-length CFTR are summarized in Table 1, together with their short name and cell line designation. Comparisons of expressions levels among cell lines suggested that surface CFTR expression increased in the RI-CFTR and RI/2PT-CFTR mutations (cell lines D992 and D994, FIG. 10) compared to WT (Jensen, A. E., et al., J Mol Biol, 419 (2012) 41-60). However, when RI/2PT-CFTR was combined with additional mutations as in 5SS-(D1012), 6SS-(D1013) or 6SS/H1402S-CFTR (D1028), surface CFTR expression was not further increased. On the other hand, CFTR expression could be increased by other tet-on strategies (Table 3 and FIG. 11). Importantly, all cell lines produced fully mature and glycosylated CFTR (FIG. 3A, band C), suggesting that, even in the most highly expressing cell lines (D1013 and D1028, FIG. 10), the majority of CFTR protein passed quality control in the endoplasmic reticulum, and trafficked normally to the plasma membrane. Thus WT and stabilized CFTR variants provided excellent source material for production of purified CFTR.

Example 7: Stabilized CFTR Variants Retain ATPase Function

Figure 4:
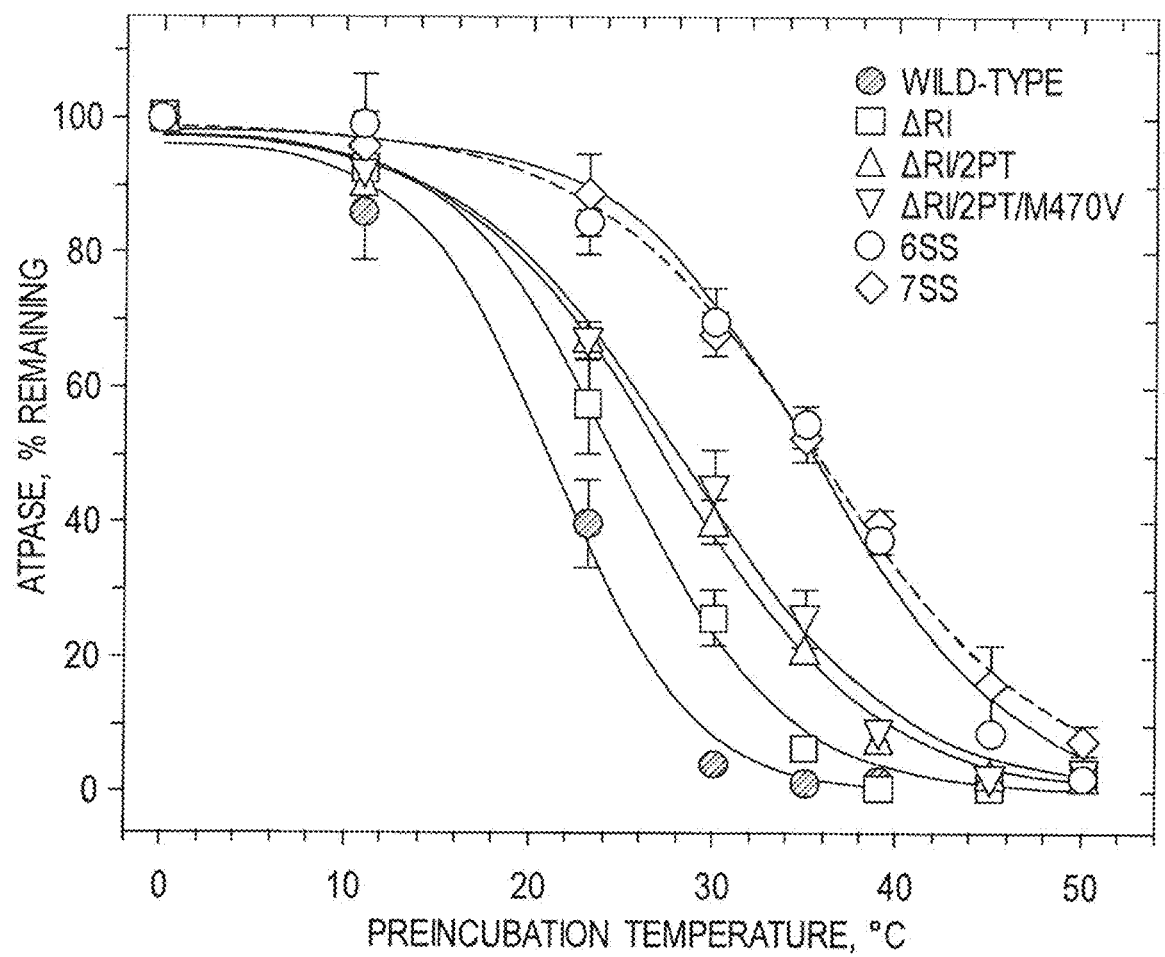
FIG. 4: Stabilization of NBD1 in CFTR increases the inactivation threshold for ATP hydrolysis, $T_m^{func}$. Purified CFTR was pre-incubated for 30 min in the absence of lipid or nucleotide over a range of temperatures, then ATPase activity remaining was measured. In each experiment, the least squares sigmoidal fit was used to derive the inflection point defined as the functional $T_m \cdot T_m^{func}$ was measured 3 to 4 times for each mutant, and a statistical comparison is given in Table 1. This plot shows averages ±standard deviations of data combined from the replicate experiments.

We previously demonstrated that phosphorylated, highly purified CFTR from HEK or CHO cells and supplemented with phosphatidylserine hydrolyzes ATP at rates comparable to other ABC transporters (E. Hildebrandt, et al., Biochimica Et Biophysica Acta-Biomembranes, 1859 (2017) 289-293; E. Hildebrandt, et al., Biochim Biophys Acta, 1838 (2014) 2825-2837). Not unexpectedly, rates of ATP hydrolysis were altered when multiple NBD1 mutations were introduced (FIG. 3, Panel B). ATPase activity of RI/2PT-CFTR increased 2-fold over WT, and the highest activity was exhibited by the RI/2PT/M470V-CFTR variant. In many cases the activity was reduced but still readily measurable. Although activities of 5SS-, 6SS- and 7SS-CFTR variants were similar to WT, they were substantially reduced compared to RI/2PT/M470V-CFTR, probably due to the presence of additional mutations in the Q-loop (S495P) or the Signature sequence (G550E and R555K, FIG. 1). In contrast, activity was abolished by negative control mutations of NBD2 residue H1402 (FIG. 4, D869, D872), the switch histidine which interacts with MgATP and bound $H_2O$ at the catalytic center (D. C. Gadsby, et al., Nature, 440 (2006) 477-483). Mutations of H1402 also abolish ATP-dependent channel gating by locking CFTR in an open channel conformations (L. A. Aleksandrov, et al., Protein expression and purification, 116 (2015) 159-166). NBD1-stabilization translates to functional stabilization of CFTR. To evaluate the biophysical properties of the purified protein in detergent solution, we determined a functional half-life at different temperatures, and global unfolding of the protein by differential scanning fluorimetry. A 30 min heat treatment of each purified protein was used to determine the transition temperature for the inactivation of ATP hydrolytic activity as shown in FIG. 4, which we have defined as the functional $T_m$ (or half-life referred to here as $T_m^{func}$) (E. Hildebrandt, N. Khazanov, J. C. Kappes, Q. Dai, H. Senderowitz, I. L. Urbatsch, Biochimica Et Biophysica Acta-Biomembranes, 1859 (2017) 289-293). $T_m^{func}$ was 22° C. for WT CFTR purified from either CHO or HEK cells (FIG. 4, Panel B, black circles, Table 1). Deletion of the RI (D359) produced a small but significant thermal stabilization (Table 1). RI/2PT mutations (D727) or RI/M470V/2PT (D851) further shifted the $T_m^{func}$ to 28° C. Notably, although M470V significantly stabilized the $T_m^{cal}$ of the isolated RI-NBD1 and RI/2PT-NBD1 mutant combinations tested by DSC by ~5° C. (FIG. 2), a shift in the $T_m^{func}$ of less than 1° C. was observed in full-length CFTR (p=0.322, Table 1). The most significant stabilization was observed with the 6SS (D1013) and 7SS (D744) that shifted $T_m^{func}$ by +12° C. to 35.7° C. (FIG. 4 and Table 1). $T_m^{cal}$ correlated strongly with $T_m^{func}$ as shown in FIG. 5A. The data show that progressive stabilization of the NBD1 domain translates into thermal stabilization of NBD function in the purified full-length protein.

Example 8: NBD1-Stabilizing Mutations Also Thermally Stabilize Full-Length CFTR

Figure 5:
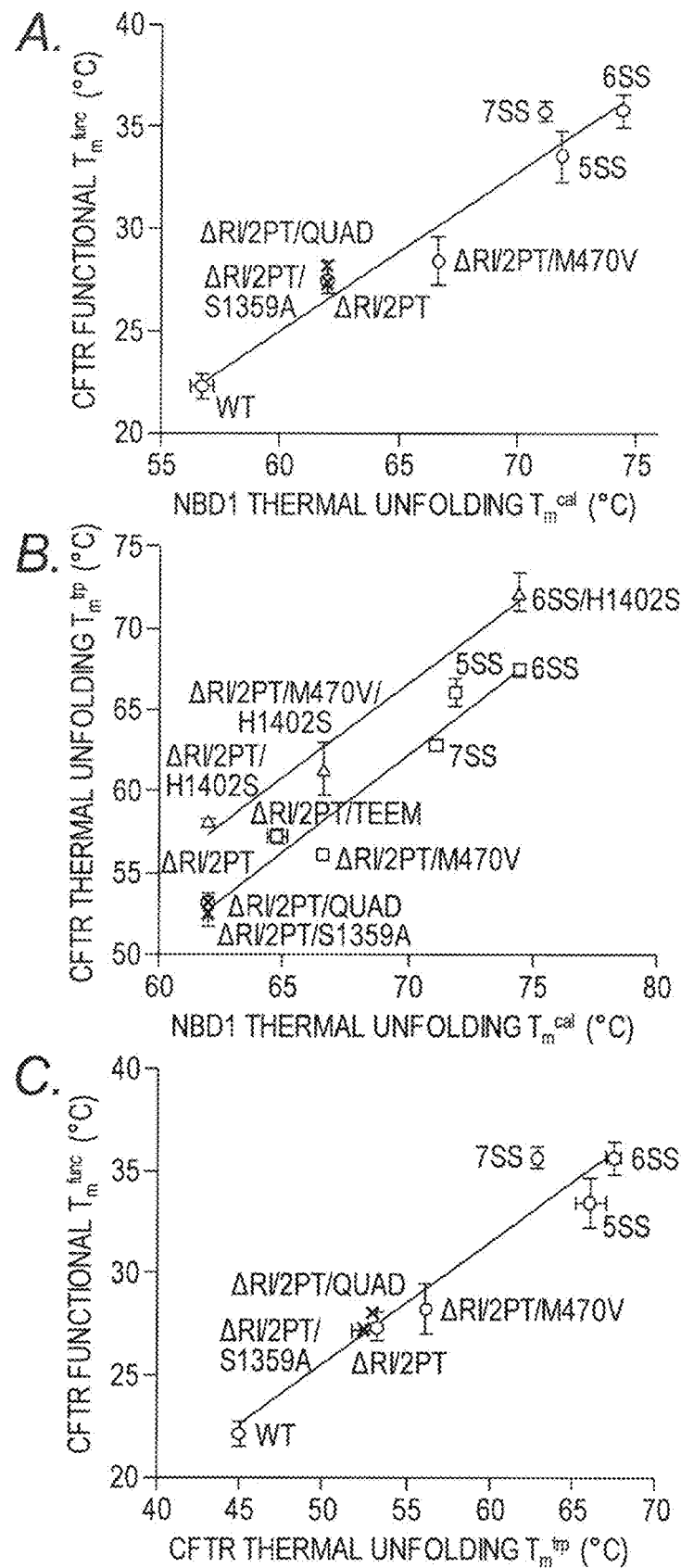
FIG. 5: NBD1 thermal stability directly correlates with thermal stability of full-length CFTR functional and thermal stabilities. For each combination of mutations, PANEL (A) $T_m^{func}$ or PANEL (B) $T_m^{trp}$ for unfolding of purified full length CFTR in detergent solution by intrinsic fluorescence is plotted against $T_m^{cal}$ for NBD1 unfolding obtained by DSC (FIG. 2). Pearson correlation coefficients were 0.972 for the 6 constructs containing only the NBD1 mutations (solid line), and 0.986 for the 3 constructs containing NBD1 mutations plus H1402S (dashed line). PANEL (C) Correlation between $T_m^{trp}$ for CFTR unfolding (FIG. 12) and $T_m^{func}$ for ATPase inactivation (FIG. 4). The Pearson correlation coefficient was 0.966. See Table 1 for mutation nomenclature. Note that the $T_m^{func}$ is lower than $T_m^{trp}$ likely because of the long exposure time of 30 min at a fixed temperature in the absence of protective MgATP compared to a continuous ramp of 1° C./min used in Trp unfolding experiments.

Tryptophan (Trp) fluorescence is sensitive to environment, and protein unfolding can often be monitored by changes in fluorescence intensity and sometimes changes in the emission maximum wavelength ($\lambda_{max}$) (Z. Yang, et al., Methods Enzymol, 567 (2016) 319-358). In the folded state at 10° C., CFTR showed a λ of 334 nm (data not shown), consistent with the majority of detected Trps being in a hydrophobic environment. A representative trace of intrinsic fluorescence vs. temperature is shown in FIG. 13. ΔRI/2PT-CFTR and other stabilized variants all exhibited a single sigmoidal unfolding transition in fluorescence intensity at a characteristic temperature (FIG. 5). A single transition is not unusual for multidomain proteins that cooperatively unfold (C. A. Royer, Chem Rev, 106 (2006) 1769-1784). The $T_m^{trp}$ was 53.2±0.1° C. for RI/2PT-CFTR, increasing to 56.2±0.2° C. in the RI/2PT/M470V (D851) mutant and to 67.4±0.4° C. for the most stable 6SS. The H1402S mutation, which abolished ATP hydrolysis (FIG. 3), in combination with RI/2PT or with RI/2PT/M470V or 6SS, consistently improved CFTR thermal stability by +5.0±0.2° C. (FIG. 5, Panel B, solid triangles). This finding is in agreement with proposed NBD dimerization due to occlusion of putatively non-hydrolyzed MgATP, which imposes a locked open channel conformation (L. A. Aleksandrov, et al., Protein expression and purification, 116 (2015) 159-166).

For CFTR mutants containing only the NBD1-stabilizing mutations, $T_m^{trp}$ of full length CFTR correlated strongly with the $T_m^{cal}$ of isolated NBD1 obtained by DSC (FIG. 5, Panel B, solid line). The same positive correlation was observed in the presence of the additional increment in CFTR stability from H1402S in NBD2 (FIG. 5, Panel B, gray line). The data are consistent with NBD1 stability being an important determinant of CFTR stability with other regions of the protein also contributing to protein stability. $T_m^{func}$ also correlated strongly with $T_m^{trp}$ (FIG. 5, Panel C, solid line) with overall lower values seen for $T_m^{func}$, because the longer incubation time (30 minutes) at each temperature had the same effect as an extremely slow heating rate, which results in lower apparent $T_m$ (J. M. Sanchez-Ruiz, et al., Biophys J, 61 (1992) 921-935). However, among the super-stabilized CFTR variants, we noted a difference in rank order of stability between $T_m^{trp}$ (7SS<5SS<6SS) and $T_m^{func}$ (5SS<7SS<6SS, Table 1), suggesting that loss of enzymatic activity might occur prior to cooperative unfolding.

Example 9: Stabilized CFTR Variants Retain Channel Function

Figure 6:
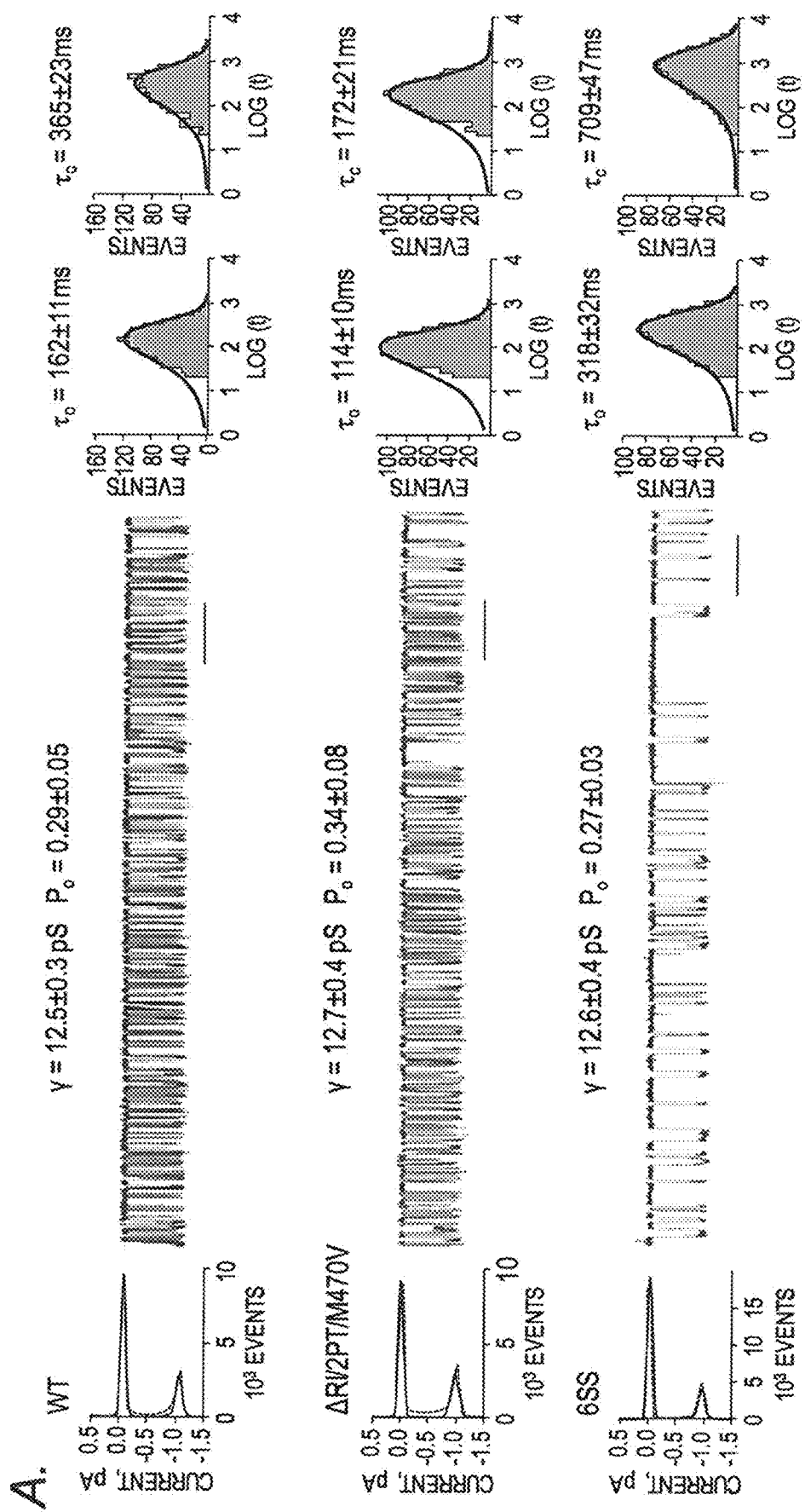
FIG. 6: Single channel recordings of stabilized CFTR mutants. PANEL (A) Examples of single-channel current recordings in membranes isolated from CHO cells expressing either WT CFTR (D507, top trace), or FTR containing four (ΔRI/2PT/M470V, D851, middle trace) or six stabilizing mutations (6SS, D1013, bottom trace). Channels were recorded at 33° C. with 0.3 mM ATP after phosphorylation with protein kinase A. All-point histograms (plots at left) were used to calculate single channel conductance γ as a distance between peaks, and Po as a ratio of the area under the peals. The values of mean open ($\tau_o$) and mean closed times ($\tau_c$) for the particular examples shown were calculated from the dwell-time histograms (plots at the right). Experiments were repeated 6 times with a total recording time of 48 min for WT, 5 times and 42 min for 2PT/M470V, or 4 times and 52 min for 6SS-CFTR. Averages and SEM of unitary channel parameters are given in Table 2. PANEL (B) Bar graph of gating cycle duration (τo+τc). PANEL (C) Single channel function recorded for 1 min after 9 min exposure at elevated temperature. Under these conditions, the WT ceased gating and remained closed, while 6SS-CFTR retained stable gating.
Figure 6:
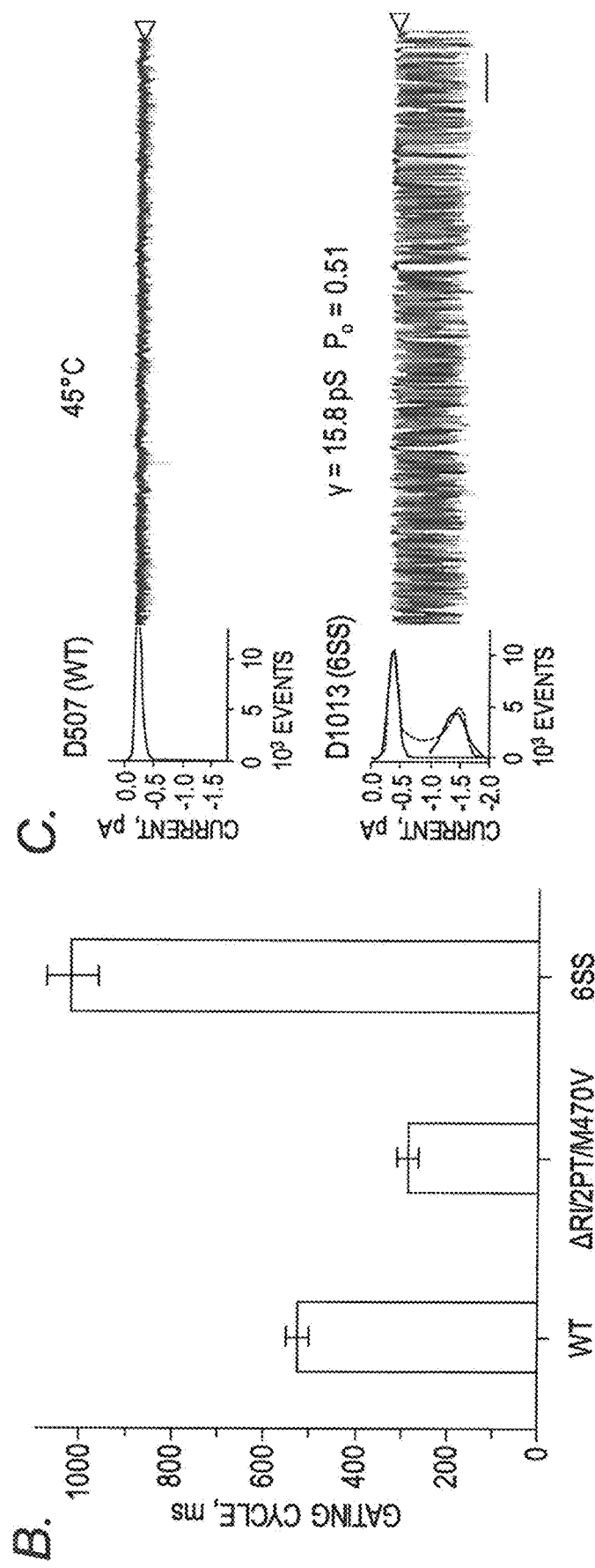

CFTR is an ATP-gated anion channel whose function is to transport chloride and bicarbonate across the membrane (J. R. Riordan, et al., Annu Rev Biochem, 77 (2008) 701-726). Thus, the most decisive functional assessment is anion transport (A. A. Aleksandrov, et al., J Physiol, 587 (2009) 2875-2886; L. Cui, et al., J Physiol, 572 (2006) 347-358). To analyze whether and how the properties of the stabilized CFTR channels might have been altered, we recorded single channels in planar lipid bilayers (A. A. Aleksandrov, et al., FEBS Lett, 431 (1998) 97-101). Recordings of selected CFTR variants, driven by the same concentration of 0.3 mM ATP and at a temperature of 33° C. comparable to conditions of the ATPase assays, and ion channels parameters are shown on FIG. 6, Panel A. Wt CFTR containing the three Sumo, 901-Flag, and EGFP tags expressed in CHO cells exhibited single channel conductance γ of 12.5±0.3 pS (n=6) with an open probability $P_o$ of 0.29±0.05 (n=6) (FIG. 6A upper trace) similar to WT CFTR containing the same tags expressed in HEK cells (E. Hildebrandt, et al., Mol Biotechnol, 57 (2015) 391-405). Introducing the ΔRI/2PT/M470V-CFTR variant containing the M470V polymorphism (FIG. 6A, middle trace) had a single channel conductance γ of 12.7±0.4 pS (n=5) and probability $P_o$ of 0.34±0.08 (n=5) not statistically different from WT (Table 2). This CFTR variant showed a somewhat reduced the dwell-time for the mean open ($\tau_o$=114±ms) and the mean closed time ($\tau_c$=172 ms), and so shortened $\tau_{cycle}$ to 286 ms compared to WT CFTR (FIG. 6, Panel B). The most stable 6SS-CFTR variant, expressed in CHO cells, also displayed gating properties very similar to the WT-CFTR (γ of 12.6±0.4 pS (n=5), $P_o$ of 0.27±0.03), except that both the dwell-times for the mean open ($\tau_o$=318 ms) and closed times ($\tau_c$=709 ms) were somewhat prolonged, leading to a prolonged gating cycle duration (FIG. 6, Panel B).

TABLE 2

Single channel conductance parameters

| | Conductance (pSi) | Po | n | P value | τo (ms) | τc (ms) | τo + τc (ms) | P value |
|---|---|---|---|---|---|---|---|---|
| WT CFTR | 12.5 ± 0.3 | 0.29 ± 0.05 | 6 | | 162 ± 11 | 365 ± 23 | 527 ± 25 | |
| ΔRI/2PT/M470V | 12.7 ± 0.4 | 0.34 ± 0.08 | 5 | ns | 114 ± 10 | 172 ± 21 | 286 ± 23 | <0.0001 |
| 6SS-CFTR | 12.6 ± 0.4 | 0.27 ± 0.03 | 4 | ns | 318 ± 32 | 709 ± 47 | 1027 ± 57 | <0.0001 |

To assess the thermal sensitivity, single channels were recorded at 45° C., a temperature at which we previously demonstrated that WT CFTR was rapidly inactivated within 2 to 3 min, the time required to reach uniform temperature across all compartments of the bilayer apparatus as previously described (L. A. Aleksandrov, et al., Protein expression and purification, 116 (2015) 159-166). The top panel in FIG. 6, Panel C shows a trace of WT-CFTR microsomal membranes fused with the bilayer after 5 min incubation at 45° C. which virtually abolished channel gating. In contrast, 6SS-CFTR actively gated for at least 20 min. The stable channel 1 activity of 6SS-CFTR in lipid membranes thus corroborates the increased thermal ($T_m^{trp}$) and functional stability ($T_m^{func}$) of this protein in detergent solution.

beta-sheets), and seven are in less structured positions (e.g. coil regions) (FIG. 1). We attempted to predict the stabilizing effect of single mutations as well as for the combination of mutations present in the 6SS construct using descriptors such as Solvent Accessible Surface Area (SASA), B-factor and calculated G values, but correlations with our experimentally determined data were weak (FIG. 14). On the other hand, we previously demonstrated a correlation between root mean squared fluctuations (RMSF) profiles derived from replica exchange molecular dynamics (REMD) simulations and thermal stabilities for a set of NBD1 mutants (M. Zhenin, et al., J Chem Inf Model, 55 (2015) 2349-2364). To

TABLE 1

Mutations that improve NBD1 stability also improve thermal stability of the ATPase activity.

| | | Cell | $T_m^{Trp}$ (° C.) | | | $T_m^{func}$ (° C.) | | | P value [3] | | |
|---|---|---|---|---|---|---|---|---|---|---|---|
| | short name | line [1] | mean | range | n | mean | sd | n | vs WT | vs 2PT | vs 7SS |
| WT (HEK) | | D165 [2] | | | | 21.55 | 0.53 | 3 | ns | | |
| WT (CHO) | | D421 | | | | 22.23 | 0.55 | 3 | | | |
| NBD1 mutations: | | | | | | | | | | | |
| ΔRI (HEK) | | D359 | | | | 24.64 | 1.34 | 3 | 0.0449 | 0.0311 | |
| ΔRI/S492P/A534P/I539T (CHO) | 2PT | D727 | 53.2 | 0.2 | 2 | 27.41 | 0.61 | 3 | 0.0004 | | |
| ΔRI/2PT/M470V (CHO) | | D851 | 56.1 | 0.4 | 2 | 28.27 | 1.17 | 3 | 0.0013 | ns | |
| ΔRI/2PT/M470V/S495P (CHO) | 5SS | D1012 | 66.0 | 1.3 | 3 | 33.50 | 1.23 | 4 | <.0001 | 0.0006 | 0.0369 |
| ΔRI/2PT/M470V/S495P/R555K (CHO) | 6SS | D1013 | 67.4 | 0.7 | 3 | 35.72 | 0.75 | 3 | <.0001 | 0.0001 | ns |
| ΔRI/2PT/F494N/S495P/G550E/R555K | 7SS | D744 | 62.8 | 0.6 | 4 | 35.65 | 0.46 | 3 | <.0001 | <.0001 | |
| NBD2 mutations: | | | | | | | | | | | |
| ΔRI/2PT/H1402S (CHO) | | D869 | 58.2 | 0.1 | 2 | Inactive [4] | | | | | |
| ΔRI/2PT/M470V/H1402S (CHO) | | D872 | 61.3 | 1.6 | 8 | Inactive [4] | | | | | |
| ΔRI/6SS/H1402S (CHO) | 6SS/ H1402S | D1028 | 72.2 | 1.1 | 3 | inactive [4] | | | | | |
| ΔRI/2PT/S1359A (CHO) | | D805 | 52.5 | 1.2 | 3 | 27.24 | 0.10 | 3 | 0.0001 | ns | <.0001 |
| ΔRI/7SS/S1359A (CHO) | | D804 | | | | 31.32 | 1.00 | 3 | 0.0002 | 0.0044 | 0.0024 |
| ΔRI/2PT/S1255L/K1334G/S1359A/ Q1411D (CHO) | 2PT/quad | D742 | 53.0 | 1.1 | 3 | 28.07 | 0.18 | 3 | <.0001 | ns | |
| ΔRI/7SS/S1255L/K1334G/S1359A/ Q1411D (CHO) | 7SS/quad | D743 | | | | low activity | | | | | |

[1] Cell line designation is given to facilitate future sample distribution.
[2] D165 is the HEK cell line expressing WT CFTR.
[3] $T_m^{func}$ values were compared using the two-tailed student T-test. ns: P > 0.05
[4] H1402S variants showed less than 2% of WT CFTR activity Example 10: Select NBD2-Stabilizing Mutations Did not Stabilize Full-Length CFTR We also explored mutations in NBD2 (S1359A, and the quadruplet mutations S1255LIK1334G/S1359A/Q14110 that were recently discovered to significantly improve NBD2 thermal stability. Introducing these NBD2-stabilizing mutations into either ΔRI/2PT (cell line D805, D742) or the 7SS (D804, D743) had no effect on $T_m^{trp}$ (FIG. 5, Panel B, crosses). These mutants exhibited slower but (in some cases) still measurable rates of ATP hydrolysis (FIG. 3). S1359A had no effect on $T_m^{func}$ in the context of RI/2PT, but substantially reduced $T_m^{func}$ in the context of 7SS (Table 1), suggesting the loss of a stabilizing interaction in the latter case. The data are in agreement with expression and processing data reported previously (R. M. Vernon, et al., J Biol Chem, (2017)), and suggest that full length CFTR thermal stability is not limited by the stability of the NBD2 domain, but instead contacts with NBD2 residues may play a role.

Example 11: Molecular Dynamics Simulations Suggest Lower Fluctuations in the Stabilized 6SS-NBD1

Four of the NBD1 residues mutated in this study are located in structured positions (alpha-helices, turns, and test whether this correlation extends to the present set of mutations, we conducted REMD simulations for the most thermally stable NBD1 construct in this work, 6SS (FIG. 6). In these simulations the mutant construct exhibited reduced fluctuations in several regions, particularly in the 528-550 region containing A534P and I539T (in the SDR). In addition, small reductions in fluctuation were consistently observed (n=3) at positions 470 and 495 (Q-loop) corresponding to the two most stabilizing mutations (M470V, $\Delta T_m^{cal}$=4.98° C.; S495P, $\Delta T_m^{cal}$=6.1° C.). Of note, visual inspection of the crystal structure suggests that Val sits in this position more "comfortably" than Met, i.e. with less steric hindrance. Lastly, we observed no differences in fluctuation for the third most stabilizing mutation, R555K. However, for this position we compared the average distance between the side chain center of mass and that of residue 0529 in the MD trajectories. We found this distance to be smaller for K555 in 6SS (0.51±0.05 nm) than for the R555 in WT (0.57±0.05 nm) indicating better electrostatic interactions in the mutant, in agreement with experimentally observed stabilization. Thus, RMSF again proved to be a reliable predictor of experimentally observed stabilizing effects when applied to this new set of NBD1 mutations.

Example 12: Expression Platform Strategies to Enhance CFTR Production

To evaluate whether CFTR expression could be increased in this expression system by other strategies, we analyzed different TRE promotors and reverse tet transcription activators (FIG. 11). ΔRI/2PT CFTR was expressed in three cell lines: (i) D727 under control of the doxycycline-inducible TRE-tight promoter with conventional reverse tet repressor rtTA (parental cell line D389); (ii) D727.1 controlled by TRE-tight with 3G-matched rtTA transcription activator (S. Urlinger, et al., Proc Natl Acad Sci USA, 97 (2000) 7963-7968; E. P. Go, et al., J. Virol., 89 (2015) 8245-8257) parental cell line D896); and (iii) D994 under the control of doxycycline-inducible second generation promoter TRE.2 with the 3G transactivator; Table 3. Among these ΔRI/2PT cell lines, there was a strong increase in surface CFTR expression with the 3G-matched rtTA transcription activator (D896) (FIG. 11). Consequently, we used these platforms for CFTR production in the 5SS, 6SS, and 6SS/H1402S cell lines (D1012, D1013 and D1028 (Table 3). Cell lines D851, D917c, D928c, and D930c were earlier editions under the original TRE-tight promoter with the conventional tet repressor (parental cell line D389).

Example 13: Thermal Unfolding of Full-Length CFTR

The fluorescence data were normalized with respect to the pre- and post-transition baselines based on the following formula: fraction of unfolding=(fluorescence signal at temperature T−signal of native state at T)/(signal of unfolded state at T−signal of native state at T), where the signal of native state was extrapolated from the linear fit of the pre-transition baseline, and the signal of unfolded state was extrapolated from the linear fit of the post-transition baseline. The $T_m^{Trp}$ of ΔRI-NBD1 in the DSC buffer was identical to its $T_m^{Cal}$ determined by DSC (FIG. 13). Upon changing into Tris buffer containing FA-4 (used for full-length CFTR), the $T_m^{Trp}$ of ΔRI-NBD1 was reduced by 2° C. The same reduction in $T_m^{Trp}$ due to change in buffer condition was observed for all the NBD1 mutants tested. Therefore, the $T_m$-shift of each mutant remained the same in these two different buffering systems.

Example 14: Structure-Based Computations to Correlate NBD1 $T_m^{cal}$-Shifts with Structural Parameters FoldX (J. Schymkowitz, Nucleic Acids Res, 33 (2005) W382-388) was applied to predict thermodynamic stability of the mutations considered in this work. FoldX calculates ΔΔG values between a mutant and WI protein through an empirical force field approach using summation over energy terms (e.g., van der Waals interactions, hydrogen bonding, electrostatics, solvation, and entropy estimation), each weighted by an empirically determined factor. Predictions have been validated using experimentally determined ΔΔG values for a large set of mutations taken from multiple proteins (R. Guerois, et al., J Mol Biol, 320 (2002) 369-387; J. W. Schymkowitz, et al., Proc Natl Acad Sci USA, 102 (2005) 10147-10152.

FoldX computation of ΔΔG values—CFTR NBD1 structure (2PZE) including ATP and a $Mg^{2+}$ ion was prepared by the Prepare Protein protocol as implemented in Discovery Studio (BIOVIA Discovery Studio Modeling Environment, Release 2016, San Diego, 2016). Incomplete residues were fixed, missing loop regions were modeled, and the protonated states of titratable residues were set based on predicted $pK_a$ values. The structure was then optimized using the repair function of FoldX to remove any steric clashes. Mutations were introduced by the BuildModel function. We performed 10 runs for each mutation to ensure that the algorithm had indeed achieved convergence, even for large residues with many rotamers. Thus, each mutation was characterized by an average ΔΔG value across all runs.

Other computation methods—B-factors were obtained from PDB file 2PZE. SASA were calculated from the PDB file using NACCESS (S. Hubbard, et al., University College London, 1993).

Results—No clear correlation was observed between $T_m^{cal}$-shifts ($\Delta T_m^{cal}$) and ΔΔG, B-factors, or solvent accessible surface areas (SASA). Still, six of the nine most stabilizing individual mutations considered in this work ($\Delta T_m^{Cal}>1°$ C.) demonstrated negative ΔΔG FoldX values. Lack of correlation with FoldX results could be attributed to two main reasons: (1) the FoldX force field was primarily developed based on destabilizing mutations and (2) the $\Delta T_m$ range of the stabilizing mutations is small (6° C.). In agreement with this proposition, adding to the analysis a set of DSC-derived $T_m^{cal}$ values for destabilizing NBD1 mutations has provided a ΔΔG vs. ΔT correlation coefficient>0.6 and a quantitative success rate of 83% in predicting stabilizing/destabilizing mutations.

Example 15: REMD Protocol

REMD simulations were performed for human 6SS ΔRI-NBD1 (comprising residues 387-646 and excluding residues 405-436 with no additional solubilizing mutations, PDB entry 2PZE). This structure was solved in the presence of ATP and a $Mg^{+2}$ ion at 1.7 Å resolution. Prior to simulations, the protein was prepared using the Prepare Protein protocol in Discovery studio (BIOVIA, Dassault Systèmes: Discovery studio modeling environment, Release 4.5, San Diego, (2015)). This protocol inserts missing atoms in incomplete residues, models missing loop regions (in this case the Q637-P638 loop) and sets the protonation state of titratable residues based on predicted pKa values. ATP parameters for the OPLS/AA force field were parsed from the OPLS/AA 2001 force field parameters in Schrodinger (Schrödinger, Maestro: Schrödinger, LLC, New York, N.Y., (Release 2016)). The parameters for the $Mg^{+2}$ ion are included in the GROMACS implementation of this force field. The 6SS mutations were introduced into the WT background by mutating the relevant residues in 2PZE using Discovery Studio. Mutated residues and their five Å neighboring residues were optimized using the side-chain refinement protocol in Discovery Studio.

REMD simulations were performed with the Gromacs Molecular Dynamics package version 4.5.5 (B. Hess, et al., J Chem Theory Comput, 4 (2008) 435-447; H. J. C. Berendsen, et al., Computer Physics Communications, 91 (1995) 43-56) using the OPLS/AA force field (G. A. Kaminski, et al., The Journal of Physical Chemistry B, 105 (2001) 6474-6487) The protein was submerged in TIP4P water in a rhombic dodecahedral box with an additional 10 Å extension along each axis of the protein. Ions (150 mM NaCl) were added to the solution to make the system electrically neutral. Structures were energy-minimized with the steepest descent algorithm until the convergence criterion of a maximum force smaller than 10.0 kJ/mol/nm was met. Following minimization, each replica (see below for description of the replicas) was equilibrated for 100 ps under NVT conditions.

At this stage the solvent and the solute were independently coupled to a bath of the respective replica's temperature with relaxation time of 0.1 ps by means of the V-rescale algorithm (H. J. C. Berendsen, et al., The Journal of Chemical Physics, 81 (1984) 3684-3690). Next, each replica was equilibrated for an additional 100 ps under NPT conditions using the Brendsen pressure coupling with a coupling time of 1.0 ps and a compressibility constant of $4.5 \times 10^{-5}$ bar$^{-1}$. Finally, REMD production phase simulations were carried out under NPT conditions with the leap-frog algorithm (R. W. Hockney, et al., Journal of Computational Physics, 14 (1974) 148-158) using a 2 fs timestep. Long-range electrostatic interactions were computed using Particle Mesh Ewald (PME) electrostatics (T. Darden, et al., The Journal of Chemical Physics, 103 (1995) 8577-8593). Cutoffs for van der Waals and Coulomb interactions were set to 10 Å. Periodic boundary conditions were applied. The LINCS algorithm was used to constrain bond lengths.

As per GROMACS defaults, exchanges between the different replicas were attempted every 10 ps. Given an average acceptance rate of ~24% (Table 4) successful exchanges were made every 40 ps. This timespan is about four times larger than the autocorelation time of the potential energy which was found to be ~10 ps. These numbers are in general agreement with those recommended by Abraham and Gready (M. J. Abraham, et al., Journal of Chemical Theory and Computation, 4 (2008) 1119-1128).

Figure 7:
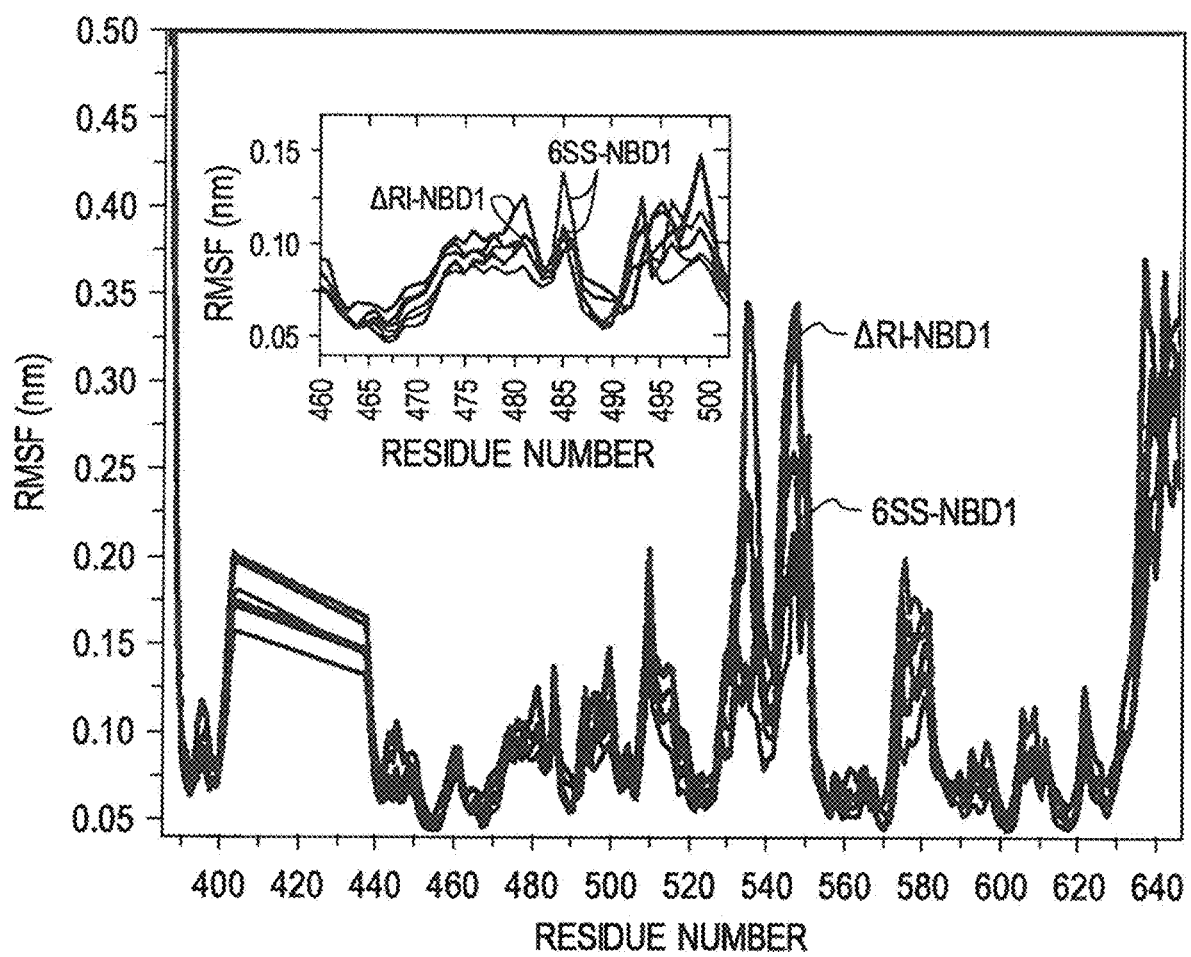
FIG. 7: REMD simulations reveal reduced fluctuations in 6SS-NBD1. Root mean square fluctuation profiles for ΔRI-NBD1 (black, three repeats) and 6SS-NBD1 (gray, three repeats). Residues 405 to 436 are absent in these constructs. Insert: expansion of residues 460 to 505. The close similarity between the RMSF profiles emerging from different simulations is indicative of simulation convergence.

FIG. 15 presents the ground state replicas contribution and round trip for a presentative REMD simulation of 6SS-NBD1. These data suggest that replicas spanning the entire temperature range contributed to the analyzed trajectory (lowest temperature trajectory) and that the replica initiated from the lowest temperature visited the entire temperature range and made at least one round trip, suggesting that these simulations are sufficiently converged. FIG. 16 presents the RMSD profiles calculated for the 6SS simulations whereas FIG. 7 presents the resulting RMSF profiles. The close proximity between the plots obtained from different simulations provide another indication for simulation convergence.

Protein stability, or the lack thereof, represents a substantial challenge to biochemical and biophysical analyses of many proteins, especially membrane proteins that require solubilization in detergents that may destabilize extra—as well as intramembranous domains (Z. Yang, C. Wang, Q. Zhou, J. An, E. Hildebrandt, L. A. Aleksandrov, J. C. Kappes, L. J. DeLucas, J. R. Riordan, I. L. Urbatsch, J. F. Hunt, C. G. Brouillette, Protein Sci, 23 (2014) 769-789; D. V. Tulumello, C. M. Deber, Biochim Biophys Acta, 1818 (2012) 1351-1358). The multidomain complexity and highly dynamic nature of the channel, together with CFTR's intrinsic instability, particularly in detergents, make its study especially challenging (X. Meng, et al., Protein expression and purification, 116 (2015) 159-166; Z. Yang, et al., Protein Sci, 23 (2014) 769-789; E. Hildebrandt, et al., Biochim Biophys Acta, 1838 (2014) 2825-2837).

TABLE 4

Acceptance exchange rates between neighboring replicas for 6SS-NBD1.

| Replica | 0-1 | 1-2 | 2-3 | 3-4 | 4-5 | 5-6 | 6-7 | 7-8 | 8-9 | 9-10 |
|---|---|---|---|---|---|---|---|---|---|---|
| Exchange rate | 0.23 | 0.22 | 0.26 | 0.23 | 0.23 | 0.23 | 0.25 | 0.25 | 0.24 | 0.2 |
| Replica | 10-12 | 11-12 | 12-13 | 13-14 | 14-15 | 15-16 | 16-17 | 17-18 | 18-19 | 19-20 |
| Exchange rate | 0.25 | 0.23 | 0.23 | 0.24 | 0.24 | 0.24 | 0.25 | 0.23 | 0.24 | 0.24 |
| Replica | 20-21 | 21-22 | 22-23 | 23-24 | 24-25 | 25-26 | 26-27 | 27-28 | 29-30 | 30-31 |
| Exchange rate | 0.23 | 0.24 | 0.25 | 0.25 | 0.25 | 0.24 | 0.25 | 0.26 | 0.26 | 0.25 |

Recent work applying similar approaches to unfolding of CFTR domains (C. Wang, et al., Protein Sci, 19 (2010) 1932-1947; I. Protasevich, et al., Protein Sci, 19 (2010) 1917-1931; L. He, et al., J Mol Biol, 427 (2015) 106-120; Z. Yang, et al., Methods Enzymol, 567 (2016) 319-358; R. M. Vernon, et al., J Biol Chem, (2017)) significantly advanced our mechanistic understanding of the disease-causing defect of ΔF508. In the current study, we used DSC to

TABLE 3

CFTR content in membrane preparations

| | | expression system | | CFTR in membrane (μg/billion cells) [2] | | |
|---|---|---|---|---|---|---|
| Mutations | short name | Cell line [1] | response element | transactivator, parent cell line | mean | sd | n |
| WT (CHO) | | D421 | TRE.2 | rtTA, D389 [3] | 166 | | 1 |
| WT (CHO) | | D507.c | TRE.2 | rtTA, D389 | | | |
| WT (CHO) | | D1044 | TRE.2 | 3G, D896 | 30 | | 1 |
| NBD1 mutations | | | | | | | |
| ΔRI (CHO) [4] | | D992 | TRE.2 | 3G, D896 | | | |
| ΔRI/S492P/A534P/I539T (CHO) | 2PT | D727 | TRE.t | rtTA, D389 | 279 | 171 | 5 |
| ΔRI/S492P/A534P/I539T (CHO) | 2PT | D727.1 | TRE.t | 3G, D896 | | | |
| ΔRI/S492P/A534P/I539T (CHO) | 2PT | D994 | TRE.2 | 3G, D896 | | | |

TABLE 3-continued

CFTR content in membrane preparations

| Mutations | short name | Cell line [1] | response element | transactivator, parent cell line | CFTR in membrane (μg/billion cells) [2] | | |
|---|---|---|---|---|---|---|---|
| | | | | | mean | sd | n |
| ΔRI'/2PT/M470V (CHO) | | D851 | TRE.t | rtTA, D389 | 175 | 112 | 5 |
| ΔRI'/2PT/M470V (CHO) | | D1022 | TRE.t | 3G, D896 | 655 | 166 | 3 |
| ΔRI'/2PT/M470V/S495P (CHO) | 5SS | D1012 | TRE.2 | 3G, D896 | 1254 | | 1 |
| ΔRI'/2PT/M470V/S495P/R555K | 6SS | D1013 | TRE.2 | 3G, D896 | 870 | 259 | 6 |
| ΔRI'/2PT/F494N/S495P/G550E/R555K | 7SS | D744 | TRE.t | rtTA, D389 | 287 | 197 | 4 |
| NBD2 mutations | | | | | | | |
| ΔRI'/2PT/H1402S | | D869 | TRE.t | rtTA, D389 | 385 | 314 | 8 |
| ΔRI'/2PT/H1402S | | D917.c | TRE.t | rtTA, D389 | 277 | | 1 |
| ΔRI'/2PT/M470V/H1402S | | D872 | TRE.t | rtTA, D389 | 460 | 193 | 4 |
| ΔRI'/2PT/M470V/H1402S | | D928.c | TRE.t | rtTA, D389 | 406 | 103 | 3 |
| ΔRI'/2PT/M470V/H1402A | | D873 | TRE.t | rtTA, D389 | 375 | | 1 |
| ΔRI'/2PT/M470V/H1402A | | D930.c | TRE.t | rtTA, D389 | 356 | 138 | 4 |
| ΔRI'/2PT/M470V/S495P/R555K/H1402S | 6SS/H1402S | D1028.c | TRE.2 | 3G, D896 | 1130 | 315 | 7 |
| ΔRI'/2PT/S1255L/K1334G/S1359A/Q1411D | 2PT/quad | D742 | TRE.t | rtTA, D389 | 525 | | 1 |

[1] Cell line designation is given to facilitate future sample distribution. CFTR mutations were expressed in CHO cells as detailed in methods. Clonal cell lines have the ".c" suffix.
[2] CFTR-GFP content (total complex glycosylated band C and core glycosylated band B) in microsomal membranes, prepared from three to five billion cells, was quantitated using in-gel GFP fluorescence and P-glycoprotein-EGFP as described previously.
[3] The response element and transactivator expression strategies are described in FIG. 10. CFTR content in membranes was affected by the expression platform strategy, with the highest yields obtained from 5SS-, 6SS- and 6SS/H1402S-CFTR expressing cells (bold numbers).
[4] ΔRI-NBD1 has the Δ405-436 deletion previously used in NBD1 studies. ΔRI' with Δ404-435, differing by one amino acid, was studied previously.

analyze in detail the ability of site-specific substitutions to increase thermal stability ($T_m^{cal}$) of ΔRI-NBD1. We systematically and iteratively combined mutations to demonstrate progressive stabilization of ΔRI/2PT by introducing M470V, S495P and R555K mutations, to ultimately yield an NBD1 domain with highly improved stability.

Indeed, the most stable combinations 6SS-NBD1 and 7SS-NBD1 exhibited $T_m^{cal}$ values of 74° C. and 71° C., respectively, representing an increase of more than 15° C. over ΔRI-NBD1, and outperforming previously published ΔRI/2PT/Teem NBD1 (L. He, et al., J Mol Biol, 427 (2015) 106-120; A. A. Aleksandrov, et al., J Mol Biol, 419 (2012) 41-60) by 7 to 10° C. (FIG. 2).

For the set of single site stabilizing mutations considered in this work, we did not observe a strong correlation between the experimental $T_m^{cal}$ values and either local structural parameters (B-factors, or solvent accessible surface areas) or Fold X-calculated G values. On the other hand, REMD simulations suggested reduced fluctuations at specific positions in the more flexible regions of stabilized 6SS-NBD1, providing a strategy to engineer further mutations in CFTR to generate a protein with even greater stability and potentially paving the way towards NBD1 (and consequently CFTR) stabilization via drug like molecules. Of note, MD simulations have recently been used to probe the unfolding of four NBD1 constructs pointing to several residues (e.g., S492, Q493, T465, A554-Y563, L571, S573, P574, F575, K584, 1586) whose mutation was suggested to enhance the folding efficiency of F508-NBD1 (S. G. Estacio, et al., Mol Biosyst, 12 (2016) 2834-2848). Of these, the S492P and R555K as well as the close-by F494N and S495P mutations were shown in the present work to stabilize the WT domain.

Several earlier studies have suggested that NBD1 structural stability is one of the determining factors in CFTR stability (G. L. Lukacs, et al., Trends Mol Med, 18 (2012) 81-91; S. J. Kim, et al., Frontiers in pharmacology, 3 (2012) 20; C. Wang, et al., Protein Sci, 19 (2010) 1932-1947; I. Protasevich, et al., Protein Sci, 19 (2010) 1917-1931; P. H. Thibodeau, et al., J Biol Chem, 285 (2010) 35825-35835; J. L. Mendoza, et al., Cell, 148 (2012) 164-174. 29; W. M. Rabeh, et al., Cell, 148 (2012) 150-163; L. He, et al., J Mol Biol, 427 (2015) 106-120; Z. Yang, et al., Protein Sci, 23 (2014) 769-789). In particular, the work by Mendoza et al. and Rabeh et al. recognized the correlation of NBD1 in vitro stabilization with the improved de novo folding efficiency and expression of the full length CFTR (J. L. Mendoza, et al., Cell, 148 (2012) 164-174; W. M. Rabeh, et al., Cell, 148 (2012) 150-163). Results with the current, more extensive panel of CFTR mutants fully support this idea. Increased thermal stability of the NBD1 domain ($T_m^{cal}$) correlated directly with improved thermal ($T_m^{trp}$) and functional ($T_m^{func}$) stability of full length CFTR (FIG. 5). The combinations of mutations that were best for stabilizing NBD1, 6SS and 7SS, increased $T_m^{func}$ from 22° C. for WT CFTR to 36° C. (Table 1). ATP binding and hydrolysis in CFTR, as in all ABC transporters, depends on the two NBDs interacting in a head-to-tail dimer to sandwich two MgATP molecules between the Walker A/B motifs of one NBD and the Signature motif of the other (Z. Zhang, et al., Cell, 170 (2017) 483-491.e488; T. Furuta, et al., Biochemistry, 55 (2016) 6730-6738; B. Sorum, et al., Cell, 163 (2015) 724-733). CFTR NBD1 has a degenerate Walker B motif and lacks the switch histidine (equivalent to H1402), making this composite site inactive (D. C. Gadsby, et al., Nature, 440 (2006) 477-483; L. Aleksandrov, et al., J Biol Chem, 277 (2002) 15419-15425). Therefore, ATP hydrolysis is contingent on the second composite site and requires key catalytic residues contributed by NBD2. Our data suggest that progressive structural stabilization of NBD2 raises $T_m^{func}$ by concomitantly protecting the hydrolytic NBD2 domain against thermal inactivation, and is consistent with this requirement for interdomain contacts at the composite site where hydrolysis takes place.

In a typical ABC transporter, ATP binding induces NBD dimerization, while ATP hydrolysis is thought to dissociate the dimer (D. N. Sheppard, et al., Physiol Rev, 79 (1999) S23-45; J. R. Riordan, et al., Annu Rev Biochem, 77 (2008) 701-726; D. C. Gadsby, et al., Nature, 440 (2006) 477-483). A current view is that NBD dimerization and dissociation transmit conformational changes via the ICLs to the transmembrane domains to gate the channel (Z. Zhang, et al., Cell, 170 (2017) 483-491.e488; J. Zhang, et al., J Gen Physiol, 149 (20H) 355-372; W. Y. Lin, et al., Mol Pharmacal, 90 (2016), 275-285; H. I. Yeh, et al., J Gen Physiol, 145 (2015) 47-60). Interestingly, we observed large effects on $T_m^{func}$ and $T_m^{trp}$ by mutations in the Q-loop (S492P, S495P) thought to transmit signals to the transmembrane domains (for example 5SS, Table 1) (P. Linsdell, Adv Exp Med Biol, 925 (2017), 13-32). Potentially, structural stabilization of NBD1 may also enhance these connections to the ICLs and so contribute to stabilization of the full-length CFTR protein. Thus, $T_m^{func}$ may not only track the stability of the NBDs but also the ICL connections. Importantly, the thermally stabilized 6SS-CFTR channel was active at 33° C., and remained active for prolonged times at elevated temperatures as high as 45° C. where WT CFTR rapidly lost function.

Conformational state is an additional component of structural stability. $T_m^{trp}$ detected the stabilizing effect of the switch histidine mutation H1402S, which abolished ATP hydrolysis and would be presumed, as in other ABC transporters, to trap non-hydrolyzed ATP in an NBD1-NBD2 dimer conformation (J. Zaitseva, et al., Embo J, 24 (2005), 1901-1910), and to render an open channel conformation (L. A. Aleksandrov, et al., Protein expression and purification, 116 (2015) 159-166). A similar +5° C. shift in $T_m^{trp}$ due to H1402S was consistently observed in RI/2PT/H1402S, RI/2PT/M470V/H1402S, and 6SS/H1402S, suggesting that the shift in conformational population enhanced structural stability of the protein. Indeed, a similar stabilizing effect was observed in P-glycoprotein with equivalent mutations that promoted the occluded NBD dimer conformation with trapped MgATP (G. Tombline et al., J Biol Chem, 279 (2004) 31212-31220; Z. Yang, et al., Biochim Biophys Acta, 1859 (2017) 48-60). A large body of literature reports on conformational stabilization due to specific mutations and combinations of mutations in G-protein coupled receptors (GPCRs). In those cases, conformational stabilization was essential to obtain crystal structures in different states (M. J. Serrano-Vega, et al., Proc Natl Acad Sci USA, 105 (2008) 877-882; Y. Shibata, et al., Biochim Biophys Acta, 1828 (2013) 1293-1301; F. M. Heydenreich, et al., Frontiers in pharmacology, 6 (2015) 82; N. Vaidehi, et al., Trends Pharmacal Sci, 37 (2016) 37-46). Thermal unfolding studies with P-glycoprotein and other membrane proteins have shown that unfolding of a-helical transmembrane domains is unlikely to be detected by Trp fluorescence over the temperature range of the present study (Z. Yang, et al., Methods Enzymol, 567 (2016) 319-358; Z. Yang, et al., Biochim Biophys Acta, 1859 (2017) 48-60; T. Haltia, et al., Biochim Biophys Acta, 1241 (1995) 295-322; A. M. Pawl, et al., Biochim Biophys Acta, 1818 (2012) 889-895). In CFTR, 11 of the 23 intrinsic Trp residues are situated in transmembrane domains. However, several Trps in NBD1 (W496, W401) and it's connecting ICL4 loop (W1063), as well as in NBD2 (W1274, W1282, W1310, W1316) and its connecting ICL2 loop (W278) are buried within the domains or at the domain interface and eligible to report tertiary unfolding of these cytoplasmic domains (C. A. Royer, Chem Rev, 106 (2006) 1769-1784; K. Stankova, et al., Biochem J, 443 (2012) 701-709). Because fluorescence emission is an average of all Trps in different local environments, the detected single transition for CFTR suggests that unfolding of these domains is highly cooperative. We feel the most straight forward interpretation of the Trp fluorescence data for CFTR is that it represents unfolding of cytoplasmic portions of the protein in a way that is responsive to protein conformational state.

In mammalian cells, the new stabilized variants of CFTR all exhibited strong localization of mature glycosylated protein to the cell surface, were purifiable under mild conditions, and demonstrated significantly improved stability. In conclusion, CFTR variants with a highly stabilized NBD1 domain, imparting greatly enhanced structural and functional stability, together with conformational stabilization by the H1402S mutation, will facilitate future biochemical and biophysical studies, and may open the door to higher resolution structures by Cryo-EM or crystallography. The stabilized CFTR variants may enable structural studies of folding mutations like b.F508, for which protein production and purification have been problematic. They might also facilitate other ongoing lines of investigation, such as domain assembly, the mechanisms of gating and channel regulation, and insights into the natural mutations that cause cystic fibrosis.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached invention disclosure for purposes of illustrating the invention, it will be apparent to those skilled in the art that various changes in the methods and apparatus disclosed herein may be made without departing from the scope of the invention, which is defined in the appended claims. All changes which come within the meaning and range of equivalency of the claims are to be embraced within their scope.

That which is claimed:

1. A modified human cystic fibrosis transmembrane conductance regulator (CFTR) polypeptide or functional fragment thereof that functions as a chloride ion channel, wherein the modified CFTR polypeptide or functional fragment thereof differs from the wild-type human CFTR protein (SEQ ID NO: 1) or fragment thereof by the presence of five or more mutations selected from M470V, S492P, S495P, A534P, I539T, and R555K, such that the stability of the modified CFTR polypeptide or functional fragment thereof is increased relative to that of the wild-type human CFTR polypeptide or fragment thereof.

2. The modified CFTR polypeptide or functional fragment thereof of claim 1, wherein the modified CFTR polypeptide or functional fragment thereof differs from the wild-type human CFTR protein (SEQ ID NO: 1) or fragment thereof by the presence of six mutations.

3. The modified CFTR polypeptide or functional fragment thereof of claim 1, wherein the modified CFTR polypeptide or functional fragment thereof further comprises a deletion of amino acid residue F508 (ΔF508).

4. The modified CFTR polypeptide or functional fragment thereof of claim 1, wherein the modified CFTR polypeptide or functional fragment thereof comprises a deletion of amino acid residues 405-436 (ΔRI) or a deletion of amino acid residues 404-435 (ΔRI').

5. The modified CFTR polypeptide or functional fragment thereof of claim 4, wherein the five or more mutations are:
M470V, S492P, S495P, A534P, and I539T; or
M470V, S492P, S495P, A534P, I539T, and R555K.

6. The modified CFTR polypeptide or functional fragment thereof of claim 1, further comprising one or more tags selected from a $His_{10}$-purification tag, a FLAG epitope, a green fluorescent protein (GFP), and a SUMO polypeptide.

7. A composition comprising the modified CFTR polypeptide or functional fragment thereof of claim 1.

8. A composition comprising the modified CFTR polypeptide or functional fragment thereof of claim 3.

9. A composition comprising the modified CFTR polypeptide or functional fragment thereof of claim 4.

10. A nucleic acid molecule encoding the modified CFTR polypeptide or functional fragment thereof of claim 1.

11. A nucleic acid molecule encoding the modified CFTR polypeptide or functional fragment thereof of claim 3.

12. A nucleic acid molecule encoding the modified CFTR polypeptide or functional fragment thereof of claim 4.

13. A vector comprising the nucleic acid molecule of claim 10.

14. An isolated host cell comprising the nucleic acid molecule of claim 10.

15. A method of studying CFTR structure and/or function, comprising determining the stability and/or folding properties of the modified CFTR polypeptide or functional fragment thereof of claim 1.

16. A method of screening a compound, comprising contacting a compound with the modified CFTR polypeptide or functional fragment thereof of claim 1, and identifying the compound that modulates one or more biological and/or physical properties of the modified CFTR polypeptide or functional fragment thereof.

* * * * *

UNITED STATES PATENT AND TRADEMARK OFFICE
CERTIFICATE OF CORRECTION

PATENT NO. : 11,560,413 B2
APPLICATION NO. : 16/277888
DATED : January 24, 2023
INVENTOR(S) : Kappes et al.

It is certified that error appears in the above-identified patent and that said Letters Patent is hereby corrected as shown below:

On the Title Page

(56) References Cited; PUBLICATIONS, Page 2, Column 2, Atwell, et al cite, Line 63: Please correct "23(51:375-384" to read --23(5):375-384--

(56) References Cited; PUBLICATIONS, Page 3, Column 1, Quen cite, Line 12: Please correct "Quen" to read --Quon--

(56) References Cited; PUBLICATIONS, Page 3, Column 1, Haltia et al. cite, Line 20: Please correct "proteins's"" to read --proteins"--

In the Specification

Column 7, Line 59: Please correct "35, 46." to read --35, 45,--

Column 30, Line 17: Please correct "Δ1405-436D" to read --Δ1405-436)--

Column 37, Line 33: Please correct "λ of 334 nm" to read --$\lambda_{max}$ of 334 nm--

Column 39, Line 47: Please correct "S1255LIK1334G/S1359A/Q14110" to read --S1255L/K1334G/S1359A/Q14110--

Column 42, Line 35: Please correct "ΔTP" to read --ATP--

Signed and Sealed this
Thirtieth Day of May, 2023

Katherine Kelly Vidal
*Director of the United States Patent and Trademark Office*

SEQUENCE LISTING

<160> NUMBER OF SEQ ID NOS: 18

<210> SEQ ID NO 1
<211> LENGTH: 1480
<212> TYPE: PRT
<213> ORGANISM: Homo sapiens

<400> SEQUENCE: 1

Met Gln Arg Ser Pro Leu Glu Lys Ala Ser Val Val Ser Lys Leu Phe

-continued

```
1               5                   10                  15
Phe Ser Trp Thr Arg Pro Ile Leu Arg Lys Gly Tyr Arg Gln Arg Leu
            20                  25                  30

Glu Leu Ser Asp Ile Tyr Gln Ile Pro Ser Val Asp Ser Ala Asp Asn
            35                  40                  45

Leu Ser Glu Lys Leu Glu Arg Glu Trp Asp Arg Glu Leu Ala Ser Lys
50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
            115                 120                 125

Leu Leu Phe Ile Val Arg Thr Leu Leu Leu His Pro Ala Ile Phe Gly
            130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
            195                 200                 205

Ala Leu Leu Met Gly Leu Ile Trp Glu Leu Leu Gln Ala Ser Ala Phe
210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
            275                 280                 285

Arg Gln Thr Glu Leu Lys Leu Thr Arg Lys Ala Ala Tyr Val Arg Tyr
            290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
            355                 360                 365

Asn Lys Ile Gln Asp Phe Leu Gln Lys Gln Glu Tyr Lys Thr Leu Glu
370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430
```

-continued

```
Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Val Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
                500                 505                 510

Asp Glu Tyr Arg Tyr Arg Ser Val Ile Lys Ala Cys Gln Leu Glu Glu
            515                 520                 525

Asp Ile Ser Lys Phe Ala Glu Lys Asp Asn Ile Val Leu Gly Glu Gly
        530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
        595                 600                 605

His Leu Lys Lys Ala Asp Lys Ile Leu Ile Leu His Glu Gly Ser Ser
    610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
            660                 665                 670

Gly Asp Ala Pro Val Ser Trp Thr Glu Thr Lys Lys Gln Ser Phe Lys
        675                 680                 685

Gln Thr Gly Glu Phe Gly Glu Lys Arg Lys Asn Ser Ile Leu Asn Pro
    690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Ser Leu Val Pro Asp Ser Glu Gln Gly Glu Ala Ile Leu Pro Arg Ile
            740                 745                 750

Ser Val Ile Ser Thr Gly Pro Thr Leu Gln Ala Arg Arg Arg Gln Ser
        755                 760                 765

Val Leu Asn Leu Met Thr His Ser Val Asn Gln Gly Gln Asn Ile His
    770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
                805                 810                 815

Gly Leu Glu Ile Ser Glu Glu Ile Asn Glu Glu Asp Leu Lys Glu Cys
            820                 825                 830

Phe Phe Asp Asp Met Glu Ser Ile Pro Ala Val Thr Thr Trp Asn Thr
        835                 840                 845
```

-continued

Tyr Leu Arg Tyr Ile Thr Val His Lys Ser Leu Ile Phe Val Leu Ile
            850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
            900                 905                 910

Tyr Tyr Val Phe Tyr Ile Tyr Gly Val Ala Asp Thr Leu Leu Ala
                915                 920                 925

Met Gly Phe Phe Arg Gly Leu Pro Leu Val His Thr Leu Ile Thr Val
930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
                965                 970                 975

Ser Lys Asp Ile Ala Ile Leu Asp Asp Leu Leu Pro Leu Thr Ile Phe
            980                 985                 990

Asp Phe Ile Gln Leu Leu Leu Ile Val Ile Gly Ala Ile Ala Val Val
                995                 1000                1005

Ala Val Leu Gln Pro Tyr Ile Phe Val Ala Thr Val Pro Val Ile
    1010                1015                1020

Val Ala Phe Ile Met Leu Arg Ala Tyr Phe Leu Gln Thr Ser Gln
    1025                1030                1035

Gln Leu Lys Gln Leu Glu Ser Glu Gly Arg Ser Pro Ile Phe Thr
    1040                1045                1050

His Leu Val Thr Ser Leu Lys Gly Leu Trp Thr Leu Arg Ala Phe
    1055                1060                1065

Gly Arg Gln Pro Tyr Phe Glu Thr Leu Phe His Lys Ala Leu Asn
    1070                1075                1080

Leu His Thr Ala Asn Trp Phe Leu Tyr Leu Ser Thr Leu Arg Trp
    1085                1090                1095

Phe Gln Met Arg Ile Glu Met Ile Phe Val Ile Phe Phe Ile Ala
    1100                1105                1110

Val Thr Phe Ile Ser Ile Leu Thr Thr Gly Glu Gly Glu Gly Arg
    1115                1120                1125

Val Gly Ile Ile Leu Thr Leu Ala Met Asn Ile Met Ser Thr Leu
    1130                1135                1140

Gln Trp Ala Val Asn Ser Ser Ile Asp Val Asp Ser Leu Met Arg
    1145                1150                1155

Ser Val Ser Arg Val Phe Lys Phe Ile Asp Met Pro Thr Glu Gly
    1160                1165                1170

Lys Pro Thr Lys Ser Thr Lys Pro Tyr Lys Asn Gly Gln Leu Ser
    1175                1180                1185

Lys Val Met Ile Ile Glu Asn Ser His Val Lys Lys Asp Asp Ile
    1190                1195                1200

Trp Pro Ser Gly Gly Gln Met Thr Val Lys Asp Leu Thr Ala Lys
    1205                1210                1215

Tyr Thr Glu Gly Gly Asn Ala Ile Leu Glu Asn Ile Ser Phe Ser
    1220                1225                1230

Ile Ser Pro Gly Gln Arg Val Gly Leu Leu Gly Arg Thr Gly Ser
    1235                1240                1245

Gly Lys Ser Thr Leu Leu Ser Ala Phe Leu Arg Leu Leu Asn Thr

```
            1250                1255                1260
Glu Gly Glu Ile Gln Ile Asp Gly Val Ser Trp Asp Ser Ile Thr
            1265                1270                1275
Leu Gln Gln Trp Arg Lys Ala Phe Gly Val Ile Pro Gln Lys Val
            1280                1285                1290
Phe Ile Phe Ser Gly Thr Phe Arg Lys Asn Leu Asp Pro Tyr Glu
            1295                1300                1305
Gln Trp Ser Asp Gln Glu Ile Trp Lys Val Ala Asp Glu Val Gly
            1310                1315                1320
Leu Arg Ser Val Ile Glu Gln Phe Pro Gly Lys Leu Asp Phe Val
            1325                1330                1335
Leu Val Asp Gly Gly Cys Val Leu Ser His Gly His Lys Gln Leu
            1340                1345                1350
Met Cys Leu Ala Arg Ser Val Leu Ser Lys Ala Lys Ile Leu Leu
            1355                1360                1365
Leu Asp Glu Pro Ser Ala His Leu Asp Pro Val Thr Tyr Gln Ile
            1370                1375                1380
Ile Arg Arg Thr Leu Lys Gln Ala Phe Ala Asp Cys Thr Val Ile
            1385                1390                1395
Leu Cys Glu His Arg Ile Glu Ala Met Leu Glu Cys Gln Gln Phe
            1400                1405                1410
Leu Val Ile Glu Glu Asn Lys Val Arg Gln Tyr Asp Ser Ile Gln
            1415                1420                1425
Lys Leu Leu Asn Glu Arg Ser Leu Phe Arg Gln Ala Ile Ser Pro
            1430                1435                1440
Ser Asp Arg Val Lys Leu Phe Pro His Arg Asn Ser Ser Lys Cys
            1445                1450                1455
Lys Ser Lys Pro Gln Ile Ala Ala Leu Lys Glu Glu Thr Glu Glu
            1460                1465                1470
Glu Val Gln Asp Thr Arg Leu
            1475                1480

<210> SEQ ID NO 2
<211> LENGTH: 6132
<212> TYPE: DNA
<213> ORGANISM: Homo sapiens

<400> SEQUENCE: 2
aattggaagc aaatgacatc acagcaggtc agagaaaaag ggttgagcgg caggcaccca      60
gagtagtagg tctttggcat taggagcttg agcccagacg gccctagcag ggaccccagc     120
gcccgagaga ccatgcagag gtcgcctctg gaaaaggcca gcgttgtctc caaacttttt     180
ttcagctgga ccagaccaat tttgaggaaa ggatacagac agcgcctgga attgtcagac     240
atataccaaa tcccttctgt tgattctgct gacaatctat ctgaaaaatt ggaaagagaa     300
tgggatagag agctggcttc aaagaaaaat cctaaactca ttaatgccct tcggcgatgt     360
tttttctgga gatttatgtt ctatggaatc ttttatatt taggggaagt caccaaagca     420
gtacagcctc tcttactggg aagaatcata gcttcctatg acccggataa caaggaggaa     480
cgctctatcg cgatttatct aggcataggc ttatgccttc tctttattgt gaggacactg     540
ctcctacacc cagccatttt tggccttcat cacattggaa tgcagatgag aatagctatg     600
tttagtttga tttataagaa gactttaaag ctgtcaagcc gtgttctaga taaaataagt     660
attggacaac ttgttagtct cctttccaac aacctgaaca aatttgatga aggacttgca     720
```

-continued

```
ttggcacatt tcgtgtggat cgctcctttg caagtggcac tcctcatggg gctaatctgg      780
gagttgttac aggcgtctgc cttctgtgga cttggtttcc tgatagtcct tgcccttttt      840
caggctgggc tagggagaat gatgatgaag tacagagatc agagagctgg gaagatcagt      900
gaaagacttg tgattacctc agaaatgatt gaaaatatcc aatctgttaa ggcatactgc      960
tgggaagaag caatggaaaa atgattgaa acttaagac aaacagaact gaaactgact       1020
cggaaggcag cctatgtgag atacttcaat agctcagcct tcttcttctc agggttcttt     1080
gtggtgtttt tatctgtgct tccctatgca ctaatcaaag gaatcatcct ccggaaaata     1140
ttcaccacca tctcattctg cattgttctg cgcatggcgg tcactcggca atttccctgg     1200
gctgtacaaa catggtatga ctctcttgga gcaataaaca aaatacagga tttcttacaa     1260
aagcaagaat ataagacatt ggaatataac ttaacgacta cagaagtagt gatggagaat     1320
gtaacagcct tctgggagga gggatttggg gaattatttg agaaagcaaa acaaaacaat     1380
aacaatagaa aaacttctaa tggtgatgac agcctcttct tcagtaattt ctcacttctt     1440
ggtactcctg tcctgaaaga tattaatttc aagatagaaa gaggacagtt gttggcggtt     1500
gctggatcca ctggagcagg caagacttca cttctaatgg tgattatggg agaactggag     1560
ccttcagagg gtaaaattaa gcacagtgga agaatttcat tctgttctca gttttcctgg     1620
attatgcctg gcaccattaa agaaaatatc atctttggtg tttcctatga tgaatataga     1680
tacagaagcg tcatcaaagc atgccaacta gaagaggaca tctccaagtt tgcagagaaa     1740
gacaatatag ttcttggaga aggtggaatc acactgagtg gaggtcaacg agcaagaatt     1800
tctttagcaa gagcagtata caaagatgct gatttgtatt tattagactc tccttttgga     1860
tacctagatg ttttaacaga aaaagaaata tttgaaagct gtgtctgtaa actgatggct     1920
aacaaaacta ggattttggt cacttctaaa atggaacatt taaagaaagc tgacaaaata     1980
ttaattttgc atgaaggtag cagctatttt tatgggacat tttcagaact ccaaaatcta     2040
cagccagact ttagctcaaa actcatggga tgtgattctt tcgaccaatt tagtgcagaa     2100
agaagaaatt caatcctaac tgagacctta caccgtttct cattagaagg agatgctcct     2160
gtctcctgga cagaaacaaa aaaacaatct tttaaacaga ctggagagtt tggggaaaaa     2220
aggaagaatt ctattctcaa tccaatcaac tctatacgaa aattttccat tgtgcaaaag     2280
actcccttac aaatgaatgg catcgaagag gattctgatg agcctttaga gagaaggctg     2340
tccttagtac cagattctga gcagggagag gcgatactgc ctcgcatcag cgtgatcagc     2400
actggcccca cgcttcaggc acgaaggagg cagtctgtcc tgaacctgat gacacactca     2460
gttaaccaag gtcagaacat tcaccgaaag acaacagcat ccacacgaaa agtgtcactg     2520
gcccctcagg caaacttgac tgaactggat atatattcaa gaaggttatc tcaagaaact     2580
ggcttggaaa taagtgaaga aattaacgaa gaagacttaa aggagtgctt ttttgatgat     2640
atggagagca taccagcagt gactacatgg aacacatacc ttcgatatat tactgtccac     2700
aagagcttaa ttttgtgct aatttggtgc ttagtaattt ttctggcaga ggtggctgct     2760
tctttggttg tgctgtggct ccttggaaac actcctcttc aagacaaagg gaatagtact     2820
catagtagaa ataacagcta tgcagtgatt atcaccagca ccagttcgta ttatgtgttt     2880
tacatttacg tgggagtagc cgacactttg cttgctatgg gattcttcag aggtctacca     2940
ctggtgcata ctctaatcac agtgtcgaaa attttacacc acaaaatgtt acattctgtt     3000
cttcaagcac ctatgtcaac cctcaacacg ttgaaagcag gtgggattct taatagattc     3060
tccaaagata tagcaatttt ggatgacctt ctgcctctta ccatatttga cttcatccag     3120
```

```
ttgttattaa ttgtgattgg agctatagca gttgtcgcag ttttacaacc ctacatcttt    3180
gttgcaacag tgccagtgat agtggctttt attatgttga gagcatattt cctccaaacc    3240
tcacagcaac tcaaacaact ggaatctgaa ggcaggagtc caattttcac tcatcttgtt    3300
acaagcttaa aaggactatg gacacttcgt gccttcggac ggcagcctta ctttgaaact    3360
ctgttccaca aagctctgaa tttacatact gccaactggt tcttgtacct gtcaacactg    3420
cgctggttcc aaatgagaat agaaatgatt tttgtcatct tcttcattgc tgttaccttc    3480
atttccattt taacaacagg agaaggagaa ggaagagttg gtattatcct gactttagcc    3540
atgaatatca tgagtacatt gcagtgggct gtaaactcca gcatagatgt ggatagcttg    3600
atgcgatctg tgagccgagt cttttaagttc attgacatgc caacagaagg taaacctacc    3660
aagtcaacca aaccatacaa gaatggccaa ctctcgaaag ttatgattat tgagaattca    3720
cacgtgaaga aagatgacat ctggccctca gggggccaaa tgactgtcaa agatctcaca    3780
gcaaaataca cagaaggtgg aaatgccata ttagagaaca tttccttctc aataagtcct    3840
ggccagaggg tgggcctctt gggaagaact ggatcaggga gagtactttt gttatcagct    3900
tttttgagac tactgaacac tgaaggagaaa atccagatcg atggtgtgtc ttgggattca    3960
ataactttgc aacagtggag gaaagccttt ggagtgatac cacagaaagt atttattttt    4020
tctggaacat ttagaaaaaa cttggatccc tatgaacagt ggagtgatca agaaatatgg    4080
aaagttgcag atgaggttgg gctcagatct gtgatagaac agtttcctgg gaagcttgac    4140
tttgtccttg tggatgggggg ctgtgtccta agccatggcc acaagcagtt gatgtgcttg    4200
gctagatctg ttctcagtaa ggcgaagatc ttgctgcttg atgaacccag tgctcatttg    4260
gatccagtaa cataccaaat aattagaaga actctaaaac aagcatttgc tgattgcaca    4320
gtaattctct gtgaacacag gatagaagca atgctggaat gccaacaatt tttggtcata    4380
gaagagaaca aagtgcggca gtacgattcc atccagaaac tgctgaacga gaggagcctc    4440
ttccggcaag ccatcagccc ctccgacagg gtgaagctct ttccccaccg gaactcaagc    4500
aagtgcaagt ctaagcccca gattgctgct ctgaaagagg agacagaaga agaggtgcaa    4560
gatacaaggc tttagagagc agcataaatg ttgacatggg acatttgctc atggaattgg    4620
agctcgtggg acagtcacct catggaattg gagctcgtgg aacagttacc tctgcctcag    4680
aaaacaagga tgaattaagt tttttttttaa aaaagaaaca tttggtaagg ggaattgagg    4740
acactgatat gggtcttgat aaatggcttc ctggcaatag tcaaattgtg tgaaaggtac    4800
ttcaaatcct tgaagattta ccacttgtgt tttgcaagcc agattttcct gaaaacccttt    4860 gccatgtgct agtaattgga aaggcagctc taaatgtcaa tcagcctagt tgatcagctt    4920
attgtctagt gaaactcgtt aatttgtagt gttggagaag aactgaaatc atacttctta    4980
gggttatgat taagtaatga taactggaaa cttcagcggt ttatataagc ttgtattcct    5040
ttttctctcc tctccccatg atgtttagaa acacaactat attgtttgct aagcattcca    5100
actatctcat ttccaagcaa gtattagaat accacaggaa ccacaagact gcacatcaaa    5160
atatgcccca ttcaacatct agtgagcagt caggaaagag aacttccaga tcctggaaat    5220
cagggttagt attgtccagg tctaccaaaa atctcaatat ttcagataat cacaatacat    5280
cccttacctg ggaaagggct gttataatct ttcacagggg acaggatggt tcccttgatg    5340
aagaagttga tatgcctttt cccaactcca gaaagtgaca agctcacaga cctttgaact    5400
agagtttagc tggaaaagta tgttagtgca aattgtcaca ggacagccct tctttccaca    5460
```

|  |  |
|---|---|
| gaagctccag gtagagggtg tgtaagtaga taggccatgg gcactgtggg tagacacaca | 5520 |
| tgaagtccaa gcatttagat gtataggttg atggtggtat gttttcaggc tagatgtatg | 5580 |
| tacttcatgc tgtctacact aagagagaat gagagacaca ctgaagaagc accaatcatg | 5640 |
| aattagtttt atatgcttct gttttataat tttgtgaagc aaaatttttt ctctaggaaa | 5700 |
| tatttatttt aataatgttt caaacatata taacaatgct gtattttaaa agaatgatta | 5760 |
| tgaattacat ttgtataaaa taattttat atttgaaata ttgactttt atggcactag | 5820 |
| tatttctatg aaatattatg ttaaaactgg gacaggggag aacctagggt gatattaacc | 5880 |
| aggggccatg aatcaccttt tggtctggag ggaagccttg gggctgatgc agttgttgcc | 5940 |
| cacagctgta tgattcccag ccagcacagc ctcttagatg cagttctgaa gaagatggta | 6000 |
| ccaccagtct gactgtttcc atcaagggta cactgccttc tcaactccaa actgactctt | 6060 |
| aagaagactg cattatattt attactgtaa gaaaatatca cttgtcaata aaatccatac | 6120 |
| atttgtgtga aa | 6132 |

```
<210> SEQ ID NO 3
<211> LENGTH: 5
<212> TYPE: PRT
<213> ORGANISM: Homo sapiens

<400> SEQUENCE: 3

Leu Ser Gly Gly Gln
1               5

<210> SEQ ID NO 4
<211> LENGTH: 100
<212> TYPE: PRT
<213> ORGANISM: Homo sapiens

<400> SEQUENCE: 4

Gly Ser Thr Gly Ala Gly Lys Thr Ser Leu Leu Met Met Ile Met Gly
1               5                   10                  15

Glu Leu Glu Pro Ser Glu Gly Lys Ile Lys His Ser Gly Arg Ile Ser
                20                  25                  30

Phe Cys Ser Gln Phe Ser Trp Ile Met Pro Gly Thr Ile Lys Glu Asn
            35                  40                  45

Ile Ile Phe Gly Val Ser Tyr Asp Glu Tyr Arg Tyr Arg Ser Val Ile
        50                  55                  60

Lys Ala Cys Gln Leu Glu Glu Asp Ile Ser Lys Phe Ala Glu Lys Asp
65                  70                  75                  80

Asn Ile Val Leu Gly Glu Gly Gly Ile Thr Leu Ser Gly Gly Gln Arg
                85                  90                  95

Ala Arg Ile Ser
            100

<210> SEQ ID NO 5
<211> LENGTH: 100
<212> TYPE: PRT
<213> ORGANISM: Homo sapiens

<400> SEQUENCE: 5

Gly Pro Val Gly Ala Gly Lys Ser Ser Leu Leu Ser Ala Val Leu Gly
1               5                   10                  15

Glu Leu Ala Pro Ser His Gly Leu Val Ser Val His Gly Arg Ile Ala
                20                  25                  30

Tyr Val Ser Gln Gln Pro Trp Val Phe Ser Gly Thr Leu Arg Ser Asn
```

```
                35                  40                  45
Ile Leu Phe Gly Lys Lys Tyr Glu Lys Glu Arg Tyr Glu Lys Val Ile
             50                  55                  60
Lys Ala Cys Ala Leu Lys Lys Asp Leu Gln Leu Leu Glu Asp Gly Asp
 65                  70                  75                  80
Leu Thr Val Ile Gly Asp Arg Gly Thr Thr Leu Ser Gly Gly Gln Lys
                 85                  90                  95
Ala Arg Val Asn
            100

<210> SEQ ID NO 6
<211> LENGTH: 100
<212> TYPE: PRT
<213> ORGANISM: Homo sapiens

<400> SEQUENCE: 6

Gly Gln Val Gly Cys Gly Lys Ser Ser Leu Leu Ser Ala Leu Leu Ala
 1               5                  10                  15
Glu Met Asp Lys Val Glu Gly His Val Ala Ile Lys Gly Ser Val Ala
             20                  25                  30
Tyr Val Pro Gln Gln Ala Trp Ile Gln Asn Asp Ser Leu Arg Glu Asn
                35                  40                  45
Ile Leu Phe Gly Cys Gln Leu Glu Glu Pro Tyr Tyr Arg Ser Val Ile
             50                  55                  60
Gln Ala Cys Ala Leu Leu Pro Asp Leu Glu Ile Leu Pro Ser Gly Asp
 65                  70                  75                  80
Arg Thr Glu Ile Gly Glu Lys Gly Val Asn Leu Ser Gly Gly Gln Lys
                 85                  90                  95
Gln Arg Val Ser
            100

<210> SEQ ID NO 7
<211> LENGTH: 100
<212> TYPE: PRT
<213> ORGANISM: Homo sapiens

<400> SEQUENCE: 7

Gly Pro Val Gly Cys Gly Lys Ser Ser Leu Val Ser Ala Leu Leu Gly
 1               5                  10                  15
Glu Met Glu Lys Leu Glu Gly Lys Val His Met Lys Gly Ser Val Ala
             20                  25                  30
Tyr Val Pro Gln Gln Ala Trp Ile Gln Asn Cys Thr Leu Gln Glu Asn
                35                  40                  45
Val Leu Phe Gly Lys Ala Leu Asn Pro Lys Arg Tyr Gln Gln Thr Leu
             50                  55                  60
Glu Ala Cys Ala Leu Leu Ala Asp Leu Glu Met Leu Pro Gly Gly Asp
 65                  70                  75                  80
Gln Thr Glu Ile Gly Glu Lys Gly Ile Asn Leu Ser Gly Gly Gln Arg
                 85                  90                  95
Gln Arg Val Ser
            100

<210> SEQ ID NO 8
<211> LENGTH: 100
<212> TYPE: PRT
<213> ORGANISM: Homo sapiens

<400> SEQUENCE: 8
```

```
Gly Pro Val Gly Ser Gly Lys Ser Ser Leu Ile Ser Ala Met Leu Gly
1               5                   10                  15

Glu Met Glu Asn Val His Gly His Ile Thr Ile Lys Gly Thr Thr Ala
            20                  25                  30

Tyr Val Pro Gln Gln Ser Trp Ile Gln Asn Gly Thr Ile Lys Asp Asn
            35                  40                  45

Ile Leu Phe Gly Thr Glu Phe Asn Glu Lys Arg Tyr Gln Gln Val Leu
        50                  55                  60

Glu Ala Cys Ala Leu Leu Pro Asp Leu Glu Met Leu Pro Gly Gly Asp
65                  70                  75                  80

Leu Ala Glu Ile Gly Glu Lys Gly Ile Asn Leu Ser Gly Gly Gln Lys
                85                  90                  95

Gln Arg Ile Ser
            100

<210> SEQ ID NO 9
<211> LENGTH: 100
<212> TYPE: PRT
<213> ORGANISM: Homo sapiens

<400> SEQUENCE: 9

Gly Pro Val Gly Ala Gly Lys Ser Ser Leu Leu Ser Ala Leu Leu Gly
1               5                   10                  15

Glu Leu Ser Lys Val Glu Gly Phe Val Ser Ile Glu Gly Ala Val Ala
            20                  25                  30

Tyr Val Pro Gln Glu Ala Trp Val Gln Asn Thr Ser Val Val Glu Asn
            35                  40                  45

Val Cys Phe Gly Gln Glu Leu Asp Pro Pro Trp Leu Glu Arg Val Leu
        50                  55                  60

Glu Ala Cys Ala Leu Gln Pro Asp Val Asp Ser Phe Pro Glu Gly Ile
65                  70                  75                  80

His Thr Ser Ile Gly Glu Gln Gly Met Asn Leu Ser Gly Gly Gln Lys
                85                  90                  95

Gln Arg Leu Ser
            100

<210> SEQ ID NO 10
<211> LENGTH: 100
<212> TYPE: PRT
<213> ORGANISM: Homo sapiens

<400> SEQUENCE: 10

Gly Gln Val Gly Cys Gly Lys Ser Ser Leu Leu Ala Ala Leu Leu Gly
1               5                   10                  15

Glu Met Gln Lys Val Ser Gly Ala Val Phe Trp Ser Ser Leu Pro Asp
            20                  25                  30

Tyr Ala Ser Gln Lys Pro Trp Leu Leu Asn Ala Thr Val Glu Glu Asn
            35                  40                  45

Ile Ile Phe Glu Ser Pro Phe Asn Lys Gln Arg Tyr Lys Met Val Ile
        50                  55                  60

Glu Ala Cys Ser Leu Gln Pro Asp Ile Asp Ile Leu Pro His Gly Asp
65                  70                  75                  80

Gln Thr Gln Ile Gly Glu Arg Gly Ile Asn Leu Ser Gly Gly Gln Arg
                85                  90                  95

Gln Arg Ile Ser
            100
```

<210> SEQ ID NO 11
<211> LENGTH: 100
<212> TYPE: PRT
<213> ORGANISM: Homo sapiens

<400> SEQUENCE: 11

Gly Gln Val Gly Cys Gly Lys Ser Ser Leu Leu Ala Ile Leu Gly
1               5                   10                  15

Glu Met Gln Thr Leu Glu Gly Lys Val His Trp Ser Asn Val Asn Glu
            20                  25                  30

Tyr Ala Ala Gln Lys Pro Trp Leu Leu Asn Ala Thr Val Glu Glu Asn
        35                  40                  45

Ile Thr Phe Gly Ser Pro Phe Asn Lys Gln Arg Tyr Lys Ala Val Thr
50                  55                  60

Asp Ala Cys Ser Leu Gln Pro Asp Ile Asp Leu Pro Phe Gly Asp
65                  70                  75                  80

Gln Thr Glu Ile Gly Arg Gly Ile Asn Leu Ser Gly Gly Gln Arg
                85                  90                  95

Gln Arg Ile Cys
            100

<210> SEQ ID NO 12
<211> LENGTH: 103
<212> TYPE: PRT
<213> ORGANISM: Homo sapiens

<400> SEQUENCE: 12

Gly Lys Val Gly Cys Gly Lys Ser Ser Leu Leu Ala Ala Ile Ala Gly
1               5                   10                  15

Glu Leu His Arg Leu Arg Gly His Val Ala Val Arg Gly Leu Ser Lys
            20                  25                  30

Gly Phe Gly Leu Ala Thr Gln Glu Pro Trp Ile Gln Phe Ala Thr Ile
        35                  40                  45

Arg Asp Asn Ile Leu Phe Gly Lys Thr Phe Ala Gln Leu Tyr Lys
50                  55                  60

Glu Val Leu Glu Ala Cys Ala Leu Asn Asp Asp Leu Ser Ile Leu Pro
65                  70                  75                  80

Ala Gly Asp Gln Thr Glu Val Gly Glu Lys Gly Val Thr Leu Ser Gly
                85                  90                  95

Gly Gln Arg Ala Arg Ile Ala
            100

<210> SEQ ID NO 13
<211> LENGTH: 100
<212> TYPE: PRT
<213> ORGANISM: Homo sapiens

<400> SEQUENCE: 13

Gly Asn Thr Gly Ser Gly Lys Ser Ser Leu Leu Ser Ala Ile Leu Glu
1               5                   10                  15

Glu Met His Leu Leu Glu Gly Ser Val Gly Val Gln Gly Ser Leu Ala
            20                  25                  30

Tyr Val Pro Gln Gln Ala Trp Ile Val Ser Gly Asn Ile Arg Glu Asn
        35                  40                  45

Ile Leu Met Gly Gly Ala Tyr Asp Lys Ala Arg Tyr Leu Gln Val Leu
50                  55                  60

His Cys Cys Ser Leu Asn Arg Asp Leu Glu Leu Leu Pro Phe Gly Asp
65                  70                  75                  80

Met Thr Glu Ile Gly Glu Arg Gly Leu Asn Leu Ser Gly Gly Gln Lys
                85                  90                  95

Gln Arg Ile Ser
            100

<210> SEQ ID NO 14
<211> LENGTH: 100
<212> TYPE: PRT
<213> ORGANISM: Homo sapiens

<400> SEQUENCE: 14

Gly Asn Val Gly Ser Gly Lys Ser Ser Leu Leu Ala Ala Leu Leu Gly
1               5                   10                  15

Gln Met Gln Leu Gln Lys Gly Val Val Ala Val Asn Gly Thr Leu Ala
                20                  25                  30

Tyr Val Ser Gln Gln Ala Trp Ile Phe His Gly Asn Val Arg Glu Asn
            35                  40                  45

Ile Leu Phe Gly Glu Lys Tyr Asp His Gln Arg Tyr Gln His Thr Val
    50                  55                  60

Arg Val Cys Gly Leu Gln Lys Asp Leu Ser Asn Leu Pro Tyr Gly Asp
65                  70                  75                  80

Leu Thr Glu Ile Gly Glu Arg Gly Leu Asn Leu Ser Gly Gly Gln Arg
                85                  90                  95

Gln Arg Ile Ser
            100

<210> SEQ ID NO 15
<211> LENGTH: 100
<212> TYPE: PRT
<213> ORGANISM: Homo sapiens

<400> SEQUENCE: 15

Gly Ser Val Gly Ser Gly Lys Thr Ser Leu Ile Ser Ala Ile Leu Gly
1               5                   10                  15

Gln Met Thr Leu Leu Glu Gly Ser Ile Ala Ile Ser Gly Thr Phe Ala
                20                  25                  30

Tyr Val Ala Gln Gln Ala Trp Ile Leu Asn Ala Thr Leu Arg Asp Asn
            35                  40                  45

Ile Leu Phe Gly Lys Glu Tyr Asp Glu Glu Arg Tyr Asn Ser Val Leu
    50                  55                  60

Asn Ser Cys Cys Leu Arg Pro Asp Leu Ala Ile Leu Pro Ser Ser Asp
65                  70                  75                  80

Leu Thr Glu Ile Gly Glu Arg Gly Ala Asn Leu Ser Gly Gly Gln Arg
                85                  90                  95

Gln Arg Ile Ser
            100

<210> SEQ ID NO 16
<211> LENGTH: 100
<212> TYPE: PRT
<213> ORGANISM: Gallus gallus

<400> SEQUENCE: 16

Gly Ser Thr Gly Ser Gly Lys Thr Ser Leu Leu Met Leu Ile Met Gly
1               5                   10                  15

Glu Leu Glu Pro Ser Glu Gly Lys Ile Lys His Ser Gly Arg Ile Ser

```
                    20                  25                  30

Phe Ser Pro Gln Val Ser Trp Ile Met Pro Gly Thr Ile Lys Glu Asn
            35                  40                  45

Ile Ile Phe Gly Val Ser Tyr Asp Glu Tyr Lys Tyr Lys Ser Val Ile
 50                  55                  60

Gln Ala Cys Gln Leu Glu Glu Asp Ile Leu Lys Phe Pro Asp Lys Asp
 65                  70                  75                  80

Tyr Thr Val Leu Gly Glu Gly Gly Ile Ile Leu Ser Gly Gly Gln Arg
                85                  90                  95

Ala Arg Ile Ser
            100

<210> SEQ ID NO 17
<211> LENGTH: 100
<212> TYPE: PRT
<213> ORGANISM: Unknown
<220> FEATURE:
<223> OTHER INFORMATION: shark

<400> SEQUENCE: 17

Gly Ser Thr Gly Ser Gly Lys Ser Ser Leu Leu Met Met Ile Met Gly
 1               5                  10                  15

Glu Leu Glu Pro Ser Asp Gly Lys Ile Lys His Ser Gly Arg Ile Ser
                20                  25                  30

Tyr Ser Pro Gln Val Pro Trp Ile Met Pro Gly Thr Ile Lys Asp Asn
            35                  40                  45

Ile Ile Phe Gly Leu Ser Tyr Asp Glu Tyr Lys Tyr Thr Ser Val Val
 50                  55                  60

Asn Ala Cys Gln Leu Glu Glu Asp Ile Thr Val Phe Pro Asn Lys Asp
 65                  70                  75                  80

Lys Thr Val Leu Gly Asp Gly Gly Ile Thr Leu Ser Gly Gly Gln Arg
                85                  90                  95

Ala Arg Ile Ser
            100

<210> SEQ ID NO 18
<211> LENGTH: 100
<212> TYPE: PRT
<213> ORGANISM: Danio rerio

<400> SEQUENCE: 18

Gly Ser Met Gly Ser Gly Lys Ser Ser Leu Met Thr Ile Leu Gly
 1               5                  10                  15

Glu Leu Val Pro Ser Ser Gly Lys Ile Arg His Ser Gly Arg Ile Ser
                20                  25                  30

Tyr Ser Ser Gln Thr Ala Trp Ile Met Pro Gly Thr Ile Arg Asp Asn
            35                  40                  45

Ile Leu Phe Gly Leu Thr Tyr Asp Glu Tyr Lys Tyr Lys Ser Val Val
 50                  55                  60

Lys Ala Cys Gln Leu Glu Glu Asp Leu Ala Ala Leu Pro Glu Lys Asp
 65                  70                  75                  80

Lys Thr Pro Met Ala Glu Gly Gly Leu Asn Leu Ser Gly Gly Gln Lys
                85                  90                  95

Ala Arg Val Ala
            100
```